US007838219B2

(12) United States Patent
Padgett et al.

(10) Patent No.: US 7,838,219 B2
(45) Date of Patent: *Nov. 23, 2010

(54) METHOD OF INCREASING COMPLEMENTARITY IN A HETERODUPLEX

(75) Inventors: Hal S. Padgett, Vacaville, CA (US); John A. Lindbo, Vacaville, CA (US); Wayne P. Fitzmaurice, Vacaville, CA (US); Andrew A. Vaewhongs, Vacaville, CA (US)

(73) Assignee: Novici Biotech LLC, Vacaville, CA (US)

( * ) Notice: Subject to any disclaimer, the term of this patent is extended or adjusted under 35 U.S.C. 154(b) by 375 days.

This patent is subject to a terminal disclaimer.

(21) Appl. No.: 10/637,758

(22) Filed: Aug. 8, 2003

(65) Prior Publication Data

US 2004/0180352 A1 Sep. 16, 2004

Related U.S. Application Data

(63) Continuation-in-part of application No. 10/280,913, filed on Oct. 25, 2002, now Pat. No. 7,582,423, and a continuation-in-part of application No. 10/226,372, filed on Aug. 21, 2002, now abandoned, and a continuation-in-part of application No. 10/066,390, filed on Feb. 1, 2002, now abandoned.

(60) Provisional application No. 60/402,342, filed on Aug. 8, 2002, provisional application No. 60/268,785, filed on Feb. 14, 2001, provisional application No. 60/266,386, filed on Feb. 2, 2001.

(51) Int. Cl.
C12Q 1/68 (2006.01)
C12P 19/34 (2006.01)

(52) U.S. Cl. .......................................... 435/6; 435/91.2

(58) Field of Classification Search ........................ None
See application file for complete search history.

(56) References Cited

U.S. PATENT DOCUMENTS

| 4,994,368 | A | 2/1991 | Goodman et al. |
|---|---|---|---|
| 5,459,039 | A | 10/1995 | Modrich et al. |
| 5,556,747 | A | 9/1996 | Kumar |
| 5,571,676 | A | 11/1996 | Shuber |
| 5,679,522 | A | 10/1997 | Modrich et al. |
| 5,683,877 | A | 11/1997 | Lu-Chang et al. |
| 5,723,323 | A | 3/1998 | Kauffman et al. |
| 5,795,747 | A | 8/1998 | Henco et al. |
| 5,861,482 | A | 1/1999 | Modrich et al. |
| 5,869,245 | A | 2/1999 | Yeung et al. |
| 5,877,280 | A | 3/1999 | Wetmur |
| 5,922,539 | A | 7/1999 | Modrich et al. |
| 6,057,103 | A | 5/2000 | Short |
| 6,165,793 | A | 12/2000 | Stemmer |
| 6,391,557 | B1 | 5/2002 | Yeung |
| 6,537,746 | B2 | 3/2003 | Arnold et al. |
| 6,783,941 | B2 | 8/2004 | Vind |
| 6,821,758 | B1 | 11/2004 | Koltermann |
| 6,846,655 | B1 | 1/2005 | Wagner et al. |
| 7,056,740 | B2 * | 6/2006 | Padgett et al. ............... 435/440 |
| 7,078,211 | B2 * | 7/2006 | Padgett et al. ............... 435/199 |
| 7,217,514 | B2 * | 5/2007 | Padgett et al. .................. 435/6 |
| 7,235,386 | B2 * | 6/2007 | Padgett et al. .............. 435/91.2 |
| 2002/0045175 | A1 | 4/2002 | Wang et al. |
| 2002/0146732 | A1 * | 10/2002 | Padgett et al. .................. 435/6 |
| 2002/0177160 | A1 * | 11/2002 | Padgett et al. .................. 435/6 |
| 2003/0017477 | A1 | 1/2003 | Vind |
| 2003/0148315 | A1 * | 8/2003 | Padgett et al. .................. 435/6 |
| 2003/0157495 | A1 * | 8/2003 | Padgett et al. .................. 435/6 |
| 2003/0186261 | A1 * | 10/2003 | Padgett et al. .................. 435/6 |
| 2004/0048268 | A1 | 3/2004 | Delcourt et al. |
| 2004/0091886 | A1 | 5/2004 | Moore |
| 2004/0110130 | A1 * | 6/2004 | Padgett et al. .................. 435/6 |
| 2006/0194288 | A1 * | 8/2006 | Padgett et al. .............. 435/69.1 |
| 2008/0145913 | A1 * | 6/2008 | Padgett et al. ............... 435/197 |

FOREIGN PATENT DOCUMENTS

DE 4112440 10/1992

(Continued)

OTHER PUBLICATIONS

Dalbadie-McFarland et al. Oligonucleotide-directed mutagenesis as a general and powerful method for studies of protein function. Proceedings of the National Academy of Sciences, USA 79: 6409-6413 (1982).*

(Continued)

*Primary Examiner*—Young J Kim
*Assistant Examiner*—Angela M Bertagna
(74) *Attorney, Agent, or Firm*—Wayne P. Fitzmaurice

(57) ABSTRACT

We describe here an in vitro method of increasing complementarity in a heteroduplex polynucleotide sequence. The method uses annealing of opposite strands to form a polynucleotide duplex with mismatches. The heteroduplex polynucleotide is combined with an effective amount of enzymes having strand cleavage activity, 3' to 5' exonuclease activity, and polymerase activity, and allowing sufficient time for the percentage of complementarity to be increased within the heteroduplex. Not all heteroduplex polynucleotides will necessarily have all mismatches resolved to complementarity. The resulting polynucleotide is optionally ligated. Several variant polynucleotides result. At sites where either of the opposite strands has templated recoding in the other strand, the resulting percent complementarity of the heteroduplex polynucleotide sequence is increased. The parent polynucleotides need not be cleaved into fragments prior to annealing heterologous strands. Therefore, no reassembly is required.

19 Claims, 16 Drawing Sheets

FOREIGN PATENT DOCUMENTS

| | | |
|---|---|---|
| DE | 19953854 | 5/2001 |
| FR | 2789696 | 8/2000 |
| WO | WO 92/18645 | 10/1992 |
| WO | WO 93/20233 | 10/1993 |
| WO | WO 96/40902 | 12/1996 |
| WO | WO 97/37011 | 10/1997 |
| WO | WO 97/46701 | 12/1997 |
| WO | WO 99/28451 | 6/1999 |
| WO | WO 99/29902 | 6/1999 |
| WO | WO 00/71730 | 11/2000 |
| WO | WO 01/34835 | 5/2001 |
| WO | WO 01/62974 | 8/2001 |
| WO | WO-0164864 A2 * | 9/2001 |
| WO | WO 02/24953 A1 | 3/2002 |
| WO | WO 02/079468 | 10/2002 |
| WO | WO-02092815 A2 * | 11/2002 |
| WO | WO 03066809 A2 * | 8/2003 |
| WO | WO 2004/035771 | 4/2004 |

OTHER PUBLICATIONS

Oleykowski, et al., "Mutation detection using a novel plant endonuclease", Nucleic Acids Research, 1998, vol. 26, No. 20, pp. 4597-4602, Oxford University Press, United Kingdom.

Oleykowski, et al., "Incision at Nucleotide Insertions/Deletions and Base Pair Mismatches by the SP Nuclease of Spinach", Biochemistry, 1999, vol. 38, pp. 2200-2205, American Chemical Society, Columbus. OH.

Biswas and Hsieh, "Identification and characterization of a thermostable MutS homolog from Thermus aquaticus", J. Biol. Chem. (1996) 271(9):5040-5048.

Kraemer and Digiovanna, "Topical enzyme therapy for skin diseases?", J. Am. Acad. Dermatol. (2002) 46:463-6.

O'Grady, et al., "DNA repair in thermophiles: investigation of DNA-binding activities in Thermus aquaticus", Biochem. Soc. Tranactions (1997) 25:319-22.

Sugahara, et al., "Crystal structure of a repair enzyme of oxidatively damaged DNA, MutM (Fpg), from an extreme thermophile, Thermus thermophilus HB8", EMBO J (2000) 19(15):3857-3869.

Wang, "Creating hybrid genes by homologous recombination", Disease Markers (2000) 16:3-13.

Birkenkamp and Kemper, "In vitro processing of heteroduplex loops and mismatches by Endonuclease VII", DNA Research, 1995, vol. 2, pp. 9-14.

Abastado, et al., "Processing of complex heteroduplexes in Escherichia coli and Cos-1 monkey cells", Proc. Natl. Acad. Sci. USA, Sep. 1984, vol. 81, pp. 5792-5796.

Cami, et al., "Correction of complex heteroduplexes made of mouse H-2 gene sequences in Escherichia coli K-12", Proc. Natl. Acad. Sci. USA, Jan. 1984, vol. 81, pp. 503-507.

Chang, et al, "Recombination following transformation of Escherichia coli by heteroduplex plasmid DNA molecules", Gene, 1984, vol. 29, pp. 255-261, Elsevier.

Cotton, "Slowly but surely towards better scanning for mutations", TIG, Feb. 1997, vol. 13, No. 2, pp. 43-46, Elsevier Science Ltd.

Joyce, "Directed Molecular Evolution", Scientific American, Dec. 1992, pp. 90-97.

Kulinski, et al., "CEL I Enzymatic Mutation Detection Assay", Biotechniques, Jul. 2000, vol. 29, pp. 44-48.

Lahue, et al., "Requirement for d(GATC) sequences in Escherichia coli mutHLS mismatch correction", Proc. Natl. Acad. Sci. USA, Mar. 1987, vol. 84, pp. 1482-1486.

Modrich, "Strand-specific Mismatch Repair in Mammalian Cells", The Journal of Biological Chemistry, Oct. 3, 1997, vol. 272, No. 4, pp. 24727-24730, The American Society of for Biochemistry and Molecular Biology, Inc., Bethesda, MD.

Oleykowski, et al., "Mutation detection using a novel plant endonuclease", Nucleic Acids Research, 1998, vol. 26, No. 20, pp. 4597-4602, Oxford University Press, United Kingdom.

Oleykowski, et al., "Incision at Nucleotide Insertions/Deletions and Base Pair Mismatches by the SP Nuclease of Spinach", Biochemistry, 1999, vol. 38, pp. 2200-2205, American Chemical Society, Columbus. OH.

Robertson, "Directed evolution patent could have major impact", Nature Biotechnology, May 1998, vol. 16, p. 411.

Solaro, et al., "Endonuclease VII of Phage T4 Triggers Mismatch Correction in Vitro", J. Mol. Biol., 1993, vol. 230, pp. 868-877, Academic Press Limited.

Volkov, et al., "Random Chimeragenesis by Heteroduplex Recombination", Methods in Enzymology, 2000, vol. 328, pp. 456-463, Academic Press.

Volkov, et al., "Recombination and chimeragenesis by in vitro heteroduplex formation and in vivo repair", Nucleic Acids Research, 1999, vol. 27, No. 18, pp. e18 (i-vi), Oxford Univeristv Press.

Yang, et al., "Purification, Cloning, and Characterization of the CEL I Nuclease", Biochemistry, 2000, vol. 39, pp. 3533-3541; American Chemical Society.

Solaro, et al., "Endonuclease VII of Phage T4 Triggers Mismatch Correction in Vitro", J. Mol. Biol., 1993, vol. 230, pp. 868-877, Academic Press Limited.

Yang, et al., "Purification, Cloning, and Characterization of the CEL I Nuclease", Biochemistry, 2000, vol. 39, pp. 3533-3541, American Chemical Society.

Kulinski, et al., "CEL I Enzymatic Mutation Detection Assay", Biotechniques, Jul. 2000, vol. 29, pp. 44-48.

Fishel, R. and R. Kolodner, Gene coversion in Escherichia coli: the recF pathway for resolution of heteroduplex DNA. J Bacteriol, 1989. 171(6): p. 3046-52.

Fishel, R.A. and R. Kolodner, An Escherichia coli cell-free system that catalyzes the repair of symmetrically methylated heteroduplex DNA. Cold Spring Herb Symp Quant Biol, 1984. 49: p. 603-9.

Glaser, P.M., et al., DNA mismatch repair detected in human cell extracts. Mol Cell Biol, 1987. 7(1): p. 218-24.

Paabo, S., D.M. Irwin, and A.C. Wilson, DNA damage promotes jumping between templates during enzymatic amplification. J Biol Chem, 1990. 265(8): p. 4718-21.

Su, S.S., et al., Mispair specificity of methyl-directed DNA mismatch correction in vitro. J Biol Chem, 1988. 263(14): p. 6829-35.

Sung, W.L., et al., Simultaneous synthesis of human-, mouse- and chimeric epidermal growth factor genes via 'hybrid gene synthesis' approach. Nucleic Acids Res, 1986. 14(15): p. 6159-68.

Weber, H. and C. Weissmann, Formation of genes coding for hybrid proteins by recombination between related, cloned genes in E. coli. Nucleic Acids Res, 1983. 11(16): p. 5661-9.

Mashal, R, et al. "Detection of mutations by cleavage of DNA heteroduplexes with bacteriophage resolvases", Nature Genetics 9(1995)177-183.

Pochart, P. et al. "Conserved properties between functionally distinct MutS homologs in yeast", J Biol Chem 272 (1997)30345-30349.

Singer, M. et al. "Genes and Genomes", University Science Books, p. 280, publication date= 1991.

Kumagai, M. et al. "Rapid high-level expression of biologically active alpha-trichosanthin in transfected plants by an RNA viral vector", PNAS 90(1993)427-430.

Kunkel, T.A., et al., "Efficient site-directed mutagenesis using uracil-containing DNA", Meth Enzymol 204(1991) 125-139.

Jendrisiak, J. et al., "In vitro insertion of transposon containing an E. coli origin of replication facilitates rapid recovery, propagation and sequencing of circular DNA molecules from heterologous organisms", EPICENTER Forum 9(2002)14-15.

Parikh, S.S. et al., "Base excision repair enzyme family portrait: integrating the structure and chemistry of an entire DNA repair pathway", Structure 5(1997)1543-1550.

Cooper, D.L., et al, "Methyl-directed mismatch repair is bidirectional", J Biol Chem 268(1993)11823-11829.

Lahue, R.S., et al., "DNA mismatch correction in a defined system", Science 245(1989)160-164.

Youil, R. et al., "Screening for mutations by enzyme mismatch cleavage with T4 endonuclease VII", PNAS 92(1995) 87-91.

* cited by examiner

| Possible Strand Combinations | Possible +/- Strand Combinations | Partially Complementary Populations |
|---|---|---|
| 1+/2- | ✓ | |
| 1+/3+ | | |
| 1+/4- | ✓ | ✓ |
| 2-/3+ | ✓ | ✓ |
| 2-/4- | | |
| 3+/4- | ✓ | |

FIG. 3

```
atggcaacga ccaagacgag cgggatggcg ctggctttgc tcctcgtcgc cgccctggcc
gtgggagctg cggcctgggg gaaagagggc catcgcctca cttgtatggt cgccgagccc
tttctaagct ctgaatccaa gcaagctgtg gaggagcttc tctctggaag agatctcccg
gacttgtgtt catgggccga tcagattcga agatcgtata agtttagatg gactggtcct
ttgcactaca tcgatactcc agacaacctc tgcacctatg actatgatcg tgactgccac
gattcccatg ggaagaagga cgtgtgtgtc gctggtggga tcaacaatta ctcgtcgcag
ctggaaacgt ttctagattc agagagctcg tcgtataact tgaccgaggc gctgctcttc
ctggctcact ttgtcgggga tatacaccag cccttgcacg tagcatttac gagtgatgcc
ggaggcaatg gcgtgcacgt ccgctggttt ggacgaaagg ccaacttgca tcacgtctgg
gatacagaat ttatttctag agccaatcgt gtgtactacc acgacatttc caagatgctc
cggaacatta ccaggagcat aactaagaag aatttcaata gttggagcag atgtaagact
gatccggcgg cttgtattga tagttatgcg acagaaagta tagatgcttc ttgcaactgg
gcatacaaag acgcacccga cggaagctct ctagatgatg attacttctc ttcacgcctt
ccaattgttg agcagcgtct tgctcaaggg ggcgtcaggc tggcgtcaat actcaacagg
attttggag gagcaaagtc gaacaggtcc agtcgctcaa gcatgtag
```

FIG. 4

Met Ala Thr Thr Lys Thr Ser Gly Met Ala Leu Ala Leu Leu Val

Ala Ala Leu Ala Val Gly Ala Ala Ala Trp Gly Lys Glu Gly His Arg

Leu Thr Cys Met Val Ala Glu Pro Phe Leu Ser Ser Glu Ser Lys Gln

Ala Val Glu Glu Leu Leu Ser Gly Arg Asp Leu Pro Asp Leu Cys Ser

Trp Ala Asp Gln Ile Arg Arg Ser Tyr Lys Phe Arg Trp Thr Gly Pro

Leu His Tyr Ile Asp Thr Pro Asp Asn Leu Cys Thr Tyr Asp Tyr Asp

Arg Asp Cys His Asp Ser His Gly Lys Lys Asp Val Cys Val Ala Gly

Gly Ile Asn Asn Tyr Ser Ser Gln Leu Glu Thr Phe Leu Asp Ser Glu

Ser Ser Ser Tyr Asn Leu Thr Glu Ala Leu Leu Phe Leu Ala His Phe

Val Gly Asp Ile His Gln Pro Leu His Val Ala Phe Thr Ser Asp Ala

Gly Gly Asn Gly Val His Val Arg Trp Phe Gly Arg Lys Ala Asn Leu

His His Val Trp Asp Thr Glu Phe Ile Ser Arg Ala Asn Arg Val Tyr

Tyr His Asp Ile Ser Lys Met Leu Arg Asn Ile Thr Arg Ser Ile Thr

Lys Lys Asn Phe Asn Ser Trp Ser Arg Cys Lys Thr Asp Pro Ala Ala

Cys Ile Asp Ser Tyr Ala Thr Glu Ser Ile Asp Ala Ser Cys Asn Trp

Ala Tyr Lys Asp Ala Pro Asp Gly Ser Ser Leu Asp Asp Tyr Phe

Ser Ser Arg Leu Pro Ile Val Glu Gln Arg Leu Ala Gln Gly Gly Val

Arg Leu Ala Ser Ile Leu Asn Arg Ile Phe Gly Gly Ala Lys Ser Asn

Arg Ser Ser Arg Ser Ser Met

FIG. 5

```
gtggcactt  tcggggaaat  gtgcgcggaa  cccctatttg  tttattttc   taaatacatt  caaatatgta
tccgctcatg  agacaataac  cctgataaat  gcttcaataa  tattgaaaaa  ggaagagtat  gagtattcaa
catttccgtg  tcgcccttat  tcccttttt   gcggcatttt  gccttcctgt  ttttgctcac  ccagaaacgc
tggtgaaagt  aaaagatgct  gaagatcagt  tgggtgcacg  agtgggttac  atcgaactgg  atctcaacag
cggtaagatc  cttgagagtt  ttcgcccccga agaacgtttt  ccaatgatga  gcactttaa   agttctgcta
tgtggcgcgg  tattatcccg  tattgacgcc  gggcaagagc  aactcggtcg  ccgcatacac  tattctcaga
atgacttggt  tgagtactca  ccagtcacag  aaaagcatct  tacgatggc   atgacagtaa  gagaattatg
cagtgctgcc  ataaccatga  gtgataacac  tgcggccaac  ttacttctga  caacgatcgg  aggaccgaag
gagctaaccg  ctttttgca   caacatgggg  gatcatgtaa  ctcgccttga  tcgttgggaa  ccggagctga
atgaagccat  accaaacgac  gagcgtgaca  ccacgatgcc  tgtagcaatg  gcaacaacgt  tgcgcaaact
attaactggc  gaactactta  ctctagcttc  ccggcaacaa  ttaatagact  ggatggaggc  ggataaagtt
gcaggaccac  ttctgcgctc  ggcccttccg  gctggctggt  ttattgctga  taaatctgga  gccggtgagc
gtgggtctcg  cggtatcatt  gcagcactgg  ggccagatgg  taagccctcc  cgtatcgtag  ttatctacac
gacggggagt  caggcaacta  tggatgaacg  aaatagacag  atcgctgaga  taggtgcctc  actgattaag
cattggtaac  tgtcagacca  agtttactca  tatatacttt  agattgattt  aaaacttcat  ttttaattta
aaaggatcta  ggtgaagatc  cttttgata   atctcatgac  caaaatccct  taacgtgagt  tttcgttcca
ctgagcgtca  gacccgtag   aaaagatcaa  aggatcttct  tgagatcctt  tttttctgcg  cgtaatctgc
tgcttgcaaa  caaaaaacc   accgctacca  gcggtggttt  gtttgccgga  tcaagagcta  ccaactcttt
ttccgaaggt  aactggcttc  agcagagcgc  agataccaaa  tactgtcctt  ctagtgtagc  cgtagttagg
ccaccacttc  aagaactctg  tagcaccgcc  tacatacctc  gctctgctaa  tcctgttacc  agtggctgct
gccagtggcg  ataagtcgtg  tcttaccggg  ttggactcaa  gacgatagtt  accggataag  gcgcagcggt
cgggctgaac  ggggggttcg  tgcacacagc  ccagcttgga  gcgaacgacc  tacaccgaac  tgagatacct
acagcgtgag  ctatgagaaa  gcgccacgct  tcccgaaggg  agaaaggcgg  acaggtatcc  ggtaagcggc
agggtcggaa  caggagagcg  cacgagggag  cttccagggg  gaaacgcctg  gtatctttat  agtcctgtcg
ggtttcgcca  cctctgactt  gagcgtcgat  ttttgtgatg  ctcgtcaggg  gggcggagcc  tatggaaaaa
cgccagcaac  gcggcctttt  tacggttcct  ggccttttgc  tggccttttg  ctcacatgtt  ctttcctgcg
ttatcccctg  attctgtgga  taaccgtatt  accgcctttg  agtgagctga  taccgctcgc  cgcagccgaa
cgaccgagcg  cagcgagtca  gtgagcgagg  aagcggaaga  gcgcccaata  cgcaaaccgc  ctctccccgc
gcgttggccg  attcattaat  gcagctggca  cgacaggttt  cccgactgga  aagcgggcag  tgagcgcaac
gcaattaatg  tgagttagct  cactcattag  gcaccccagg  ctttacactt  tatgcttccg  gctcgtatgt
tgtgtggaat  tgtgagcgga  taacaattc   acacaggaaa  cagctatgac  catgattacg  ccaagcgcgc
aattaaccct  cactaaggg   aacaaaagct  gggtaccgat  gagtaaagga  gaagaacttt  tcactggagt
tgtcccaatt  cttgttgaat  tagatggtga  tgttaatggg  cacaaatttt  ctgtcagtgg  agagggtgaa
ggtgatgcta  catacggaaa  gcttaccctt  aaatttattt  gcactactgg  aaaactacct  gttccatggc
caacacttgt  cactactttc  tcttatggtg  ttcaatgctt  ttcccgttat  ccggatcata  tgaaacggca
tgacttttc   aagagtgcca  tgcccgaagg  ttatgtacag  gaacgcacta  tatctttcaa  agatgacggg
aactacaaga  cgcgtgctga  agtcaagttt  gaaggtgata  cccttgttaa  tcgtatcgag  ttaaaaggta
ttgattttaa  agaagatgga  aacattctcg  gacacaaact  cgagtacaac  tataactcac  acaatgtata
catcacggca  gacaaacaaa  agaatggaat  caaagctaac  ttcaaaattc  gccacaacat  tgaagatgga
tccgttcaac  tagcagacca  ttatcaacaa  aatactccaa  ttggcgatgg  ccctgtcctt  ttaccagaca
accattacct  gtcgacacaa  tctgcccttt  cgaaagatcc  caacgaaaag  cgtgaccaca  tggtccttct
tgagtttgta  actgctgctg  ggattacaca  tggcatggat  gaactataca  ataagaatt   cctgcagccc
ggggatcca  ctagttctag  agcggccgcc  accgcggtgg  agctccaatt  cgccctatag  tgagtcgtat
tacgcgcgct  cactggccgt  cgttttacaa  cgtcgtgact  gggaaaaccc  tggcgttacc  caacttaatc
gccttgcagc  acatccccct  ttcgccagct  ggcgtaatag  cgaagaggcc  cgcaccgatc  gcccttccca
acagttgcgc  agcctgaatg  gcgaatggga  cgcgcctgt   agcggcgcat  taagcgcggc  gggtgtggtg
gttacgcgca  gcgtgaccgc  tacacttgcc  agcgccctag  cgcccgctcc  tttcgctttc  ttcccttcct
ttctcgccac  gttcgccggc  tttccccgtc  aagctctaaa  tcggggctc   ccttaggggt  tccgatttag
tgctttacgg  cacctcgacc  ccaaaaaact  tgattagggt  gatggttcac  gtagtgggcc  atcgccctga
tagacggttt  ttcgcccttt  gacgttggag  tccacgttct  ttaatagtgg  actcttgttc  caaactggaa
caacactcaa  ccctatctcg  gtctattctt  ttgatttata  agggattttg  ccgatttcgg  cctattggtt
aaaaaatgag  ctgatttaac  aaaaatttaa  cgcgaatttt  aacaaaatat  taacgcttac  aatttag
```

FIG. 6

```
atgtcttacg agcctaaagt gagcgacttc cttgctctta cgaaaaagga ggaaatttta
cccaaggctc ttacgaggtt aaagactgtc tctattagta ctaaggatgt tatatctgtt
aaggattctg agtccctgtg tgatatagat ttactagtta atgtgccatt agataagtat
agatatgtgg gtgttttagg tgttgttttt accggtgagt ggttagtgcc ggatttcgtt
aaaggtggag taacagtgag cgtgattgac aaacggcttg agaactccaa agagtgcata
attggtacgt acagagctgc tgcgaaagac aaaaggttcc agttcaagct ggttccaaat
tacttcgtgt ctgttgcaga tgccaagcga aaaccgtggc aagttcatgt gcgtattcaa
aatttaagga ttgaagctgg atggcaacct ctggccttag aggtggtttc tgttgctatg
gtcactaata acgtggttgt taagggtttg agagaaaagg tcatcgcagt gaatgatccg
aatgtcgaag gtttcgaagg cgtggttgac gatttcgtcg attcggtcgc agcattcaag
gcggttgaca ctttcagaaa gaaaaagaaa aggattggag gaaaggatgt aaataataat
aagtttagat ataccgga gagatacgcc ggtcaggatt cgttaaatta taaagaagaa
aacgtcttac aacatcacga actcgaatca gtaccagtat ttcgcagcga cgtgggcaga
gcccacagcg atgctt
```

FIG. 7

```
atgtcaaagg ctattgtcaa gatcgatgaa ttcattaaat tatccaagtc tgaagaggtt
ttaccttctg cattcacaag aatgaagtcg gtcagagtct caacagtgga taagataatg
gccaaagaga atgacaatat ttccgaagta gatttactta agggtgttaa gttagttaaa
aatggttatg tttgtttagt aggtcttgtg gtgtcaggag agtggaattt acccgacaac
tgcagaggtg gtgtaagtat ctgtctgata gacaaacgta tgcaacgtca taacgaagct
actttaggtt cgtacactac caaagccagc aagaaaaact tttcgttcaa gcttataccg
aattactcga taacctctca agatgctgaa aggcgtcctt gggaagttat ggtaaatatt
cgtggtgtgg ctatgtccga aggttggtgt ccattatcct tagagttcgt ttctgtttgt
attgttcata aaaacaatgt tagaaagggt ctaagagaga aggtgactgc cgtgtccgaa
gacgacgcta tagaactcac agaagaggtt gttgatgagt ttatagaagc cgtaccgatg
gcgcgacgtt tgcagaactt gagaaaccc aagtacaaca aagaaaaaga aaataaaaat
ttgaataata aaaatagtat aggagtttcc aaacctgtcg gtttggaaag aaataaagta
aggagtgtag ttagaaaagg ggttaggagt gatagtagtt taggtgtgac tgatatgagt
caggacggta gctcaagcga gatatcatcc gattcgttta ttt
```

FIG. 8

```
atggctgtta gtctcagaga tactgtcaaa attagcgagt tcattgatct ttcgaaacag
gatgagatac ttccggcatt catgactaag gtcaagagcg tcagaatatc gactgtggac
aagattatgg ctgttaagaa tgatagtctt tctgatgtag atttacttaa aggtgttaag
ttagttaaga atgggtacgt gtgcttagct ggtttggtag tgtctgggga gtggaatctc
ccggacaact gccgtggtgg tgtcagtgtt tgtattgtag ataagagaat gaaaaggagt
aaggaggcaa cgctgggtgc gtatcacgcc cctgcttgca aaaagaattt ttcctttaag
ctaatcccta attattcaat aacatccgag gatgctgaga agcacccatg gcaagtatta
gtgaatatca aaggagtggc tatggaagaa ggatactgtc ctttatcttt ggagttcgtt
tcaatttgtg tagtacataa aaataatgta agaaaaggtt tgagggaacg tattttgaga
gtaacagacg gctcgccaat tgaactcact gaaaaagttg ttgaggagtt catagatgaa
gtaccaatgg ctgtgaaact cgaaaggttc cggaaaacaa aaaagagagt ggtaggtaat
agtgttaata ataagaaaat aaataatagt ggtaagaaag gtttgaaagt tgaggaaatt
gaggataatg taagtgatga cgagtctatc gcgtcatcga gtacgttttt
```

FIG. 9

```
atggctctag ttgttaaagg taaggtaaat attaatgagt ttatcgatct gtcaaagtct
gagaaacttc tcccgtcgat gttcacgcct gtaaagagtg ttatggtttc aaaggttgat
aagattatgg tccatgaaaa tgaatcattg tctgaagtaa atctcttaaa aggtgtaaaa
cttatagaag gtgggtatgt ttgcttagtt ggtcttgttg tgtccggtga gtggaattta
ccagataatt gccgtggtgg tgtgagtgtc tgcatggttg acaagagaat ggaaagagcg
gacgaagcca cactggggtc atattacact gctgctgcta aaaagcggtt tcagtttaaa
gtggtcccaa attacggtat tactacaaag gatgcagaaa agaacatatg gcaagttcat
gtgcgtattc aaaatttaag gattgaagct ggatggcaac ctctggcctt agaggtggtt
tctgttgcta tggtcactaa taacgtggtt gttaagggtt tgagagaaaa ggtcatcgca
gtgaatgatc cgaatgtcga aggtttcgaa ggcgtggttg acgatttcgt cgattcggtc
gcagcattca aggcggttga cactttcaga aagaaaaaga aaggattgg aggaaaggat
gtaaataata ataagtttag atatagaccg gagagatacg ccggtcagga ttcgttaaat
tataaagaag aaaacgtctt acaacatcac gaactcgaat cagtaccagt atttcgcagc
gacgtgggca gagcccacag cgatgctt
```

FIG. 10

```
atgtcttacg agcctaaagt gagcgacttc cttgctctta cgaaaaagga ggaaatttta
cccaaggctc ttacgaggtt aaagactgtc tctattagta ctaaggatgt tatatctgtt
aaggattctg agtccctgtg tgatatagat ttactagtta atgtgccatt agataagtat
agatatgtgg gtgttttagg tgttgttttt accggtgagt ggaatttacc agataattgc
cgtggtggtg tgagtgtctg catggttgac aagagaatgg aaagagcgga cgaagccaca
ctggggtcat attacactgc tgctgcgaaa gacaaaaggt tccagttcaa gctggttcca
aattacttcg tgtctgttgc agatgccaag cgaaaaccgt ggcaagttca tgtgcgtatt
caaaatttaa ggattgaagc tggatggcaa cctctggcct tagaggtggt ttctgttgct
atggtcacta ataacgtggt tgttaagggt ttgagagaaa aggtcatcgc agtgaatgat
ccgaatgtcg aaggtttcga aggcgtggtt gacgatttcg tcgattcggt cgcagcattc
aaggcggttg acactttcag aaagaaaaag aaaaggattg gaggaaagga tgtaaataat
aataagttta gatatagacc ggagagatac gccggtcagg attcgttaaa ttataaagaa
gaaaacgtct tacaacatca cgaactcgaa tcagtaccag tatttcgcag cgacgtgggc
agagcccaca gcgatgctt
```

FIG. 11

```
aaataaacga atcggatgat atctcgcttg agctaccgtc ctgactcata tcagtcacac
ctaaactact atcactccta acccctttc taactacact ccttacttta tttctttcca
aaccgacagg tttggaaact cctatactat ttttattatt caaatttta ttttcttttt
ctttgttgta cttgggtttt ctcaagttct gcaaacgtcg cgccatcggt acggcttcta
taaactcatc aacaacctct tctgtgagtt ctatagcgtc gtcttcggac acggcagtca
ccttctctct tagacccttt ctaacattgt ttttatgaac aatacaaaca gaaacgaact
ctaaggataa tggacaccaa ccttcggaca tagccacacc acgaatattt accataactt
cccaaggacg cctttcagca tcttgagagg ttatcgagta attcggtata agcttgaacg
aaaagttttt cttgctggct ttggtagtgt acgaacctaa agtagcttcg ttatgacgtt
gcatacgttt gtctatcaga cagatactta caccacctct gcagttgtcg ggtaaattcc
actctcctga caccacaaga cctactaaac aaacataacc accttctata agttttacac
cttttaagag atttacttca gacaatgatt cattctcttt ggccattatc ttatccactg
ttgagactct gaccgacttc attcttgtga atgcagaagg taaaacctct tcagacttgg
ataatttaat gaattcatcg atcttgacaa tagcctttga cat
```

FIG. 12

```
aatacgaatc agaatccgcg accgacgtct cggcttcatc ttcaatcaaa ttatcaaact
cttttcaac  ttcatcaaaa cttttggtt  taggccttcc gcctgaacgc cccttaccta
aattattatt attttcgga  cctcttttg  aggatttggt tcgaaacttt gcgagtctaa
ccgacattgg aacattctcc atgaactcat caacaacctc ttctgtgagt tctatagcgt
cgtcttcgga cacggcagtc accttctctc ttagacccctt tctaacattg tttttatgaa
caatacaaac agaaacgaac tctaatgaca aagggcagta gcccgcactc attttacat
ttttaatatt tactaagacc tgccatatgt tcttttctgc atcctttgta gtaataccgt
aatttgggac cactttaaac tgaaaccgct ttttagcagc agcagtgtaa tatgacccca
gtgtggcttc gtccgctctt tccattctct tgtcaaccat gcagacactc acaccaccac
ggcaattatc tggtaaattc cactctcctg acaccacaag acctactaaa caaacataac
catttaac   taacttaaca cccttaagag atttacttcg gacaatgatt catttcatg
gaccataatc ttatcaacct ttgaaaccat aacactcttt acaggcgtga atgcagaagg
taaaacctct tcagactttg acagatcgat aaactcatta atatttacct tacctttaac
aactagagcc at
```

FIG. 13

```
aatacgaatc agaatccgcg atagactcgt catcacttac attatcctca atttcctcaa
ctttcaaacc tttcttacca ctattattta ttttcttatt attaacacta ttacctacca
ctctcttttt tgttttccgg aacctttcga gtttcacagc cattggtact tcatctatga
actcatcaac aacttcttct gaaagttcca tgggtcctcc atcgttcaca ctcgttactt
tctccctcaa acccaatttt atattatttt tataaacaat acacacagac acaaattcta
aagataaagg gcagtatcct tcttccatag ccactccttt gatattcact aatacttgcc
atgggtgctt ttctgcatcc tcggatgtta ttgaataatt agggaccact ttaaactgaa
accgcttttt agcagcaggg gcgtgatacg cacccagcgt tgcctcctta ctcctttcca
ttctcttgtc aaccatgcag acactcacac caccacggca gttgtccggg agattccact
caccggacac aacaagacca actaagcaaa catacccacc ttctataagt tttacacctt
ttaagagatt tacttcagac aatgattcat tttcatggac cataatctta tcaacctttg
aaaccataac actctttaca ggcgtgaaca tcgacgggag aagtttctca gactttgaca
gatcgataaa ctcattaata tttaccttac ctttaacaac tagagccat
```

FIG. 14

```
aatacgaatc agaatccgcg accgacgtct cggcttcact tacattatcc tcaatttcct
caactttcaa aactttctta ccactattat ttattttctt attattaaca ctattaccta
ccactctctt ttttgttttc cggaaccttt cgagtttcac agccattggt acttcatcta
tgaactcatc aacaactttt tcagtgagtt caattggcga gccgtctgtt actctcaaaa
tacgttccct caaacccaat tttatattat ttttataaac aatacacaca gacacaaatt
ctaatgacaa agggcagtag cccgcactca ttttttacatt tttaatattt actaagacct
gccatgggtg cttctcagca tcctcggatg ttattgaata attagggatt agcttaaagg
aaaaattctt tttgcaagca ggggcgtgat acgcacccag tgtggcttcg tccgctcttt
ccattctctt gtcaaccatg cagacactca caccaccacg gcagttgtcc gggagattcc
actcaccgga cacaacaaga ccaactaagc acacgtaccc attcttaact aacttaacac
ctttaagtaa atctacatca gacaatgatt cattttcatg gaccataatc ttatcaacct
ttgaaaccat aacactcttt acaggcgtga acatcgacgg gagaagtttc tcagactttg
acagatcgat aaactcgcta attttgacag tatctctgag actaacagcc at
```

FIG. 15

```
atggctctag ttgttaaagg aaaagtgaat attaatgagt ttatcgatct gtcaaagtct
gagaaacttc tcccgtcgat gttcacgcct gtaaagagtg ttatggtttc aaaggttgat
aagattatgg tccatgaaaa tgaatcattg tctgaagtaa atctcttaaa aggtgtaaaa
cttatagaag gtgggtatgt ttgcttagtt ggtcttgttg tgtccggtga gtggaattta
ccagataatt gccgtggtgg tgtgagtgtc tgcatggttg acaagagaat ggaaagagcg
gacgaagcca ctctcggatc ttactacaca gcagctgcaa agaaaagatt tcagttcaag
gtcgttccca attatgctat aaccacccag gacgcgatga aaaacgtctg gcaagtttta
gttaatatta gaaatgtgaa gatgtcagcg ggtttctgtc cgctttctct ggagtttgtg
tctgtgtgta ttgtttataa aaataatata aaattgggtt tgagggagaa agtaacgagt
gtgaacgatg gaggacccat ggaactttca gaagaagttg ttgatgagtt catggaagat
gtcccaatgt cggttagact cgcaaagttt cgatctcgaa ccggaaaaaa gagtgatgtc
cgcaaaggga aaaatagtag tagtgatcgg tcagtgccga acaagaacta tagaaatgtt
aaggattttg gaggaatgag ttttaaaaag aataatttaa tcgatgatga ttcggagacg
tcggtcgcgg attctgattc gtatt
```

FIG. 16

```
atggctctag ttgttaaagg aaaagtgaat atcaatgagt ttatcgacct gacaaagtct
gagaaacttc tcccgtcgat gtttacccct gtaaagagtg ttatggttcc aaagttgata
agattatggt tcatgagaat gagtcattgt caggggtgaa ccttcttaaa ggagttaagc
ttattgatag tggatacgtc tgtttagccg gtttggtcgt cacgggcgag tggaacttgc
ctgacaattg ccgtggtggt gtgagcgtgt gtctggtgga caagagaatg gaaagagcgg
acgaagccac actggggtca tattacactg ctgctgctaa aaagcggttt cagttcaagg
tcgttcccaa ttatgctata accacccagg atgcagaaaa gaacatatgg caggtcttag
taaatattaa aaatgtgaag atgagtgcgg gctactgccc tttgtcatta gaatttgtgt
cggtgtgtat tgtttataga aataatataa aattgggttt gagagagaaa gtaacgagtg
tgaacgatgg agggcccatg gaacttacag aagaagtcgt tgatgagttc atggaagatg
tccctatgtc gatcaggctt gcaaagtttc gatctcgaat cctcaaaaag agtgatgtcc
gcaaagggaa aaatagtagt agtgatcggt cagtgccgaa caagaactat agaaatgtta
aggattttgg aggaatgagt tttaaaaaga ataatttaat cgatgatgat tcggaggcta
ctgtcgcgga ttctgattcg tttt
```

METHOD OF INCREASING COMPLEMENTARITY IN A HETERODUPLEX

CROSS REFERENCE TO RELATED APPLICATIONS

This application claims the benefit of U.S. Provisional Application No. 60/402,342, filed Aug. 8, 2002. This application is a continuation-in-part of U.S. application Ser. No. 10/226,372 (now abandoned), filed Aug. 21, 2002, which claims the benefit of U.S. Provisional Application No. 60/402,342, and is also a continuation-in-part of U.S. application Ser. No. 10/066,390 (now abandoned), filed Feb. 1, 2002. This application is also a continuation-in-part of U.S. application Ser. No. 10/280,913 (now U.S. Pat. No. 7,582,423), filed Oct. 25, 2002, which claims the benefit of U.S. Provisional Application No. 60/402,342. U.S. applications Ser. No. 10/280,913 is a continuation-in-part of U.S. application Ser. No. 10/066,390. U.S. application Ser. No. 10/066,390 claims the benefit of U.S. Provisional Application No. 60/268,785, filed Feb. 14, 2001 and U.S. Provisional Application No. 60/266,386, filed Feb. 2, 2001.

FIELD OF THE INVENTION

The invention relates generally to molecular biology and more specifically to methods of generating populations of related nucleic acid molecules.

BACKGROUND INFORMATION

DNA shuffling is a powerful tool for obtaining recombinants between two or more DNA sequences to evolve them in an accelerated manner. The parental, or input, DNAs for the process of DNA shuffling are typically mutants or variants of a given gene that have some improved character over the wild-type. The products of DNA shuffling represent a pool of essentially random reassortments of gene sequences from the parental DNAs that can then be analyzed for additive or synergistic effects resulting from new sequence combinations.

Recursive sequence reassortment is analogous to an evolutionary process where only variants with suitable properties are allowed to contribute their genetic material to the production of the next generation. Optimized variants are generated through DNA shuffling-mediated sequence reassortment followed by testing for incremental improvements in performance. Additional cycles of reassortment and testing lead to the generation of genes that contain new combinations of the genetic improvements identified in previous rounds of the process. Reassorting and combining beneficial genetic changes allows an optimized sequence to arise without having to individually generate and screen all possible sequence combinations.

This differs sharply from random mutagenesis, where subsequent improvements to an already improved sequence result largely from serendipity. For example, in order to obtain a protein that has a desired set of enhanced properties, it may be necessary to identify a mutant that contains a combination of various beneficial mutations. If no process is available for combining these beneficial genetic changes, further random mutagenesis will be required. However, random mutagenesis requires repeated cycles of generating and screening large numbers of mutants, resulting in a process that is tedious and highly labor intensive. Moreover, the rate at which sequences incur mutations with undesirable effects increases with the information content of a sequence. Hence, as the information content, library size, and mutagenesis rate increase, the ratio of deleterious mutations to beneficial mutations will increase, increasingly masking the selection of further improvements. Lastly, some computer simulations have suggested that point mutagenesis alone may often be too gradual to allow the large-scale block changes that are required for continued and dramatic sequence evolution.

There are a number of different techniques used for random mutagenesis. For example, one method utilizes error-prone polymerase chain reaction (PCR) for creating mutant genes in a library format, (Cadwell and Joyce, 1992; Gram et al., 1992). Another method is cassette mutagenesis (Arkin and Youvan, 1992; Delagrave et al., 1993; Delagrave and Youvan, 1993; Goldman and Youvan, 1992; Hermes et al., 1990; Oliphant et al., 1986; Stemmer et al., 1993) in which the specific region to be optimized is replaced with a synthetically mutagenized oligonucleotide.

Error-prone PCR uses low-fidelity polymerization conditions to introduce a low level of point mutations randomly over a sequence. A limitation to this method, however, is that published error-prone PCR protocols suffer from a low processivity of the polymerase, making this approach inefficient at producing random mutagenesis in an average-sized gene.

In oligonucleotide-directed random mutagenesis, a short sequence is replaced with a synthetically mutagenized oligonucleotide. To generate combinations of distant mutations, different sites must be addressed simultaneously by different oligonucleotides. The limited library size that is obtained in this way, relative to the library size required to saturate all sites, means that many rounds of selection are required for optimization. Mutagenesis with synthetic oligonucleotides requires sequencing of individual clones after each selection round followed by grouping them into families, arbitrarily choosing a single family, and reducing it to a consensus motif. Such a motif is resynthesized and reinserted into a single gene followed by additional selection. This step creates a statistical bottleneck, is labor intensive, and is not practical for many rounds of mutagenesis.

For these reasons, error-prone PCR and oligonucleotide-directed mutagenesis can be used for mutagenesis protocols that require relatively few cycles of sequence alteration, such as for sequence fine-tuning, but are limited in their usefulness for procedures requiring numerous mutagenesis and selection cycles, especially on large gene sequences.

As discussed above, prior methods for producing improved gene products from randomly mutated genes are of limited utility. One recognized method for producing a wide variety of randomly reasserted gene sequences uses enzymes to cleave a long nucleotide chain into shorter pieces. The cleaving agents are then separated from the genetic material, and the material is amplified in such a manner that the genetic material is allowed to reassemble as chains of polynucleotides, where their reassembly is either random or according to a specific order. ((Stemmer, 1994a; Stemmer, 1994b), U.S. Pat. No. 5,605,793, U.S. Pat. No. 5,811,238, U.S. Pat. No. 5,830,721, U.S. Pat. No. 5,928,905, U.S. Pat. No. 6,096,548, U.S. Pat. No. 6,117,679, U.S. Pat. No. 6,165,793, U.S. Pat. No. 6,153,410). A variation of this method uses primers and limited polymerase extensions to generate the fragments prior to reassembly (U.S. Pat. No. 5,965,408, U.S. Pat. No. 6,159,687).

However, both methods have limitations. These methods suffer from being technically complex. This limits the applicability of these methods to facilities that have sufficiently experienced staffs. In addition there are complications that arise from the reassembly of molecules from fragments, including unintended mutagenesis and the increasing difficulty of the reassembly of large target molecules of increasing size, which limits the utility of these methods for reassembling long polynucleotide strands.

Another limitation of these methods of fragmentation and reassembly-based gene shuffling is encountered when the parental template polynucleotides are increasingly heterogeneous. In the annealing step of those processes, the small polynucleotide fragments depend upon stabilizing forces that result from base-pairing interactions to anneal properly. As the small regions of annealing have limited stabilizing forces due to their short length, annealing of highly complementary sequences is favored over more divergent sequences. In such instances these methods have a strong tendency to regenerate the parental template polynucleotides due to annealing of complementary single-strands from a particular parental template. Therefore, the parental templates essentially reassemble themselves creating a background of unchanged polynucleotides in the library that increases the difficulty of detecting recombinant molecules. This problem becomes increasingly severe as the parental templates become more heterogeneous, that is, as the percentage of sequence identity between the parental templates decreases. This outcome was demonstrated by Kikuchi, et al., (Gene 243:133-137, 2000) who attempted to generate recombinants between xylE and nahH using the methods of family shuffling reported by Patten et al., 1997; Crameri et al., 1998; Harayama, 1998; Kumamaru et al., 1998; Chang et al., 1999; Hansson et al., 1999). Kikuchi, et al., found that essentially no recombinants (<1%) were generated. They also disclosed a method to improve the formation of chimeric genes by fragmentation and reassembly of single-stranded DNAs. Using this method, they obtained chimeric genes at a rate of 14 percent, with the other 86 percent being parental sequences.

The characteristic of low-efficiency recovery of recombinants limits the utility of these methods for generating novel polynucleotides from parental templates with a lower percentage of sequence identity, that is, parental templates that are more diverse. Accordingly, there is a need for a method of generating gene sequences that addresses these needs.

The present invention provides a method that satisfies the aforementioned needs, and also provides related advantages as well.

SUMMARY OF THE INVENTION

The present invention provides a method for reasserting mutations among related polynucleotides, in vitro, by forming heteroduplex molecules and then addressing the mismatches such that sequence information at sites of mismatch is transferred from one strand to the other. In one preferred embodiment, the mismatches are addressed by incubating the heteroduplex molecules in a reaction containing a mismatch nicking enzyme, a polymerase with a 3' to 5' proofreading activity in the presence of dNTPs, and a ligase. These respective activities act in concert such that, at a given site of mismatch, the heteroduplex is nicked, unpaired bases are excised then replaced using the opposite strand as a template, and nicks are sealed. Output polynucleotides are amplified before cloning, or cloned directly and tested for improved properties. Additional cycles of mismatch resolution reassortment and testing lead to further improvement.

BRIEF DESCRIPTION OF THE FIGURES

FIG. 2 depicts an exemplary partially complementary nucleic acid population of two molecules. FIG. 2A shows the sequence of two nucleic acid molecules "X" (SEQ ID NO: 40; 5'-AGATCAATTG-3' and its fully complementary strand) and "Y" (SEQ ID NO: 41; 5'-AGACCGATTG-3' and its fully complementary strand) having completely complementary top/bottom strands 1+/2− and 3+/4−, respectively. The positions of differing nucleotides between the nucleic acids X and Y are indicated (*). FIG. 2B shows possible combinations of single strands derived from nucleic acids X and Y after denaturing and annealing and indicates which of those combinations would comprise a partially complementary nucleic acid population of two.

FIG. 3 shows nucleic acid sequence for RES I endonuclease (SEQ ID NO: 16) as taught in Example 13.

FIG. 4 shows the corresponding amino acid sequence for RES I (SEQ ID NO: 34).

FIG. 5 shows the nucleic acid sequence for plasmid pBSC3BFP (SEQ ID NO: 32) as taught in Example 14.

FIG. 6 shows the nucleic acid sequence for the tobamovirus movement protein open reading frame of TMV-Cg (SEQ ID NO: 18) as taught in Example 15.

FIG. 7 shows the nucleic acid sequence for the tobamovirus movement protein open reading frame of TMV-Ob (SEQ ID NO: 19) as taught in Example 15.

FIG. 8 shows the nucleic acid sequence for the tobamovirus movement protein open reading frame of TMV-U2 (SEQ ID NO: 20) as taught in Example 15.

FIG. 9 shows a resultant clone from a TMV-Cg and ToMv GRAMMR reaction (SEQ ID NO: 21) as taught in Example 15.

FIG. 10 shows a second resultant clone from a TMV-Cg and ToMv GRAMMR reaction (SEQ ID NO: 22) as taught in Example 15.

FIG. 11 shows a resultant clone from a TMV-Ob and ToMv GRAMMR reaction (SEQ ID NO: 23) as taught in Example 15.

FIG. 12 shows a second resultant clone from a TMV-Ob and ToMv GRAMMR reaction (SEQ ID NO: 24) as taught in Example 15.

FIG. 13 shows a resultant clone from a TMV-U2 and ToMv GRAMMR reaction (SEQ ID NO: 25) as taught in Example 15.

FIG. 14 shows a second resultant clone from a TMV-U2 and ToMv GRAMMR reaction (SEQ ID NO: 26) as taught in Example 15.

FIG. 15 shows a resultant clone from a TMV-U1 and ToMv GRAMMR reaction (SEQ ID NO: 27) as taught in Example 15.

FIG. 16 shows a second resultant clone from a TMV-U1 and ToMv GRAMMR reaction (SEQ ID NO: 28) as taught in Example 15.

DEFINITIONS

Figure 1:
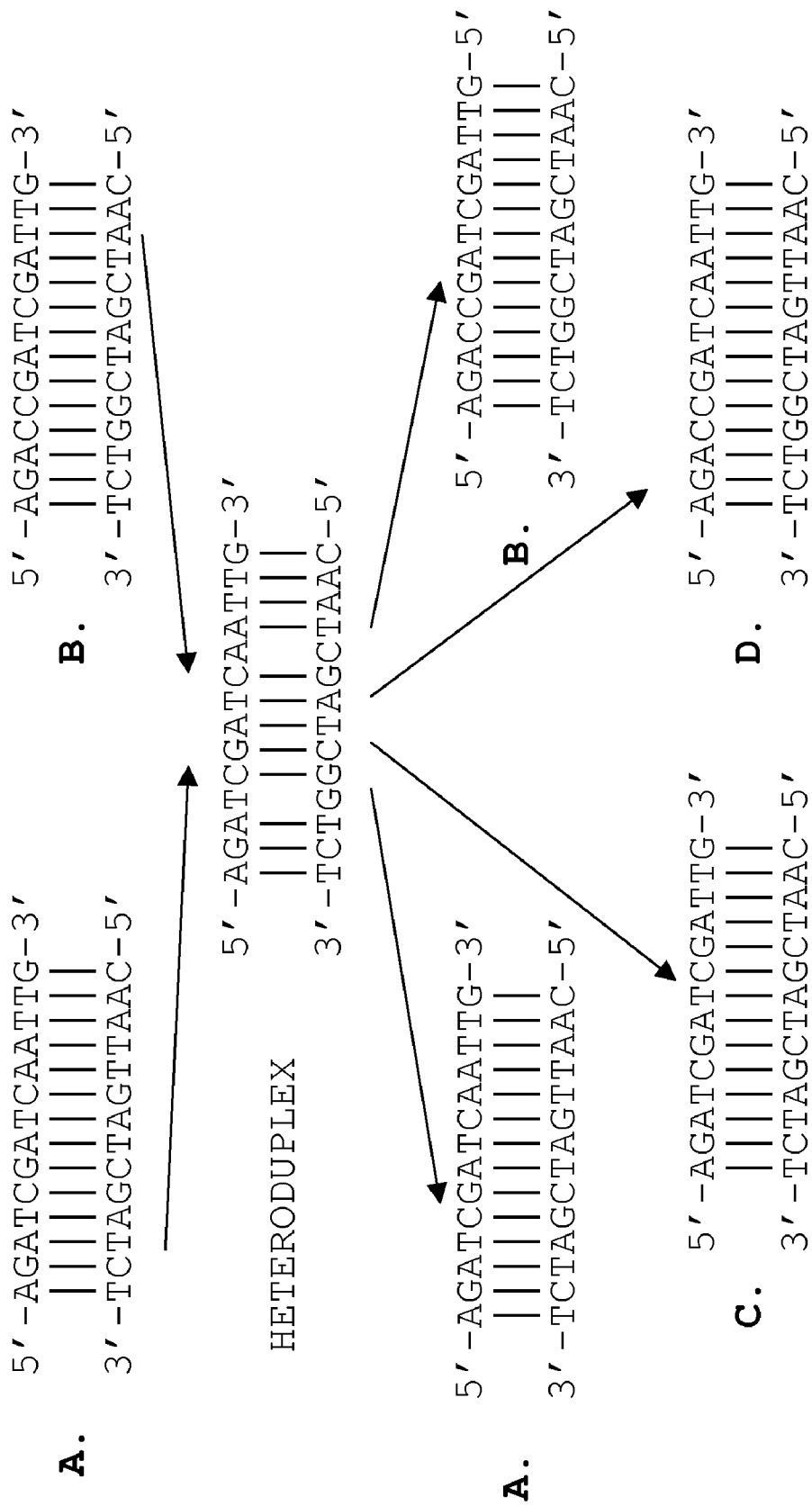
FIG. 1 depicts the process of Genetic ReAssortment by Mismatch Resolution (GRAMMR). Reassortment is contemplated between two hypothetical polynucleotides differing at at least two nucleotide positions. Annealing between the top strand of A (SEQ ID NO: 36; 5'-AGATCGATCAATTG-3') and the bottom strand of B (fully complementary strand of SEQ ID NO:37; SEQ ID NO: 37 is 5'-AGACCGATCGATTG-3' is shown (labeled HETERODUPLEX) which results in mismatches at the two positions. After the process of reassortment by mismatch resolution, four distinct product polynucleotides are seen, the parental types A (SEQ ID NO: 36 and its fully complementary strand) and B (SEQ ID NO: 37 and its fully complementary strand), and the reassorted products C (SEQ ID NO: 38; 5'-AGATCGATCGATTG-3' and its fully complementary strand) and D (SEQ ID NO: 39; 5'-AGACCGATCAATTG-3' and its fully complementary strand).

As used herein the term "amplification" refers to a process where the number of copies of a polynucleotide is increased.

As used herein, "annealing" refers to the formation of at least partially double stranded nucleic acid by hybridization of at least partially complementary nucleotide sequences. A partially double stranded nucleic acid can be due to the hybridization of a smaller nucleic acid strand to a longer nucleic acid strand, where the smaller nucleic acid is 100% identical to a portion of the larger nucleic acid. A partially double stranded nucleic acid can also be due to the hybridization of two nucleic acid strands that do not share 100% identity but have sufficient homology to hybridize under a particular set of hybridization conditions.

As used herein, "clamp" refers to a unique nucleotide sequence added to one end of a polynucleotide, such as by incorporation of the clamp sequence into a PCR primer. The clamp sequences are intended to allow amplification only of polynucleotides that arise from hybridization of strands from different parents (i.e., heteroduplex molecules) thereby ensuring the production of full-length hybrid products as described previously (Skarfstad, J. Bact, vol 182, No 11, P. 3008-3016).

As used herein the term "cleaving" means digesting the polynucleotide with enzymes or otherwise breaking phosphodiester bonds within the polynucleotide.

As used herein the term "complementary basepair" refers to the correspondence of DNA (or RNA) bases in the double helix such that adenine in one strand is opposite thymine (or uracil) in the other strand and cytosine in one strand is opposite guanine in the other.

As used herein the term "complementary to" is used herein to mean that the complementary sequence is identical to the reverse-complement of all or a portion of a reference polynucleotide sequence or that each nucleotide in one strand is able to form a base-pair with a nucleotide, or analog thereof in the opposite strand. For illustration, the nucleotide sequence "TATAC" is complementary to a reference sequence "GTATA".

As used herein, "denaturing" or "denatured," when used in reference to nucleic acids, refers to the conversion of a double stranded nucleic acid to a single stranded nucleic acid. Methods of denaturing double stranded nucleic acids are well known to those skilled in the art, and include, for example, addition of agents that destabilize base-pairing, increasing temperature, decreasing salt, or combinations thereof. These factors are applied according to the complementarity of the strands, that is, whether the strands are 100% complementary or have one or more non-complementary nucleotides.

As used herein the term "desired functional property" means a phenotypic property, which include but are not limited to, encoding a polypeptide, promoting transcription of linked polynucleotides, binding a protein, improving the function of a viral vector, and the like, which can be selected or screened for. Polynucleotides with such desired functional properties, can be used in a number of ways, which include but are not limted to expression from a suitable plant, animal, fungal, yeast, or bacterial expression vector, integration to form a transgenic plant, animal or microorganism, expression of a ribozyme, and the like.

As used herein the term "DNA shuffling" is used herein to indicate recombination between substantially homologous but non-identical sequences.

As used herein, the term "effective amount" refers to the amount of an agent necessary for the agent to provide its desired activity. For the present invention, this determination is well within the knowledge of those of ordinary skill in the art.

As used herein the term "exonuclease" refers to an enzyme that cleaves nucleotides one at a time from an end of a polynucleotide chain, that is, an enzyme that hydrolyzes phosphodiester bonds from either the 3' or 5' terminus of a polynucleotide molecule. Such exonucleases, include but are not limited to T4 DNA polymerase, T7 DNA polymerase, E. coli Pol 1, and Pfu DNA polymerase. The term "exonuclease activity" refers to the activity associated with an exonuclease. An exonuclease that hydrolyzes in a 3' to 5' direction is said to have "3' to 5' exonuclease activity." Similarly an exonuclease with 5' to 3' activity is said to have "5' to 3' exonuclease activity." it is noted that some exonucleases are known to have both 3' to 5', 5' to 3' activity, such as, E. coli Pol I.

As used herein, "Genetic Reassortment by Mismatch Resolution (GRAMMR)" refers to a method for reasserting sequence variations among related polynucleotides by forming heteroduplex molecules and then addressing the mismatches such that information is transferred from one strand to the other.

As used herein, "granularity" refers to the amount of a nucleic acid's sequence information that is transferred as a contiguous sequence from a template polynucleotide strand to a second polynucleotide strand. As used herein, "template sequence" refers to a first single stranded polynucleotide sequence that is partially complementary to a second polynucleotide sequence such that treatment by GRAMMR results in transfer of genetic information from the template strand to the second strand.

The larger the units of sequence information transferred from a template strand, the higher the granularity. The smaller the blocks of sequence information transferred from the template strand, the lower or finer the granularity. Lower granularity indicates that a DNA shuffling or reassortment method is able to transfer smaller discrete blocks of genetic information from the template strand to the second strand. The advantage of a DNA shuffling or reassortment method with lower granularity is that it is able to resolve smaller nucleic acid sequences from others, and to transfer the sequence information. DNA shuffling or reassortment methods that return primarily high granularity are not readily able to resolve smaller nucleic acid sequences from others.

As used herein the term "heteroduplex polynucleotide" refers to a double helix polynucleotide formed by annealing single strands, typically separate strands, where the strands are non-identical. A heteroduplex polynucleotide may have unpaired regions existing as single strand loops or bubbles. A heteroduplex polynucleotide region can also be formed by one single-strand polynucleotide wherein partial self-complementarity allows the formation of a stem-loop structure where the annealing portion of the strand is non-identical.

As used herein the term "heteroduplex DNA" refers to a DNA double helix formed by annealing single strands, typically separate strands), where the strands are non-identical. A heteroduplex DNA may have unpaired regions existing as single strand loops or bubbles. A heteroduplex DNA region can also be formed by one single-strand polynucleotide wherein partial self-complementarity allows the formation of a stem-loop structure where the annealing portion of the strand is non-identical.

As used herein the term "homologous" means that one single-stranded nucleic acid sequence may hybridize to an at least partially complementary single-stranded nucleic acid sequence. The degree of hybridization may depend on a number of factors including the amount of identity between the sequences and the hybridization conditions such as temperature and salt concentrations as discussed later.

Nucleic acids are "homologous" when they are derived, naturally or artificially, from a common ancestor sequence. During natural evolution, this occurs when two or more descendent sequences diverge from a parent sequence over time, i.e., due to mutation and natural selection. Under artificial conditions, divergence occurs, e.g., in one of two basic ways. First, a given sequence can be artificially recombined with another sequence, as occurs, e.g., during typical cloning, to produce a descendent nucleic acid, or a given sequence can be mutated (random or directed), chemically modified, or otherwise manipulated to modify the resulting molecule. Alternatively, a nucleic acid can be synthesized de novo, by synthesizing a nucleic acid that varies in sequence from a selected parental nucleic acid sequence. When there is no explicit knowledge about the ancestry of two nucleic acids, homology is typically inferred by sequence comparison between two sequences. Where two nucleic acid sequences show sequence similarity over a significant portion of each of the nucleic acids, it is inferred that the two nucleic acids share a common ancestor. The precise level of sequence similarity that establishes homology varies in the art depending on a variety of factors.

For purposes of this disclosure, two nucleic acids are considered homologous where they share sufficient sequence identity to allow GRAMMR-mediated information transfer to occur between the two nucleic acid molecules regardless of the origin of each parental nucleic acid.

As used herein the term "identical" or "identity" means that two nucleic acid sequences have the same sequence or a complementary sequence. Thus, "areas of identity" means that regions or areas of a polynucleotide or the overall polynucleotide are identical or complementary to areas of another polynucleotide.

As used herein the term "increase in percent complementarity" means that the percentage of complementary base-pairs in a heteroduplex molecule is made larger.

As used herein the term, "ligase" refers to an enzyme that rejoins a broken phosphodiester bond in a nucleic acid.

As used herein the term "mismatch" refers to a base-pair that is unable to form normal base-pairing interactions (i.e., other than "A" with "T" (or "U"), or "G" with "C").

As used herein the term "mismatch resolution" refers to the conversion of a mismatched base-pair into a complementary base-pair.

As used herein the term "mutations" means changes in the sequence of a wild-type or reference nucleic acid sequence or changes in the sequence of a polypeptide. Such mutations can be point mutations such as transitions or transversions. The mutations can be deletions, insertions or duplications.

As used herein the term "nick translation" refers to the property of a polymerase where the combination of a 5'-to-3' exonuclease activity with a 5'-to-3' polymerase activity allows the location of a single-strand break in a double-stranded polynucleotide (a "nick") to move in the 5'-to-3' direction.

As used herein, the term "nucleic acid" or "nucleic acid molecule" means a polynucleotide such as deoxyribonucleic acid (DNA) or ribonucleic acid (RNA) and encompasses single-stranded and double-stranded nucleic acid as well as an oligonucleotide. Nucleic acids useful in the invention include genomic DNA, cDNA, mRNA and synthetic oligonucleotides, and can represent the sense strand, the anti-sense strand, or both. A nucleic acid generally incorporates the four naturally occurring nucleotides adenine, guanine, cytosine, and thymidine/uridine. An invention nucleic acid can also incorporate other naturally occurring or non-naturally occurring nucleotides, including derivatives thereof, so long as the nucleotide derivatives can be incorporated into a polynucleotide by a polymerase at an efficiency sufficient to generate a desired polynucleotide product.

As used herein, a "parental nucleic acid" refers to a double stranded nucleic acid having a sequence that is 100% identical to an original single stranded nucleic acid in a starting population of partially complementary nucleic acids. Parental nucleic acids would include, for example in the illustration of FIG. 2, nucleic acids X and Y if partially complementary nucleic acid combinations 1+/4− or 2−/3+ were used as a starting population in an invention method.

As used herein, "partially complementary" refers to a nucleic acid having a substantially complementary sequence to another nucleic acid but that differs from the other nucleic acid by at least two or more nucleotides. As used herein, "partially complementary nucleic acid population" refers to a population of nucleic acids comprising nucleic acids having substantially complementary sequences but no nucleic acids having an exact complementary sequence for any other member of the population. As used herein, any member of a partially complementary nucleic acid population differs from another nucleic acid of the population, or the complement thereto, by two or more nucleotides. As such, a partially complementary nucleic acid specifically excludes a population containing sequences that are exactly complementary, that is, a complementary sequence that has 100% complementarity. Therefore, each member of such a partially complementary nucleic acid population differs from other members of the population by two or more nucleotides, including both strands. One strand is designated the top strand, and its complement is designated the bottom strand. As used herein, "top" strand refers to a polynucleotide read in the 5' to 3' direction and the "bottom" its complement. it is understood that, while a sequence is referred to as bottom or top strand, such a designation is intended to distinguish complementary strands since, in solution, there is no orientation that fixes a strand as a top or bottom strand.

For example, a population containing two nucleic acid members can be derived from two double stranded nucleic acids, with a potential of using any of the four strands to generate a single stranded partially complementary nucleic acid population. An example of potential combinations of strands of two nucleic acids that can be used to obtain a partially complementary nucleic acid population of the invention is shown in FIG. 2. The two nucleic acid sequences that are potential members of a partially complementary nucleic acid population are designated "X" (AGATCAATTG) (SEQ ID NO: 40) and "Y" (AGACCGATTG) (SEQ ID NO: 41) (FIG. 2A). The nucleic acid sequences differ at two positions (positions 4 and 6 indicated by "*"). The "top" strand of nucleic acids X and Y are designated "1+" and "3+," respectively, and the "bottom" strand of nucleic acids X and Y are designated "2−" and "4−," respectively.

FIG. 2B shows the possible combinations of the four nucleic acid strands. Of the six possible strand combinations, only the combination of 1+/2−, 1+/4−, 2−/3+, or 3+/4− comprise the required top and bottom strand of a partially complementary nucleic acid population. Of these top/bottom sequence combinations, only 1+/4− or 2−/3+comprise an example of a partially complementary nucleic acid population of two different molecules because only these combinations have complementary sequences that differ by at least one nucleotide. The remaining combinations, 1+/2− and 2+/4−, contain exactly complementary sequences and therefore do not comprise a partially complementary nucleic acid population of the invention.

In the above described example of a population of two different molecules, a partially complementary population of nucleic acid molecules excluded combinations of strands that differ by one or more nucleotides but which are the same sense, for example, 1+/3+ or 2−/4−. However, it is understood that such a combination of same stranded nucleic acids can be included in a larger population, so long as the population contains at least one bottom strand and at least one top strand. For example, if a third nucleic acid "Z," with strands 5+ and 6− is included, the combinations 1+/3+/6− or 2−/4−/5+ would comprise a partially complementary nucleic acid population. Similarly, any number of nucleic acids and their corresponding top and bottom strands can be combined to generate a partially complementary nucleic acid population of the invention so long as the population contains at least one top strand and at least one bottom strand and so long as the population contains no members that are the exact complement.

The populations of nucleic acids of the invention can be about 3 or more, about 4 or more, about 5 or more, about 6 or more, about 7 or more, about 8 or more, about 9 or more, about 10 or more, about 12 or more, about 15 or more, about 20 or more, about 25 or more about 30 or more, about 40 or more, about 50 or more, about 75 or more, about 100 or more, about 150 or more, about 200 or more, about 250 or more, about 300 or more, about 350 or more, about 400 or more, about 450 or more, about 500 or more, or even about 1000 or more different nucleic acid molecules. A population can also contain about 2000 or more, about 5000 or more, about $1\times10^4$ or more, about $1\times10^5$ or more, about $1\times10^6$ or more, about $1\times10^7$ or more, or even about $1\times10^8$ or more different nucleic acids. One skilled in the art can readily determine a desirable population to include in invention methods depending on the nature of the desired reassortment experiment outcome and the available screening methods, as disclosed herein.

As used herein, a "polymerase" refers to an enzyme that catalyzes the formation of polymers of nucleotides, that is, polynucleotides. A polymerase useful in the invention can be derived from any organism or source, including animal, plant, bacterial and viral polymerases. A polymerase can be a DNA polymerase, RNA polymerase, or a reverse transcriptase capable of transcribing RNA into DNA.

As used herein the term "proofreading" describes the property of an enzyme where a nucleotide, such as, a mismatch nucleotide, can be removed by a 3'-to-5' exonuclease activity and replaced by, typically, a base-paired nucleotide.

As used herein, a "recombinant" polynucleotide refers to a polynucleotide that comprises sequence information from at least two different polynucleotides.

As used herein the term "related polynucleotides" means that regions or areas of the polynucleotides are identical and regions or areas of the polynucleotides are non-identical.

As used herein the term DNA "reassortment" is used herein to indicate a redistribution of sequence variations between substantially homologous but non-identical sequences.

As used herein the term "replicon" refers to a genetic unit of replication including a length of polynucleotide and its site for initiation of replication.

As used herein the term "sequence diversity" refers to the abundance of non-identical polynucleotides. The term "increasing sequence diversity in a population" means to increase the abundance of non-identical polynucleotides in a population.

As used herein the term "sequence variant" is used herein refers to a molecule (DNA, RNA polypeptide, and the like) with one or more sequence differences compared to a reference molecule. For example, the sum of the separate independent mismatch resolution events that occur throughout the heteroduplex molecule during the GRAMMR process results in reassortment of sequence information throughout that molecule. The sequence information will reassort in a variety of combinations to generate a complex library of "sequence variants".

As used herein the term "strand cleavage activity" or "cleavage" refers to the breaking of a phosphodiester bond in the backbone of the polynucleotide strand, as in forming a nick. Strand cleavage activity can be provided by an enzymatic agent, such agents include, but are not limited to CEL I, RES I, T4 endonuclease VII, T7 endonuclease I, S1 nuclease, BAL-31 nuclease, FEN1, cleavase, pancreatic DNase I, SP nuclease, mung bean nuclease, and nuclease P1; by a chemical agent, such agents include, but are not limited to potassium permanganate, tetraethylammonium acetate, sterically bulky photoactivatable DNA intercalators, [Rh(bpy)2 (chrysi)]3+, osmium tetroxide with piperidine, and hydroxylamine with piperidine; or by energy in the form of ionizing radiation, or kinetic radiation.

As used herein the term "sufficient time" refers to the period time necessary for a reaction or process to render a desired product. For the present invention, the determination of sufficient time is well within the knowledge of those of ordinary skill in the art. If is noted that "sufficient time" can vary widely, depending on the desires of the practitioner, without impacting on the functionality of the reaction, or the quality of the desired product.

As used herein the term "wild-type" means that a nucleic acid fragment does not contain any mutations. A "wild-type" protein means that the protein will be active at a level of activity found in nature and typically will be the amino acid sequence found in nature. In an aspect, the term "wild type" or "parental sequence" can indicate a starting or reference sequence prior to a manipulation of the invention. A "parental sequence" may be a sequence other than "wild type".

In the polypeptide notation used herein, the left-hand direction is the amino terminal direction and the right-hand direction is the carboxy-terminal direction, in accordance with standard usage and convention. Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction.

DETAILED DESCRIPTION OF THE INVENTION

The present invention provides an in vitro method of making sequence variants from at least one heteroduplex polynucleotide wherein the heteroduplex has at least two non-complementary nucleotide base pairs, the method comprising: preparing at least one heteroduplex polynucleotide; combining said heteroduplex polynucleotide with an effective amount of an agent or agents with exonuclease activity, polymerase activity and strand cleavage activity; and allowing sufficient time for the percentage of complementarity to increase, wherein at least one or more variants are made.

Another aspect of the present invention is where the heteroduplex polynucleotides are circular, linear or a replicon.

Another aspect of the present invention is where the desired variants have different amounts of complementarity.

Another aspect of the present invention is where the exonuclease activity, polymerase activity, and strand cleavage activity is added sequentially, or concurrently.

Another aspect of the present invention provides the addition of ligase activity, provided by agents such as, T4 DNA ligase, E. coli DNA ligase, or Taq DNA ligase.

Another aspect of the present invention is where the strand cleavage activity is provided by an enzyme, such as, CEL I, RES I, T4 endonuclease VII, T7 endonuclease I, S1 nuclease, BAL-31 nuclease, FEN1, cleavase, pancreatic DNase I, SP nuclease, mung bean nuclease, and nuclease P1; a chemical agent, such as, potassium permanganate, tetraethylammonium acetate, sterically bulky photoactivatable DNA intercalators, [Rh(bpy)2(chrysi)]3+, osmium tetroxide with piperidine, and hydroxylamine with piperidine or a form of energy, such as, ionizing or kinetic radiation.

Another aspect of the present invention is where polymerase activity is provided by Pol beta.

Another aspect of the present invention is where both polymerase activity and 3' to 5' exonuclease activity is provided T4 DNA polymerase, T7 DNA polymerase, E. coli Pol 1, or Pfu DNA polymerase.

Another aspect of the present invention is where the agent with both polymerase activity and 5' to 3' exonuclease activity is E. coli Pol 1.

Another aspect of the present invention is where the agent with polymerase activity lacks 3' to 5' exonuclease activity (such as Taq DNA polymerase, VentR (exo-) DNA polymerase, Deep VentR (exo-) DNA polymerase, Therminator DNA polymerase, or Klenow Fragment (3' to 5'exo-) (enzymes available from New England BioLabs), T4 DNA polymerase (3' to 5' exo-), or Klentaq (Barnes, Genell2(92)29), and the like), and the agent with the 3' to 5' exonuclease activity lacks polymerase activity (such as E. coli exonuclease iii (Exo iii) or Ape1 (Hadi, et al., J Mol Biol 316, (02)853)). In the case of polymerases with strand displacement activity, it is preferred to also add an agent with flap endonuclease activity such as T4 RNaseH (Bhagwat, et al., J Biol Chem 272 (1997) 28523) and the like.

An embodiment of the present invention is where the effective amount of strand cleavage activity, and exonuclease activity/polymerase activity and ligase activity are provided by RES I, T4 DNA polymerase, and T4 DNA ligase.

Another aspect of the present invention is where the effective amount of strand cleavage activity, and exonuclease activity/polymerase activity and ligase activity are provided by RES I, T7 DNA polymerase, and T4 DNA ligase.

Another embodiment of the present invention provides an in vitro method of increasing diversity in a population of sequences, comprising, preparing at least one heteroduplex polynucleotide; combining the heteroduplex polynucleotide with an effective amount of an agent or agents with 3' to 5' exonuclease activity, polymerase activity and strand cleavage activity; and allowing sufficient time for the percentage of complementarity to increase, wherein diversity in the population is increased.

Another embodiment of the present invention provides a method of obtaining a polynucleotide encoding a desired functional property, comprising: preparing at least one heteroduplex polynucleotide; combining said heteroduplex polynucleotide with an effective amount of an agent or agents with exonuclease activity, polymerase activity and strand cleavage activity; allowing sufficient time for the percentage of complementarity between strands of the heteroduplex polynucleotide to increase, wherein diversity in the population is increased; and screening or selecting a population of variants for the desired functional property.

Another embodiment of the present invention provides a method of obtaining a polynucleotide encoding a desired functional property, comprising: preparing at least one heteroduplex polynucleotide; combining said heteroduplex polynucleotide with an effective amount of an agent or agents with exonuclease activity, polymerase activity and strand cleavage activity; allowing sufficient time for the percentage of complementarity between strands of the heteroduplex polynucleotide to increase, wherein diversity in the population is increased; converting DNA to RNA; and screening or selecting a population of ribonucleic acid variants for the desired functional property.

Yet another embodiment of the present invention provides a method of obtaining a polypeptide having a desired functional property, comprising: preparing at least one heteroduplex polynucleotide; combining said heteroduplex polynucleotide with an effective amount of an agent or agents with exonuclease activity, polymerase activity and strand cleavage activity; allowing sufficient time for the percentage of complementarity between strands of said heteroduplex polynucleotide to increase, converting said heteroduplex polynucleotide to RNA, and said RNA to a polypeptide; and screening or selecting a population of polypeptide variants for said desired functional property.

Still another embodiment of the present invention provides a method of obtaining a polynucleotide encoding a desired functional property, comprising: preparing at least one heteroduplex polynucleotide, where the heteroduplex is optionally, about 95%, 90%, 85%, 80%, or 75% identical, and about 1000 KB, 10,000 KB, or 100,000 KB is size; combining said heteroduplex polynucleotide with an effective amount of an agent or agents with exonuclease activity, polymerase activity and strand cleavage activity; allowing sufficient time for the percentage of complementarity between strands of the heteroduplex polynucleotide to increase, optionally screening or selecting for a population of variants having a desired functional property; denaturing said population of variants to obtain single strand polynucleotides; annealing said single strand polynucleotides to form at least one second heteroduplex polynucleotide; combining said second heteroduplex polynucleotide with an effective amount of an agent or agents with exonuclease activity, polymerase activity and strand cleavage activity; allowing sufficient time for the percentage of complementarity between strands of the heteroduplex polynucleotide to increase and optionally screening or selecting for a population of variants having a desired functional property. The second heteroduplex may be formed from the population of variants previously formed alone or with one or both single stranded parent polynucleotides or with an alternative single stranded polynucleotide.

The present invention is directed to a method for generating an improved polynucleotide sequence or a population of improved polynucleotide sequences, typically in the form of amplified and/or cloned polynucleotides, whereby the improved polynucleotide sequence(s) possess at least one desired phenotypic characteristic (e.g., encodes a polypeptide, promotes transcription of linked polynucleotides, binds a protein, improves the function of a viral vector, and the like) which can be selected or screened for. Such desired polynucleotides can be used in a number of ways such as expression from a suitable plant, animal, fungal, yeast, or bacterial expression vector, integration to form a transgenic plant, animal or microorganism, expression of a ribozyme, and the like.

GRAMMR provides for a process where heteroduplexed DNA strands are created by annealing followed by resolution of mismatches in an in vitro reaction. This reaction begins with cleavage of one strand or the other at or near a mismatch followed by excision of mismatched bases from that strand and polymerization to fill in the resulting gap with nucleotides that are templated to the sequence of the other strand. The resulting nick can be sealed by ligation to rejoin the backbone. The sum of the separate independent mismatch resolution events that occur throughout the heteroduplex molecule will result in reassortment of sequence information throughout that molecule. The sequence information will reassort in a variety of combinations to generate a complex library of sequence variants.

In one embodiment of GRAMMR, a library of mutants is generated by any method known in the art such as mutagenic PCR, chemical mutagenesis, etc. followed by screening or selection for mutants with a desired property. DNA is prepared from the chosen mutants. The DNAs of the mutants are mixed, denatured to single strands, and allowed to anneal. Partially complementary strands that hybridize will have non-base-paired nucleotides at the sites of the mismatches. Treatment with CEL I (Oleykowski et al., 1998; Yang et al., 2000), or a similar mismatch-directed activity, such as RES I, will cause nicking of one or the other polynucleotide strand 3' of each mismatch. (in addition, CEL I or RES I can nick 3' of an insertion/deletion resulting in reassortment of insertions/deletions.) The presence of a polymerase containing a 3'-to-5' exonuclease ("proofreading") activity (e.g., T4 DNA Pol) will allow excision of the mismatch, and subsequent 5'-to-3' polymerase activity will fill in the gap using the other strand as a template. A polymerase that lacks 5'-3' exonuclease activity and strand-displacement activity will fill in the gap and will cease to polymerize when it reaches the 5' end of DNA located at the original CEL I cleavage site, thus re-synthesizing only short patches of sequence. Alternatively, the length of the synthesized patches can be modulated by spiking the reaction with a polymerase that contains a 5'-3' exonuclease activity; this nick-translation activity can traverse a longer region resulting in a longer patch of information transferred from the template strand. DNA ligase (e.g., T4 DNA ligase) can then seal the nick by restoring the phosphate backbone of the repaired strand. This process can occur simultaneously at many sites and on either strand of a given heteroduplexed DNA molecule. The result is a randomization of sequence differences among input strands to give a population of sequence variants that is more diverse than the population of starting sequences. These output polynucleotides can be cloned directly into a suitable vector, or they can be amplified by PCR before cloning. Alternatively, the reaction can be carried out on heteroduplexed regions within the context of a double-stranded circular plasmid molecule or other suitable replicon that can be directly introduced into the appropriate host following the GRAMMR reaction. in another alternative, the output polynucleotides can be transcribed into RNA polynucleotides and used directly, for example, by inoculation of a plant viral vector onto a plant, such as in the instance of a viral vector transcription plasmid. The resulting clones are subjected to a selection or a screen for improvements in a desired property. The overall process can then be repeated one or more times with the selected clones in an attempt to obtain additional improvements.

If the output polynucleotides are cloned directly, there is the possibility of incompletely resolved molecules persisting that, upon replication in the cloning host, could lead to two different plasmids in the same cell. These plasmids could potentially give rise to mixed-plasmid colonies. If it is desired to avoid such a possibility, the output polynucleotide molecules can be grown in the host to allow replication/resolution, the polynucleotides isolated and retransformed into new host cells.

In another embodiment, when sequence input from more than two parents per molecule is desired, the above procedure is performed in a cyclic manner before any cloning of output polynucleotides. After GRAMMR treatment, the double stranded polynucleotides are denatured, allowed to anneal, and the mismatch resolution process is repeated. After a desired number of such cycles, the output polynucleotides can be cloned directly, introduced into a suitable vector, or they can be amplified by PCR before cloning. The resulting clones are subjected to a selection or a screen for improvements in a desired property.

In another embodiment, a "molecular backcross" is performed to help eliminate the background of deleterious mutations from the desired mutations. A pool of desired mutants' DNA can be mixed with an appropriate ratio of wild-type DNA to perform the method. Clones can be selected for improvement, pooled, and crossed back to wild-type again until there is no further significant change.

The efficiency of the process is improved by various methods of enriching the starting population for heteroduplex molecules, thus reducing the number of unaltered parental-type output molecules. The mismatched hybrids can be affinity purified using aptamers, dyes, or other agents that bind to mismatched DNA. A preferred embodiment is the use of MutS protein affinity matrix (Wagner et al., Nucleic Acids Res. 23(19): 3944-3948 (1995); Su et al., Proc. Natl. Acad. Sci. (U.S.A.), 83:5057-5061(1986)) or mismatch-binding but non-cleaving mutants of phage T4 endonuclease VII (Golz and Kemper, Nucleic Acids Research, 1999; 27: e7).

In one embodiment, the procedure is modified so that the input polynucleotides consist of a single strand of each sequence variant. For example, single-stranded DNAs of opposite strandedness are produced from the different parent sequences by asymmetric PCR to generate partially complementary single-stranded molecules. Annealing of the strands with one-another to make heteroduplex is performed as described in Example 1. Alternatively, single-stranded DNAs can be generated by preferentially digesting one strand of each parental double-stranded DNA with Lambda exonuclease followed by annealing the remaining strands to one-another. In this embodiment, the annealing strands have no 100% complementary strand present with which to re-anneal. Hence, there is a lower background of unmodified polynucleotides, that is, "parental polynucleotides" among the output polynucleotides leading to a higher efficiency of reasserting sequence variations. This increased efficiency will be particularly valuable in situations where a screen rather than a selection is employed to test for the desired polynucleotides.

Another method for heteroduplex formation is to mix the double-stranded parent DNAs, denature to dissociate the strands, and allow the single-stranded DNAs to anneal to one-another to generate a population of heteroduplexes and parental homoduplexes. The heteroduplexes can then be selectively enriched by a heteroduplex capture method such as those described above using MutS or a non-cleaving T4 endonuclease VII mutant. Alternatively, the parental homoduplex molecules in the population may be cleaved by restriction enzymes that overlap with sites of mismatch such that they are not cleaved in the heteroduplex but are cleaved in the parental homoduplex molecules. Uncleaved heteroduplex DNA can then be isolated by size fractionation in an agarose gel as was performed to generate full-length plasmid on full-length plasmid heteroduplex DNA molecules as describe in Example 6. Circularization of those full-length heteroduplexed plasmid molecules was then brought about by incubation with DNA ligase.

In another embodiment, the parental, or input, double-stranded polynucleotides are modified by the addition of "clamp" sequences. One input polynucleotide or pool of polynucleotides is amplified by PCR with the addition of a unique sequence in the 5' primer. The other input polynucleotide or pool is amplified by PCR with the addition of a unique sequence in the 3' primer. The clamp sequences can be designed to contain a unique restriction enzyme site for the 5' end of the gene of interest and another for the 3' end such that, at the step of cloning the products of the GRAMMR reassortment, only products with the 5' clamp from the first polynucleotide (or pool) and the 3' end from the second polynucleotide (or pool) will have appropriate ends for cloning. Alternatively, the products of GRAMMR reassortment can be PCR amplified using the unique sequences of the 5' and 3' clamps to achieve a similar result. Hence, there is a lower background of unmodified polynucleotides, that is, "parental polynucleotides" among the output polynucleotide clones leading to a higher efficiency of reasserting sequence variations. This increased efficiency will be particularly valuable in situations where a screen rather than a selection is employed to test for the desired polynucleotides. Optionally, oligonucleotide primers can be added to the GRAMMR reaction that are complementary to the clamp primer sequences such that either parent can serve as the top strand, thus permitting both reciprocal heteroduplexes to participate in the mismatch-resolution reaction.

Another method for generating cyclic heteroduplexed polynucleotides is performed where parental double-stranded DNAs have terminal clamp sequences as described above where the single-stranded clamp sequences extending from one end of the heteroduplex are complementary to single-stranded clamp sequences extending from the other end of the heteroduplex. These complementary, single-stranded clamps are allowed to anneal, thereby circularizing the heteroduplexed DNA molecule. Parental homoduplexes that result from re-annealing of identical sequences have only one clamp sequence and therefore, no complementary single-stranded sequences at their termini with which circularization can occur. Additionally, a DNA polymerase and a DNA ligase can be used to fill-in any gaps in the circular molecules and to seal the nicks in the backbone, respectively, to result in the formation of a population of covalently-closed circular heteroduplex molecules. As the covalently-closed circular heteroduplex molecules will not dissociate into their component strands if subjected to further denaturating conditions, the process of denaturation, circularization, and ligation can be repeated to convert more of the linear double-stranded parental duplexes into closed into closed circular heteroduplexes.

In another embodiment, a region of a single-stranded circular phagemid DNA can be hybridized to a related, but non-identical linear DNA, which can then be extended with a polymerase such as T7 DNA polymerase or T4 DNA polymerase plus T4 gene 32 protein, then ligated at the resulting nick to obtain a circular, double-stranded molecule with heteroduplexed regions at the sites of differences between the DNAs. GRAMMR can then be carried out on this molecule to obtain a library of sequence-reassorted molecules.

Alternately, two single-stranded circular phagemid DNAs of opposite strand polarity relative to the plasmid backbone, and parent gene sequences that are the target of the reassortment are annealed to one and other. A region of extensive mismatch will occur where the phage f1 origin sequences reside. Upon GRAMMR treatment, however, this region of extensive mismatch can revert to either parental type sequence restoring a function f1 origin. These double strained molecules will also contain mismatch regions at the sites of differences between the strands encoding the parent genes of interest. GRAMMR can then be carried out on this molecule to obtain a library of sequence re-assorted molecule.

As discussed in the preceding paragraphs, the starting DNA or input DNA can be of any number of forms. For example, input DNA can be full-length, single stranded and of opposite sense, as is taught in Example 1. Alternatively, the input DNA can also be a fragment of the full-length strand. The input DNAs can be double-stranded, either one or both, or modified, such as by, methylation, phosphorothiolate linkages, peptide-nucleic acid, substitution of RNA in one or both strands, or the like. Either strand of a duplex can be continuous along both strands, discontinuous but contiguous, discontinuous-with overlaps, or discontinuous with gaps.

GRAMMR can also be applied to DNA fragmentation and reassembly-based DNA shuffling schemes. For instance, in methods where gene fragments are taken through cycles of denaturation, annealing, and extension in the course of gene reassembly, GRAMMR can be employed as an intermediate step.

In one such embodiment, the DNA from a gene, or pool of mutants' genes is fragmented by enzymatic, mechanical or chemical means, and optionally a size range of said fragments is isolated by a means such as separation on an agarose gel. The starting polynucleotide, such as a wild-type, or a desired variant, or a pool thereof, is added to the fragments and the mixture is denatured and then allowed to anneal. The annealed polynucleotides are treated with a polymerase to fill in the single stranded gaps using the intact strand as a template. The resulting partially complementary double strands will have non-base-paired nucleotides at the sites of the mismatches. Treatment with CEL I (Oleykowski et al., 1998; Yang et al., 2000), or an agent with similar activity, such as RES I, will cause nicking of one or the other polynucleotide strand 3' of each mismatch. Addition of a polymerase containing a 3'-to-5' exonuclease that provides proofreading activity, such as, DNA Pol I, T4 DNA Pol I, will allow excision of the mismatch, and subsequent 5'-to-3' polymerase activity will fill in the gap using the other strand as a template. A DNA ligase, such as, T4 DNA Ligase, can then seal the nick by restoring the phosphate backbone of the repaired strand. The result is a randomization of sequence variation among input strands to give output strands with potentially improved properties. These output polynucleotides can be cloned directly into a suitable vector, or they can be amplified by PCR before cloning. The resulting clones are subjected to a selection or a screen for improvements in a desired property.

In one such embodiment, the DNA from a pool of mutants' genes is fragmented by enzymatic, mechanical or chemical means, or fragments are generated by limited extension of random oligonucleotides annealed to parental templates (U.S. Pat. No. 5,965,408), and optionally a size range of said fragments is isolated by a means such as separation on an agarose gel. The mixture is denatured and then allowed to anneal. The annealed polynucleotides are optionally treated with a polymerase to fill in the single stranded gaps. The resulting partially complementary double-strand fragments will have non-base paired nucleotides at the sites of the mismatches. Treatment with CEL I (Oleykowski et al., 1998; Yang et al., 2000), or an agent with similar activity, such as RES I, will cause nicking of one or the other polynucleotide strand 3' of each mismatch. The activity of a polymerase containing a 3'-to-5' exonuclease ("proofreading") activity, such as T4 DNA Polymerase, will allow excision of the mismatch, and subsequent 5'-to-3' polymerase activity will fill in the gap using the other strand as a template. Optionally, DNA ligase, such as, T4 DNA Ligase, can then seal the nick by restoring the phosphate backbone of the repaired strand. The result is a randomization of sequence variation among input strands to give output strands with potentially improved properties. Subsequent rounds of denaturing, annealing, and GRAMMR treatment allows gene reassembly. PCR can be used to amplify the desired portion of the reassembled gene. These PCR output polynucleotides can be cloned into a suitable vector. The resulting clones are subjected to a selection or a screen for the desired functional property.

Another embodiment of the present invention provides starting with a continuous scaffold strand to which fragments of another gene or genes anneal. The flaps and gaps are trimmed and filled as is described in Coco, et al., Nature Biotech 19 (01)354; U.S. Pat. No. 6,319,713, and GRAMMR is performed. In this process, GRAMMR would bring about further sequence reassortment by permitting transfer of sequence information between the template strand and the strand resulting from flap and gap trimming and ligation. This method provides the benefits of incorporating specific sequence patches into one continuous strand followed by GRAMMR of residues that mismatch with the scaffold. By annealing many fragments simultaneously to the same sequence or gene, many individual sites can be addressed simultaneously, thereby allowing reassortment of multiple sequences or genes at once. Unlike the method disclosed by Coco, et al., in the present embodiment, the scaffold is not degraded, rather the duplex can be directly cloned, or amplified by PCR prior to cloning. Exhaustive mismatch resolution will result in a perfectly duplexed DNA. Partial mismatch resolution will result in essentially two different reasserted products per duplex.

As can be appreciated from the present disclosure, GRAMMR can also be applied to a variety of methods that include the annealing of related DNAs as a step in their process. For example, many site-directed mutagenesis protocols call for the annealing of mutant-encoding DNA molecules to a circular DNA in single-stranded form, either phagemid or denatured plasmid. These DNAs are then extended with a polymerase, followed by treatment with ligase to seal the nick, with further manipulation to remove the parental sequence, leaving the desired mutation or mutations incorporated into the parental genetic background. Though these protocols are generally used to incorporate specific mutations into a particular DNA sequence, it is feasible that the GRAMMR process can be applied to the heteroduplexed molecules generated in such a process to reassort sequence variations between the two strands, thereby resulting in a diverse set of progeny with reasserted genetic variation.

Another embodiment provides for a sequential round of reassortment on a particular region. For example, DNA fragments are annealed to a circular single-strand phagemid DNA, and GRAMMR is performed. The fragments can be treated in order to prevent them from being physically incorporated into the output material. For example, they can be terminated at the 3' end with di-deoxy residues making them non-extendible. Multiple rounds of reassortment can be performed, but only modified molecules from the original input single stranded DNA clone will be recovered. The consequence will be that the DNA fragments used in this reassortment will contribute only sequence information to the final product and will not be physically integrated into the final recoverable product.

In instances where it is desired to resolve only sites of significant mismatch, that is patches of more than about 1 to 3 mismatches, S1 nuclease can be used. S1 nuclease is an endonuclease specific for single-stranded nucleic acids. If can recognize and cleave limited regions of mismatched base pairs in DNA:DNA or DNA:RNA duplexes. A mismatch of at least about 4 consecutive base pairs is generally required for recognition and cleavage by S1 nuclease. Mismatch resolution will not occur if both strands are cleaved, so the DNA must be repaired after the first nick and before the counter-nick. Other nucleases may be preferable for specifically tuning cleavage specificity according to sequence, sequence context, or size of mismatch.

In addition, other means of addressing mismatched residues, such as chemical cleavage of mismatches may be used. Alternatively, one can choose to subject the strands of heteroduplexed DNA to random nicking with an activity such as that exhibited by DNaseI or an agent that cleaves only in duplexed regions. If nick formation occurs in a region of identity between the two genes, the DNA ligase present in the reaction will seal the nick with no net transfer of sequence information. However, if nick formation occurs near a site of mismatch, the mismatched bases can be removed by 3'-5' exonuclease and the gap filled in by polymerase followed by nick sealing by ligase. Alternatively, application of nick-translation through regions of heterogeneity can bring about sequence reassortment. These processes, though not directed exclusively by the mismatch status of the DNA, will serve to transfer sequence information to the repaired strand, and thus result in a reasserted sequence.

GRAMMR can be used for protein, peptide, or aptamer display methods to obtain recombination between library members that have been selected. As fragmentation of the input DNAs is not required for GRAMMR, it may be possible to reassort sequence information between very small stretches of sequence. For instance, DNAs encoding small peptides or RNA aptamers that have been selected for a particular property such as target binding can be reasserted. For annealing to occur between the selected DNA molecules, some level of sequence homology should be shared between the molecules, such as at the 5' and 3' regions of the coding sequence, in regions of the randomized sequence segment that bear similarity because of similar binding activities, or through the biasing of codon wobble-base identity to a particular set of defaults.

Manipulation of the reaction temperature at which GRAMMR is conducted can be useful. For example, lower temperatures will help to stabilize heteroduplexes allowing GRAMMR to be performed on more highly mismatched substrates. Likewise, additives that affect base-pairing between strands, such as salts, PEG, formamide, etc, can be used to alter the stability of the heteroduplex in the GRAMMR, thereby affecting the outcome of the reaction.

In another embodiment, the mismatched double stranded polynucleotides are generated, treated with a DNA glycosylase to form an apurinic or apyrimidinic site, (that is an "AP site") an AP endonuclease activity to cleave the phosphodiester bond, deoxyribulose phosphodiesterase to remove the deoxyribose-phosphate molecules, DNA polymerase β or other DNA polymerase to add a single nucleotide to the 3' end of the DNA strand at the gap, and DNA ligase to seal the gap. The result is a reassortment of sequence variations between input strands to give output strands with potentially improved properties. These output polynucleotides can be cloned directly into a suitable vector, or they can be amplified by PCR before cloning. The resulting clones are subjected to a selection or a screen for improvements in a desired property.

Another embodiment provides for zonal mutagenesis by GRAMMR, that is, random or semi-random mutations at, and in the immediate vicinity of, mismatched residues using nucleotide analogues that have multiple base-pairing potential. This provides for concentration of essentially random mutagenesis at a particular point of interest, and adds another benefit to the present invention. Similar genes with slightly different functions, for example, plant R-genes, enzymes, or the like, will exhibit moderate sequence differences between them in regions that will be important for their own particular activities. Genes that express these activities, such as different substrates, binding partners, regulatory sites, or the like, should have heterogeneity in the regions that govern these functions. Since it is known that the specificity of such functions is associated with these amino acids and their neighbors, GRAMMR mutagenesis might serve to both reassort sequence variation among genes and also direct random mutagenesis to these regions to drive them further and faster evolutionarily, while not disturbing other sequences, such as structural framework, invariant residues, and other such important sites, that are potentially less tolerant to randomization.

Different enzymes with distinct functions will not differ just in the operative regions, such as active sites, regulatory sites, and the like. They are likely to have other differences from one another that arise through genetic drift. Further randomization in the locales of such changes might therefore be considered neutral, minimally important, or deleterious to the outcome of a mutagenesis experiment. In order to direct the random mutagenesis away from such inconsequential sites, and toward sites that might present a better result for random mutagenesis, such as the active site of an enzyme, the codon usage bias of the genes could be manipulated to decrease or increase the overall level of nucleotide complementarity in those regions. If regions of greater complementarity are less susceptible to GRAMMR than regions of lesser complementarity, then the degree of GRAMMER-directed zonal random mutagenesis at a given site can be modulated.

In another embodiment, after heteroduplex molecules are formed, an enzyme with a 3' to 5' exonuclease activity is added such that one strand of each end of the heteroduplex is digested back. At a point at which, on average, a desired amount of 3' to 5' digestion has occurred, dNTPs are added to allow the 5' to 3' polymerase activity from the same or an additional enzyme to restore the duplex using the opposite strand as a template. Thus mismatches in the digested regions are resolved to complementarity. Optionally, the resultant duplexes are purified, denatured and then allowed to anneal. The process of digestion, then polymerization is repeated resulting in new chimeric sequences. Additional cycles of the process can be performed as desired. Output duplex molecules are cloned and tested for the desired functional property. This process requires no fragmentation and reassembly. In addition, this process requires no endonucleolytic cleavages.

In another embodiment, after the heteroduplex molecules are formed, an enzyme with a 5' to 3' exonuclease activity, such as, T7 Gene6 Exonuclease as disclosed in Enger, M J and Richardson, C C, J Biol Chem 258(83)11197), is added such that one strand of each end of the heteroduplex is digested. At a point at which, on average, a desired amount of 5' to 3' digestion has occurred, the reaction is stopped and the exonuclease inactivated. Oligonucleotide primers complementary to the 5' and 3' ends of the target polynucleotides are added and annealed. A DNA polymerase, such as, T4 DNA Polymerase, a DNA ligase and dNTPs are added to allow the 5' to 3' polymerase activity to extend the primers and restore the duplex using the opposite strand as a template, with ligase sealing the nick. Thus mismatches in the digested regions are resolved to complementarity. Optionally, the resultant duplexes are purified, denatured and then allowed to anneal. The process of digestion then polymerization is repeated resulting in new chimeric sequences. Additional cycles of the process can be performed as desired. Output duplex molecules are cloned and tested for the desired functional property. This process requires no fragmentation and reassembly. in addition, this process requires no endonucleolytic cleavages.

In any DNA shuffling experiment, it is desirable to minimize the proportion of non-shuffled, or parental, DNAs that are obtained within the population of shuffled progeny. Numerous approaches may be used to accomplish this. In a plasmid-on-plasmid DNA shuffling format, where the genes to be shuffled are present on separate, but otherwise identical plasmids, each plasmid is linearized by one or another different unique restriction sites that are present. After removal of the restriction endonucleases, the linearized DNAs are mixed, melted apart, and allowed to anneal so that populations of heteroduplex DNA form that are either nicked, closed circular heteroduplex molecules, or are double stranded and linear homoduplexes. If is the population of circular double-stranded heteroduplex DNA molecules that represents the desired substrate for the GRAMMR reaction. One can either enrich this desired population by gel fractionation or use one or a number of methods that do not require physical separation of this population, but rather, discourages the recovery of non-shuffled parental molecules. Several such methods are listed below.

First, after GRAMMR treatment of the mixed population of linear parental homoduplex and circular double-stranded heteroduplex, transformation of E. coli is generally performed. Since circular DNA is vastly more efficient at transforming E. coli than its linearized counterpart, the parental homoduplexes can be strongly discriminated against at this step by preventing their circularization into transformation-competent molecules. The use of E. coli DNA ligase as the ligase component of the GRAMMR reaction will serve to prevent recircularization of parental homoduplex, as it more efficiently seals nicks than joins short cohesive termini that result from restriction endonuclease cleavage. Additionally, blunt ends are very inefficiently ligated by this enzyme. As a result of using this strategy, the progeny resulting from transformation of E. coli with the GRAMMR reaction are depleted of non-shuffled parental genes and enriched for molecules that entered the GRAMMR reaction as heteroduplex substrates.

Another method for excluding parental gene contamination from the population of GRAMMR progeny is to position the plasmid linearization sites within a selectable marker. The sites should be of sufficient distance from one another to allow annealing to take place between staggered ends of a heteroduplex, and should either have overhangs that can be filled-in or trimmed off, or cause a deletion of sequence upon cleavage. As above, the plasmids containing the genes to be shuffled are linearized at one or other of the sites. After removal of the restriction endonucleases, the linearized DNAs are mixed, melted, and allowed to anneal. The resulting sample is made up of a mixture of circular heteroduplexes and of linear homoduplexes. This sample can then be treated with a polymerase/exonuclease such as T4 DNA polymerase In the presence of dNTPs. The circular homoduplexes should be unaffected, whereas the linear parental homoduplexes will have been blunted at their termini, effectively adding or deleting bases to the sequence of the selectable marker if that molecule becomes recircularized at any point in the GRAMMR reaction or after transformation into E. coli. If the addition or deletion of these sequences results in disruption of the function of the selectable marker, then the resulting molecules will not be recovered under appropriate selection.

Another method one can use to prevent unshuffled parental contamination of the shuffled library is to dephosphorylate the linearized DNAs prior to melting and annealing. Linear homoduplex molecules will be rendered unable to ligate into circular molecules whereas circular heteroduplexes will simply contain a single nick in each strand, but will still remain circular, and thus competent for transformation into E. coli.

Another method one can use to prevent unshuffled parental contamination of the shuffled library is to digest with enzymes whose recognition sites are overlapped by mismatches in the heteroduplexed molecules. Digestion of the parental homoduplexes at those sites will render the resulting molecules linear so that they may be subject to any of the treatments described above to reduce parental contamination. The resulting molecules may also be made smaller, facilitating separation from the intact circular heteroduplex molecules.

If, in addition to excluding unshuffled parental molecules from a shuffling experiment, one desires to prevent shuffling between any two or more genes of a population of two or more parent genes, the same principles described above can be applied.

In the current invention the random reassortment occurs in an in vitro DNA mismatch-resolution reaction. This method does not require any steps of "gene reassembly" that serve as the foundation for the earlier mutation reassortment ("shuffling") methods. Instead, it is based upon the ability of a reconstituted or artificial DNA mismatch resolving system to transmit sequence variations from one or more strands of DNA into another DNA strand by hybridization and mismatch resolution in vitro.

In general, standard techniques of recombinant DNA technology are described in various publications, e.g., (Ausubel, 1987; Ausubel, 1999; Sambrook et al., 1989), each of which is incorporated herein in their entirety by reference. Polynucleotide modifying enzymes were used according to the manufacturers recommendations. if desired, PCR amplimers for amplifying a predetermined DNA sequence may be chosen at the discretion of the practitioner.

It is noted that each of the activities taught in the present invention that are involved in the GRAMMR reaction can be interchanged with a functional equivalent agent with similar activity, and that such changes are within the scope of the present invention. For instance, as was indicated in Example 2, Taq DNA ligase could substitute for T4 DNA ligase. Other ligases can be substituted as well, such as E. coli DNA ligase. Likewise, as shown in Examples 2 and 8, respectively, Pfu polymerase and T7 DNA polymerase can be substituted for T4 DNA polymerase. Other enzymes with appropriate exonuclease activity with or without associated polymerase can function in place of any of these enzymes for the exonuclease activity needed for the GRAMMR reaction. In a similar way, any polymerase with functionally equivalent activity to those demonstrated to work for GRAMMR can be used for substitution. These include E. coli Pol I, the Klenow fragment of E. coli Pol i, polymerase beta, among many others.

Strand cleavage may be brought about in a number of ways. In addition to CEL I, a number of functionally equivalent, and potentially homologous activities found in extracts from a variety of plant species (Oleykowski, Nucleic Acids Res 1998;26:4597-602) may be used. Other mismatch-directed endonucleases such as T4 endonuclease VII, T7 endonuclease I, and SP nuclease (Oleykowski, Biochemistry 1999; 38: 2200-5) may be used. Another particularly useful mismatch-directed endonuclease Is RES I. Other nucleases which attack single stranded DNA can be used, such as S1 nuclease, FEN1, cleavase, mung bean nuclease, and nuclease P1. Enzymes that make random cleavage events in DNA, such as pancreatic DNase I may also be substituted for the strand cleaving activity in GRAMMR. A number of methods for bringing about strand cleavage through other means are also envisioned. These include potassium permanganate used with tetraethylammonium acetate, the use of sterically bulky photoactivatable DNA intercalators such as [Rh(bpy)2 (chrysi)]3+, osmium tetroxide with piperidine alkaloid, and hydroxylamine with piperidine alkaloid, as well as the use of radiation energy to bring about strand breakage.

Another embodiment to the present invention is directed to recombinant plant viral nucleic acids and recombinant viruses which are stable for maintenance and transcription or expression of non-native (foreign) nucleic acid sequences and which are capable of systemically transcribing or expressing such foreign sequences in the host plant. More specifically, recombinant plant viral nucleic acids according to the present invention comprise a native plant viral subgenomic promoter, at least one non-native plant viral subgenomic promoter, a plant viral coat protein coding sequence, and optionally, at least one non-native, nucleic acid sequence.

The present invention provides nucleic acid molecules comprising a nucleic acid sequence selected from the group consisting of SEQ ID NO:01, SEQ ID NO:02, SEQ ID NO:03, or SEQ ID NO:04, useful as vectors or plasmids for the expression of CEL I endonuclease.

The nucleic acid molecules of SEQ ID NO:03, and SEQ ID NO:04 are CEL I open reading frames contained within SEQ ID NO:01 and SEQ ID NO:02, respectively. The nucleic acid molecules, SEQ ID NO:01 and SEQ ID NO:02 were deposited with the American Type Culture Collection, Manassas, Va. 20110-2209 USA. The deposits were received and accepted on Dec. 13, 2001, and assigned the following Patent Deposit Designation numbers, PTA-3926 (SEQ ID NO:01), and PTA-3927 (SEQ ID NO:02). The preparation and use of the nucleic acid molecules of SEQ ID NO:01, SEQ ID NO:02, SEQ ID NO:03 and SEQ ID NO:04, are further taught in Example 12 herein.

The present invention also provides nucleic acid molecules comprising the nucleic acid sequence of FIG. 3 (SEQ ID NO: 16), useful as vectors or plasmids for the expression of RES I endonuclease.

The nucleic acid molecule of FIG. 3 (SEQ ID NO: 16) was deposited with the American Type Culture Collection, Manassas, Va. 20110-2209 USA. The deposit was received on Jul. 30, 2002 and accepted on Aug. 29, 2002, and assigned the following Patent Deposit Designation number, PTA-4562. The preparation and use of the nucleic acid molecule of FIG. 3 (SEQ ID NO: 16) is further taught in Example 13 herein.

The present invention further provides a plant cell comprising a vector or plasmid comprising of a nucleic acid sequence selected from the group consisting of SEQ ID NO:01, SEQ ID NO:02, SEQ ID NO:03, SEQ ID NO:04, or FIG. 3 (SEQ ID NO: 16) where the plant cell is a host cell, or production cell.

These deposits were made in accordance with the terms and provisions of the Budapest Treaty relating to deposit of microorganisms and was made for a term of at least thirty (30) years and at least five (05) years after the most recent request for the furnishing of a sample of the deposit is received by the depository, or for the effective term of a patent to issue from this application or a subsequent application citing any of these deposits, whichever is longer. Each deposit will be replaced if it becomes non-viable during that period. The applicant upon the granting of the patent will irrevocably remove all restrictions on the accessibility of the deposited biological material.

The present invention also provides a process for expressing CEL I or RES I endonuclease using a recombinant plant viral nucleic acid comprising of a nucleic acid sequence selected from the group consisting of SEQ ID NO:01, SEQ ID NO:02, SEQ ID NO:03, SEQ ID NO:04, or FIG. 3 (SEQ ID NO: 16).

The present invention also provides a process for expressing CEL I or RES I endonuclease using a recombinant plant viral nucleic acid comprising of a nucleic acid sequence selected from the group consisting of SEQ ID NO: 01, SEQ ID NO: 02, SEQ ID NO: 03, SEQ ID NO: 04, or FIG. 3 (SEQ ID NO: 16)

In another embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a fusion protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In another embodiment, a recombinant plant viral nucleic acid is provided as in the first embodiment except that the native coat protein coding sequence is placed adjacent one of the non-native coat protein subgenomic promoters instead of a non-native coat protein coding sequence.

In yet another embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In another embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) in the host to produce the desired product.

As used herein, the term "host" refers to a cell, tissue or organism capable of replicating a vector or plant viral nucleic acid and which is capable of being infected by a virus containing the viral vector or plant viral nucleic acid. This term is intended to include procaryotic and eukaryotic cells, organs, tissues or organisms, where appropriate.

As used herein, the term "infection" refers to the ability of a virus to transfer its nucleic acid to a host or introduce viral nucleic acid into a host, wherein the viral nucleic acid is replicated, viral proteins are synthesized, and new viral particles assembled. In this context, the terms "transmissible" and "infective" are used interchangeably herein.

As used herein, the term "non-native" refers to any RNA sequence that promotes production of subgenomic mRNA including, but not limited to, 1) plant viral promoters such as ORSV and vrome mosaic virus, 2) viral promoters from other organisms such as human sindbis viral promoter, and 3) synthetic promoters.

As used herein, the term "phenotypic trait" refers to an observable property resulting from the expression of a gene.

As used herein, the term "plant cell" refers to the structural and physiological unit of plants, consisting of a protoplast and the cell wall.

As used herein, the term "plant Organ" refers to a distinct and visibly differentiated part of a plant, such as root, stem, leaf or embryo.

As used herein, the term "plant tissue" refers to any tissue of a plant in planta or in culture. This term is intended to include a whole plant, plant cell, plant organ, protoplast, cell culture, or any group of plant cells organized into a structural and functional unit.

As used herein, the term "production cell" refers to a cell, tissue or organism capable of replicating a vector or a viral vector, but which is not necessarily a host to the virus. This term is intended to include prokaryotic and eukaryotic cells, organs, tissues or organisms, such as bacteria, yeast, fungus and plant tissue.

As used herein, the term "promoter" refers to the 5'-flanking, non-coding sequence adjacent a coding sequence which is involved in the initiation of transcription of the coding sequence.

As used herein, the term "protoplast" refers to an isolated plant cell without cell walls, having the potency for regeneration into cell culture or a whole plant.

As used herein, the term "recombinant plant viral nucleic acid" refers to plant viral nucleic acid which has been modified to contain non-native nucleic acid sequences.

As used herein, the term "recombinant plant virus" refers to a plant virus containing the recombinant plant viral nucleic acid.

As used herein, the term "subgenomic promoter" refers to a promoter of a subgenomic mRNA of a viral nucleic acid.

As used herein, the term "substantial sequence homology" refers to nucleotide sequences that are substantially functionally equivalent to one another. Nucleotide differences between such sequences having substantial sequence homology will be de minimus in affecting function of the gene products or an RNA coded for by such sequence.

As used herein, the term "transcription" refers to production of an RNA molecule by RNA polymerase as a complementary copy of a DNA sequence.

As used herein, the term "vector" refers to a self-replicating DNA molecule which transfers a DNA segment between cells.

As used herein, the term "virus" refers to an infectious agent composed of a nucleic acid encapsidated in a protein. A virus may be a mono-, di-, tri- or multi-partite virus, as described above.

The present invention provides for the infection of a plant host by a recombinant plant virus containing recombinant plant viral nucleic acid or by the recombinant plant viral nucleic acid which contains one or more non-native nucleic acid sequences which are transcribed or expressed in the infected tissues of the plant host. The product of the coding sequences may be recovered from the plant or cause a phenotypic trait in the plant.

The present invention has a number of advantages, one of which is that the transformation and regeneration of target organisms is unnecessary. Another advantage is that it is unnecessary to develop vectors which integrate a desired coding sequence in the genome of the target organism. Existing organisms can be altered with a new coding sequence without the need of going through a germ cell. The present invention also gives the option of applying the coding sequence to the desired organism, tissue, organ or cell. Recombinant plant viral nucleic acid is also stable for the foreign coding sequences, and the recombinant plant virus or recombinant plant viral nucleic acid is capable of systemic infection in the plant host.

An important feature of the present invention is the preparation of recombinant plant viral nucleic acids (RPVNA) which are capable of replication and systemic spread in a compatible plant host, and which contain one or more non-native subgenomic promoters which are capable of transcribing or expressing adjacent nucleic acid sequences in the plant host. The RPVNA may be further modified to delete all or part of the native coat protein coding sequence and to contain a non-native coat protein coding sequence under control of the native or one of the non-native subgenomic promoters, or put the native coat protein coding sequence under the control of a non-native plant viral subgenomic promoter. The RPVNA have substantial sequence homology to plant viral nucleotide sequences. A partial listing of suitable viruses are described herein. The nucleotide sequence may be an RNA, DNA, cDNA or chemically synthesized RNA or DNA.

The first step in achieving any of the features of the invention is to modify the nucleotide sequences of the plant viral nucleotide sequence by known conventional techniques such that one or more non-native subgenomic promoters are inserted into the plant viral nucleic acid without destroying the biological function of the plant viral nucleic acid. The subgenomic promoters are capable of transcribing or expressing adjacent nucleic acid sequences in a plant host infected by the recombinant plant viral nucleic acid or recombinant plant virus. The native coat protein coding sequence may be deleted in two embodiments, placed under the control of a non-native subgenomic promoter in a second embodiment, or retained in a further embodiment. If it is deleted or otherwise inactivated, a non-native coat protein gene is inserted under control of one of the non-native subgenomic promoters, or optionally under control of the native coat protein gene subgenomic promoter. The non-native coat protein is capable of encapsidating the recombinant plant viral nucleic acid to produce a recombinant plant virus. Thus, the recombinant plant viral nucleic acid contains a coat protein coding sequence, which may be native or a normative coat protein coding sequence, under control of one of the native or non-native subgenomic promoters. The coat protein is involved in the systemic infection of the plant host.

Some of the viruses which meet this requirement, and are therefore suitable, include viruses from the tobacco mosaic virus group such as Tobacco Mosaic virus (TMV), Cowpea Mosaic virus (CMV), Alfalfa Mosaic virus (AMV), Cucumber Green Mottle Mosaic virus watermelon strain (CGMMV-W) and Oat Mosaic virus (OMV) and viruses from the brome mosaic virus group such as Brome Mosaic virus (MBV), broad bean mottle virus and cowpea chlorotic mottle virus. Additional suitable viruses include Rice Necrosis virus (RNV), and geminiviruses such as tomato golden mosaic virus (TGMV), Cassava latent virus (CLV) and maize streak virus (MSV). Each of these groups of suitable viruses is characterized below.

Tobacco Mosaic Virus Group

Tobacco Mosaic virus (TMV) is a member of the Tobamoviruses. The TMV virion is a tubular filament, and comprises coat protein sub-units arranged in a single right-handed helix with the single-stranded RNA intercalated between the turns of the helix. TMV infects tobacco as well as other plants. TMV is transmitted mechanically and may remain infective for a year or more in soil or dried leaf tissue.

The TMV virions may be inactivated by subjection to an environment with a pH of less than 3 or greater than 8, or by formaldehyde or iodine. Preparations of TMV may be obtained from plant tissues by $(NH_4)_2SO_4$ precipitation, followed by differential centrifugation.

The TMV single-stranded RNA genome is about 6400 nucleotides long, and is capped at the 5' end but not polyadenylated. The genomic RNA can serve as mRNA for a protein of a molecular weight of about 130,000 (130K) and another produced by read-through of molecular weight about 180,000 (180K). However, it cannot function as a messenger for the synthesis of coat protein. Other genes are expressed during infection by the formation of monocistronic, 3'-coterminal sub-genomic mRNAs, including one (LMC) encoding the 17.5K coat protein and another (I2) encoding a 30K protein. The 30K protein has been detected in infected protoplasts (16), and it is involved in the cell-to-cell transport of the virus in an infected plant (17). The functions of the two large proteins are unknown.

Several double-stranded RNA molecules, including double-stranded RNAs corresponding to the genomic, 12 and LMC RNAs, have been detected in plant tissues infected with TMV. These RNA molecules are presumably intermediates in genome replication and/or mRNA synthesis processes which appear to occur by different mechanisms.

TMV assembly apparently occurs in plant cell cytoplasm, although it has been suggested that some TMV assembly may occur in chloroplasts since transcripts of ctDNA have been detected in purified TMV virions. initiation of TMV assembly occurs by interaction between ring-shaped aggregates ("discs") of coat protein (each disc consisting of two layers of 17 subunits) and a unique internal nucleation site in the RNA; a hairpin region about 900 nucleotides from the 3' end in the common strain of TMV. Any RNA, including subgenomic RNAs containing this site, may be packaged into virions. The discs apparently assume a helical form on interaction with the RNA, and assembly (elongation) then proceeds in both directions (but much more rapidly in the 3'- to 5'-direction from the nucleation site).

Another member of the Tobamoviruses, the Cucumber green mottle mosaic virus watermelon strain (CGMMV-W) is related to the cucumber virus, Noru, Y. et al., Virology 45:577 (1971). The coat protein of CGMMV-W interacts with RNA of both TMV and CGMMV to assemble viral particles in vitro, Kurisu et al., Virology 70:214 (1976).

Several strains of the tobamovirus group are divided into two subgroups, on the basis of the location of the assembly of origin, Fukuda, M. et al., Proc. Nat. Acad. Sci. USA 78:4231 (1981). Subgroup i, which includes the vulgare, OM, and tomato strain, has an origin of assembly about 800-1000 nucleotides from the 3' end of the RNA genome, and outside the coat protein cistron, Lebeurier, G. et al., Proc. Nat. Acad. Sci. USA 74:1913 (1977); and Fukuda, M. et al., Virology 101:493 (1980). Subgroup ii, which includes CGMMV-W and cornpea strain (Cc) has an origin of assembly about 300-500 nucleotides from the 3' end of the RNA genome and within the coat-protein cistron, Fukuda, M. et al., Virology 101:493 (1980). The coat protein cistron of CGMMV-W is located at nucleotides 176-661 from the 3' end. The 3' non-coding region is 175 nucleotides long. The origin of assembly is positioned within the coat protein cistron, Meshi, T. et al., Virology 127:52 (1983).

Brome Mosaic Virus Group

Brome mosaic virus (BV) is a member of a group of tripartite, single-stranded, RNA-containing plant viruses commonly referred to as the bromoviruses. Each member of the bromoviruses infects a narrow range of plants. Mechanical transmission of bromoviruses occurs readily, and some members are transmitted by beetles. In addition to BV, other bromoviruses include broad bean mottle virus and cowpea chlorotic mottle virus.

Typically, a bromovirus virion is icosahedral, with a diameter of about 26 mm, containing a single species of coat protein. The bromovirus genome has three molecules of linear, positive-sense, single-stranded RNA, and the coat protein mRNA is also encapsidated. The RNAs each have a capped 5' end, and a tRNA-like structure (which accepts tyrosine) at the 3' end. Virus assembly occurs in the cytoplasm. The complete nucleotide sequence of BMV has been identified and characterized as described by Alquist et al., J. Mol. Biol. 153:23 (1981).

Rice Necrosis Virus

Rice Necrosis virus is a member of the Potato Virus Y Group or Potyviruses. The Rice Necrosis virion is a flexuous filament comprising one type of coat protein (molecular weight about 32,000 to about 36,000) and one molecule of linear positive-sense single-stranded RNA. The Rice Necrosis virus is transmitted by *Polvmvxa araminis* (a eukaryotic intracellular parasite found in plants, algae and fungi).

Geminiviruses

Geminiviruses are a group of small, single-stranded DNA-containing plant viruses with virions of unique morphology. Each virion consists of a pair of isometric particles (incomplete icosahedra), composed of a single type of protein (with a molecular weight of about $2.7-3.4 \times 10^4$). Each geminivirus virion contains one molecule of circular, positive-sense, single-stranded DNA. In some geminiviruses (i.e., Cassava latent virus and bean golden mosaic virus) the genome appears to be bipartite, containing two single-stranded DNA molecules.

The nucleic acid of any suitable plant virus can be utilized to prepare the recombinant plant viral nucleic acid of the present invention. The nucleotide sequence of the plant virus is modified, using conventional techniques, by the insertion of one or more subgenomic promoters into the plant viral nucleic acid. The subgenomic promoters are capable of functioning in the specific host plant. For example, if the host is tobacco, TMV will be utilized. The inserted subgenomic promoters must be compatible with the TMV nucleic acid and capable of directing transcription or expression of adjacent nucleic acid sequences in tobacco.

The native coat protein gene could also be retained and a non-native nucleic acid sequence inserted within it to create a fusion protein as discussed below. in this example, a non-native coat protein gene is also utilized.

The native or non-native coat protein gene is utilized in the recombinant plant viral nucleic acid. Whichever gene is utilized may be positioned adjacent its natural subgenomic promoter or adjacent one of the other available subgenomic promoters. The non-native coat protein, as is the case for the native coat protein, is capable of encapsidating the recombinant plant viral nucleic acid and providing for systemic spread of the recombinant plant viral nucleic acid in the host plant. The coat protein is selected to provide a systemic infection in the plant host of interest. For example, the TMV-O coat protein provides systemic infection in *N. benthamiana*, whereas TMV-U1 coat protein provides systemic infection in *N. tabacum.*

The recombinant plant viral nucleic acid is prepared by cloning viral nucleic acid in an appropriate production cell. If the viral nucleic acid is DNA, it can be cloned directly into a suitable vector using conventional techniques. One technique is to attach an origin of replication to the viral DNA which is compatible with the production cell. If the viral nucleic acid is RNA, a full-length DNA copy of the viral genome is first prepared by well-known procedures. For example, the viral RNA is transcribed into DNA using reverse transcriptase to produce subgenomic DNA pieces, and a double-stranded DNA made using DNA polymerases. The DNA is then cloned into appropriate vectors and cloned into a production cell. The DNA pieces are mapped and combined in proper sequence to produce a full-length DNA copy of the viral RNA genome, if necessary. DNA sequences for the subgenomic promoters, with or without a coat protein gene, are then inserted into the nucleic acid at non-essential sites, according to the particular embodiment of the invention utilized. Non-essential sites are those that do not affect the biological properties of the plant viral nucleic acid. Since the RNA genome is the infective agent, the cDNA is positioned adjacent a suitable promoter so that the RNA is produced in the production cell. The RNA is capped using conventional techniques, if the capped RNA is the infective agent.

Another embodiment of the present invention is a recombinant plant viral nucleic acid which further comprises one or more non-native nucleic acid sequences capable of being transcribed in the plant host. The non-native nucleic acid sequence is placed adjacent one or the non-native viral subgenomic promoters and/or the native coat protein gene promoter depending on the particular embodiment used. The non-native nucleic acid is inserted by conventional techniques, or the non-native nucleic acid sequence can be inserted into or adjacent the native coat protein coding sequence such that a fusion protein is produced. The non-native nucleic acid sequence, which is transcribed, may be transcribed as an RNA capable of regulating the expression of a phenotypic trait by an anti-sense mechanism. Alternatively, the non-native nucleic acid sequence in the recombinant plant viral nucleic acid may be transcribed and translated in the plant host, to produce a phenotypic trait. The non-native nucleic acid sequence(s) may also code for the expression of more than one phenotypic trait. The recombinant plant viral nucleic acid containing the non-native nucleic acid sequence is constructed using conventional techniques such that non-native nucleic acid sequence(s) are in proper orientation to whichever viral subgenomic promoter is utilized.

Useful phenotypic traits in plant cells include, but are not limited to, improved tolerance to herbicides, improved tolerance to extremes of heat or cold, drought, salinity or osmotic stress; improved resistance to pests (insects, nematodes or arachnids) or diseases (fungal, bacterial or viral) production of enzymes or secondary metabolites; male or female sterility; dwarfness; early maturity; improved yield, vigor, heterosis, nutritional qualities, flavor or processing properties, and the like. Other examples include the production of important proteins or other products for commercial use, such as lipase, melanin, pigments, antibodies, hormones, pharmaceuticals, antibiotics and the like. Another useful phenotypic trait is the production of degradative or inhibitory enzymes, such as are utilized to prevent or inhibit root development in malting barley. The phenotypic trait may also be a secondary metabolite whose production is desired in a bioreactor.

A double-stranded DNA of the recombinant plant viral nucleic acid or a complementary copy of the recombinant plant viral nucleic acid is cloned into a production cell. If the viral nucleic acid is an RNA molecule, the nucleic acid (cDNA) is first attached to a promoter, which is compatible with the production cell. The RPVNA can then be cloned into any suitable vector, which is compatible with the production cell. In this manner, only RNA copies of the chimeric nucleotide sequence are produced in the production cell. For example, if the production cell is *E. coli*, the lac promoter can be utilized. If the production cell is a plant cell, the CaMV promoter can be used. The production cell can be a eukaryotic cell such as yeast, plant or animal, if viral RNA must be capped for biological activity. Alternatively, the RPVNA is inserted in a vector adjacent a promoter, which is compatible with the production cell. If the viral nucleic acid is a DNA molecule, it can be cloned directly into a production cell by attaching it to an origin of replication which is compatible with the production cell. In this manner, DNA copies of the chimeric nucleotide sequence are produced in the production cell.

A promoter is a DNA sequence that directs RNA polymerase to bind to DNA and to initiate RNA synthesis. There are strong promoters and weak promoters. Among the strong promoters are lacuv5, trp, tac, trp-lacuv5, λp1, ompF, and bla. A useful promoter for expressing foreign genes in *E. coli* is one which is both strong and regulated. The λp1 promoter of bacteriophage λ is a strong, well-regulated promoter, Hedgpeth, J. M. et al., Mol. Gen. Genet. 163:197 (1978); Bernard, H. M. et al., Gene 5:59 (1979); Remaut, E. P. et al., Gene 15:81 (1981).

A gene encoding a temperature-sensitive λ repressor such as λcIts 857 may be included in the cloning vector, Bernard, H. M. et al., Gene 5:59 (1979). At low temperature (31° C.), the p1 promoter is maintained in a repressed state by the cI-gene product. Raising the temperature destroys the activity of the repressor. The p1 promoter then directs the synthesis of large quantities of mRNA. In this way, *E. coli* production cells may grow to the desired concentration before producing the products encoded within the vectors. Similarly, a temperature-sensitive promoter may be activated at the desired time by adjusting the temperature of the culture.

It may be advantageous to assemble a plasmid that can conditionally attain very high copy numbers. For example, the pAS2 plasmid containing a lac or tac promoter will achieve very high copy numbers at 42° C. The lac repressor, present in the pAS2 plasmid, is then inactivated by isopropyl-β-D-thiogalactoside to allow synthesis of mRNA.

A further alternative when creating the RPVNA is to prepare more than one nucleic acid (i.e., to prepare the nucleic acids necessary for a multipartite viral vector construct). In this case, each nucleic acid would require its own origin of assembly. Each nucleic acid could be prepared to contain a subgenomic promoter and a non-native nucleic acid.

Alternatively, the insertion of a non-native nucleic acid into the nucleic acid of a monopartite virus may result in the creation of two nucleic acids (i.e., the nucleic acid necessary for the creation of a bipartite viral vector). This would be advantageous when it is desirable to keep the replication and transcription, or expression of the non-native nucleic acid separate from the replication and translation of some of the coding sequences of the native nucleic acid. Each nucleic acid would have to have its own origin of assembly.

A third feature of the present invention is a virus or viral particle. The virus comprises a RPVNA as described above which has been encapsidated. The resulting product is then capable of infecting an appropriate plant host. The RPVNA sequence is transcribed and/or translated within the plant host to produce the desired product.

In one embodiment of the present invention, the recombinant plant viral nucleic acid is encapsidated by a heterologous capsid. Most commonly, this embodiment will make use of a rod-shaped capsid because of its ability to encapsidate a longer RPVNA than the more geometrically constrained icosahedral capsid or spherical capsid. The use of a rod-shaped capsid permits incorporation of a larger non-native nucleic acid to form the RPVNA. Such a rod-shaped capsid is most advantageous when more than one non-native nucleic acid is present in the RPVNA.

Another feature of the invention is a vector containing the RPVNA as described above. The RPVNA is adjacent a nucleotide sequence selected from the group consisting of a production cell promoter or an origin of replication compatible with the production cell. The vector is utilized to transform a production cell, which will then produce the RPVNA in quantity. The production cell may be any cell, which is compatible with the vector, and may be prokaryotic or eukaryotic. However, if the viral RNA (RPVNA) must be capped in order to be active, the production cell must be capable of capping the viral RNA, such as a eukaryotic production cell.

A further feature of the present invention is a host, which has been infected by the recombinant plant virus or viral nucleic acid. After introduction into a host, the host contains the RPVNA which is capable of self-replication, encapsidation and systemic spread. The host can be infected with the recombinant plant virus by conventional techniques. Suitable techniques include, but are not limited to, leaf abrasion, abrasion in solution, high velocity water spray and other injury of a host as well as imbibing host seeds with water containing the recombinant plant virus. More specifically, suitable techniques include:

(a) Hand Inoculations.

Hand inoculations of the encapsidated vector are performed using a neutral pH, low molarity phosphate buffer, with the addition of celite or carborundum (usually about 1%) One to four drops of the preparation is put onto the upper surface of a leaf and gently rubbed.

(b) Mechanized Inoculations of Plant Beds.

Plant bed inoculations are performed by spraying ($CO_2$-propelled) the vector solution into a tractor-driven mower while cutting the leaves. Alternatively, the plant bed is mowed and the vector solution sprayed immediately onto the cut leaves.

(c) High Pressure Spray of Single Leaves.

Single plant inoculations can also be performed by spraying the leaves with a narrow, directed spray (50 psi, 6-12 inches from the leaf) containing approximately 1% carborundum in the buffered vector solution.

An alternative method for introducing a RPVNA into a plant host is a technique known as agroinfection or Agrobacterium-mediated transformation (sometimes called Agro-infection) as described by Grimsley, N. et al., Nature 325:177 (1987). This technique makes use of a common feature of Agrobacterium which colonizes plants by transferring a portion of their DNA (the T-DNA) into a host cell, where it becomes integrated into nuclear DNA. The T-DNA is defined by border sequences which are 25 base pairs long, and any DNA between these border sequences is transferred to the plant cells as well. The insertion of a RPVNA between the T-DNA border sequences results in transfer of the RPVNA to the plant cells, where the RPVNA is replicated, and then spreads systemically through the plant. Agro-infection has been accomplished with potato spindle tuber viroid (PSTV) (Gardner, R. C. et al., Plant Mol. Biol. 6:221 (1986)); CaV (Grimsley, N. et al., Proc. Nat. Acad. Sci. USA 83:3282 (1986)); MSV (Grimsley, N. et al., Nature 325:177 (1987)) and Lazarowitz, S. C., Nucl. Acids Res. 16:22 (1988)), digitaria streak virus (Donson, J. et al., Virology 162:248 (1988)), wheat dwarf virus (Hayes, R. J. et al., J. Gen. Virol. 69:891 (1988)) and tomato golden mosaic virus (TGMV) (Elmer, J. S. et al., Plant Mol. Biol. 10:225 (1988) and Gardiner, W. E. et al., EMBO J 7:899 (1988). Therefore, agro-infection of a susceptible plant could be accomplished with a virion containing a RPVNA based on the nucleotide sequence of any of the above viruses.

A still further feature of the invention is a process for the production of a specified polypeptide or protein product such as, but are not limited to, enzymes, complex biomolecules, a ribozyme, or polypeptide or protein products resulting from anti-sense RNA. Such products include, but are not limited to: IL-1, IL-2, IL-3, IL-4, IL-5, IL-6, IL-7, IL-8, IL-9, IL-10, IL-11, IL-12, etc.; EPO; CSF including G-CSF, GM-CSF, hPG-CSF, M-CSF, etc; Factor VIII; Factor IX; tPA; hGH; receptors and receptor antagonists; antibodies; neuro-polypeptides; melanin; insulin; vaccines and the like. The non-native nucleic acid of the RPVNA comprises the transcribable sequence, which leads to the production of the desired product. This process involves the infection of the appropriate plant host with a recombinant virus or recombinant plant viral nucleic acid such as those described above, the growth of the infected host to produce the desired product, and the isolation of the desired product, if necessary. The growth of the infected host is in accordance with conventional techniques, as is the isolation of the resultant product.

For example, a coding sequence for a protein such as neomycin phosphotransferase (NPTII) α-trichosanthin, rice α-amylase, human α-hemoglobin or human 1-hemoglobin, is inserted adjacent the promoter of the TMV coat protein coding sequence, which has been deleted. In another example, a tyrosinase coding sequence such as isolated from *Streptomyces antibioticus* is inserted adjacent the same promoter of TMV, oat mosaic virus (OMV) or rice necrosis virus (RNV). Recombinant virus can be prepared as described above, using the resulting recombinant plant viral nucleic acid. Tobacco or germinating barley is infected with the recombinant virus or recombinant plant viral nucleic acid. The viral nucleic acid self-replicates in the plant tissue to produce the enzymes amylase or tyrosinase. The activity of this tyrosinase leads to the production of melanin. See, for example, Huber, M. et al., Biochemistry 24, 6038 (1985).

In a further example, a cyclodextrin glucanotransferase coding sequence, such as isolated from Bacillus sp. No. 17-1 (see U.S. Pat. No. 4,135,977) is inserted adjacent the promoter of the viral coat protein of a nucleotide sequence derived from OMV, RNV, PVY or PVX in which the coat protein coding sequence has been removed, and which then contains a non-native promoter and coat protein gene. Corn or potato is infected with the appropriate recombinant virus or recombinant plant viral nucleic acid to produce the enzyme cyclodextrin glucotransferase. The activity of this enzyme leads to the production of cyclodextrin, which is useful as a flavorant or for drug delivery.

In some plants, the production of anti-sense RNA as a product can be useful to prevent the expression of certain phenotypic traits. Particularly, some plants produce substances which are abused as drugs (e.g., cocaine is derived from the coca plant, and tetrahydrocannabinol (THC) is the active substance of abuse derived from cannabis or marijuana plants). An anti-sense RNA complementary to the plant RNA necessary for the production of an abusable substance would prevent the production of the substance. This could prove to be an effective tool in reducing the supply of illegal drugs.

A still further feature of the invention is a process for the production of an enzyme suitable for the stereospecific catalysis of an organic compound. The non-native nucleic acid comprises the transcribable sequence, which leads to the production of the desired product. This process involves the infection of the appropriate host with a recombinant virus or recombinant plant viral nucleic acid such as those described above, the growth of the infected host to produce the desired product, and the isolation of the desired product. The growth of the infected host is in accordance with conventional techniques, as is the isolation of the resultant product. The stereospecific enzyme is then utilized to catalyze the desired reaction. One use of stereospecific enzymes is in the separation of racemate mixtures.

In one example, a suitable esterase or lipase coding sequence such as isolated from an appropriate microorganism is inserted adjacent the promoter of the viral coat protein of a nucleotide sequence derived from TMV, oat mosaic virus (OMV) or rice necrosis virus (RNV) in which the coat protein coding sequence has been removed and which then contains a non-native promoter and coat protein gene. Tobacco or germinating barley is infected with the recombinant virus or recombinant plant viral nucleic acid to produce the esterase or lipase enzyme. This enzyme is isolated and used in the stereospecific preparation of a compound such as naproxen, as described in EP-A 0233656 or EP-A 0227078.

An esterase coding sequence is isolated from the appropriate microorganism, such as *Bacillus subtilis, Bacillus licheniformis* (a sample of this species is deposited with the American Type Culture Collection, Rockville, Md. (ATCC) under Accession No. 11945), *Pseudomonas fluorescens, Pseudomonas putida* (a sample of this species is deposited with the institute for Fermentation (IFO), Osaka, Japan, under Accession No. 12996), *Pseudomonas riboflavina* (a sample of this species is deposited with IFO under Accession No. 13584), *Pseudomonas ovalis* (a sample of this species is deposited with the institute of Applied Microbiology (SAM), University of Tokyo, Japan, under Accession No. 1049), *Pseudomonas aeruainosa* (IFO 13130), *Mucor angulimacrosporus* (SAM 6149), *Arthrobacter paraffineus* (ATCC 21218), Strain is III-25 (CBS 666.86), Strain LK 3-4 (CBS 667.86), Strain Sp 4 (CBS 668.86), Strain Thai iii 18-1 (CBS 669.86), and Strain Thai Vi 12 (CBS 670.86).

Advantageously, cultures of species *Bacillus subtilis* include cultures of species Bacillus species Thai 1-8 (CBS 679.85), species Bacillus species in IV-8 (CBS 680.85), species Bacillus species Nap 10-M (CBS 805.85), species Bacillus species Sp 111-4 (CBS 806.85), *Bacillus subtilis* 1-85 (Yuki, S. et al., Japan J. Gen. 42:251 (1967)), *Bacillus subtilis* 1-85/pNAPT-7 (CBS 673.86), *Bacillus subtilis* 1A-40/ pNAPT-8 (CBS 674.86), and *Bacillus subtilis* 1A-40/pNAPT-7 (CBS 675.86). Advantageously, cultures of *Pseudomonas fluorescens* include a culture of species Pseudomonas species Kpr 1-6 (CBS 807.85), and *Pseudomonas fluorescens* species (IFO 3081).

A lipase coding sequence is isolated from the appropriate microorganism such as the genera *Candida, Rhizopus, Mucor, Aspergilus, Penicillium, Pseudomonas, Chromobacterium*, and *Geotrichium*. Particularly preferred is the lipase of *Candida cylindracea* (Qu-Ming et al., Tetrahedron Letts. 27, 7 (1986)).

A fusion protein can be formed by incorporation of the non-native nucleic acid into a structural gene of the viral nucleic acid, e.g., the coat protein gene. The regulation sites on the viral structural gene remain functional. Thus, protein synthesis can occur in the usual way, from the starting codon for methionine to the stop codon on the foreign gene, to produce the fusion protein. The fusion protein contains at the amino terminal end a part or all of the viral structural protein, and contains at the carboxy terminal end the desired material, e.g., a stereospecific enzyme. For its subsequent use, the stereospecific enzyme must first be processed by a specific cleavage from this fusion protein and then further purified. A reaction with cyanogen bromide leads to a cleavage of the peptide sequence at the carboxy end of methionine residues (5.0. Needleman, "Protein Sequence Determination", Springer Publishers, 1970, N.Y.). Accordingly, it is necessary for this purpose that the second sequence contain an additional codon for methionine, whereby a methionine residue is disposed between the N-terminal native protein sequence and the C-terminal foreign protein of the fusion protein. However, this method fails if other methionine residues are present in the desired protein. Additionally, the cleavage with cyanogen bromide has the disadvantage of evoking secondary reactions at various other amino acids.

Alternatively, an oligonucleotide segment, referred to as a "linker," may be placed between the second sequence and the viral sequence. The linker codes for an amino acid sequence of the extended specific cleavage site of a proteolytic enzyme as well as a specific cleavage site (see, for example, U.S. Pat. Nos. 4,769,326 and 4,543,329). The use of linkers in the fusion protein at the amino terminal end of the non-native protein avoids the secondary reactions inherent in cyanogen bromide cleavage by a selective enzymatic hydrolysis. An example of such a linker is a tetrapeptide of the general formula Pro-Xaa-Gly-Pro (SEQ ID NO: 42) (aminoterminal end of non-native protein), wherein Xaa is any desired amino acid. The overall cleavage is effected by first selectively cleaving the xaa-Gly bond with a collagenase (E.C. 3.4.24.3., Clostridiopeptidase A) then removing the glycine residue with an aminoacyl-proline aminopeptidase (aminopeptidase-P, E.C. 3.4.11.9.) and removing the proline residue with a proline amino peptidase (E.C. 3.4.11.5). In the alternative, the aminopeptidase enzyme can be replaced by postproline dipeptidylaminopeptidase. Other linkers and appropriate enzymes are set forth in U.S. Pat. No. 4,769,326.

CEL I is a mismatch endonuclease Isolated from celery. The use of CEL I in a diagnostic method for the detection of mutations in targeted polynucleotide sequences, in particular, those associated with cancer, is disclosed in U.S. Pat. No. 5,869,245. Methods of isolating and preparing CEL I are also disclosed in this patent. However, there is no disclosure in this patent relating to the use of CEL I in DNA sequence reassortment.

Nucleic acid molecules that encode CEL I are disclosed in PCT Application Publication No. WO 01/62974 A1. As with U.S. Pat. No. 5,869,245, the use of CEL I in a diagnostic method for the detection of mutations in targeted polynucleotide sequences associated with cancer is disclosed. Also similarly, there is no disclosure relating to the use of CEL I in DNA reassortment.

The use of RES I endonuclease Is contemplated in diagnostic methods for the detection of mutations in targeted polynucleotide sequences, in particular, those associated with cancer. Examples of some of these types of diagnostic methods are disclosed in U.S. Pat. No. 5,869,245, Sokurenko, et al., and Del Tito, et al.

The reactivity of Endonuclease VII of phage T4 with DNA-loops of eight, four, or one nucleotide, or any of 8 possible base mismatches in vitro is disclosed in "Endonuclease VII of Phage T4 Triggers Mismatch Correction in Vitro" Solaro, et al., J Mol Biol 230(93)868. The publication reports a mechanism where Endonuclease VII introduces double stranded breaks by creating nicks and counternicks within six nucleotides 3' of the mispairing. The publication discloses that a time delay between the occurrence of the first nick and the counternick was sufficient to allow the 3'-5' exonuclease activity of gp43 to remove the mispairing and its polymerase activity to fill in the gap before the occurrence of the counternick. Nucleotides are erased from the first nick, which is located 3' of the mismatch on either strand and stops 5' of the mismatch at the first stable base-pair. The polymerase activity proceeds in the 5' to 3' direction towards the initial nick, which is sealed by DNA ligase. As a result, very short repair tracks of 3 to 4 nucleotides extend across the site of the former mismatch. The publication concludes with a discussion regarding the various activities Endonuclease Vii may have within phage T4. However, the publication does not disclose any practical utility for Endonuclease Vii outside of phage T4, and there is no disclosure regarding its applicability in DNA reassortment.

A method for creating libraries of chimeric DNA sequences in vivo in *Escherichia coli* is disclosed in *Nucleic Acids Research*, 1999, Vol 27, No. 18, e18, Volkov, A. A., Shao, Z., and Arnold, F. H. The method uses a heteroduplex formed in vitro to transform *E. coli* where repair of regions of non-identity in the heteroduplex creates a library of new, recombined sequences composed of elements of each parent. Although the publication discloses the use of this method as a convenient addition to existing DNA recombination methods, that is, DNA shuffling, the disclosed method is limited to the in vivo environment of *E. coli*. The publication states that there is more than one mechanism available for mismatch repair in *E. coli*, and that the 'long patch' repair mechanism, which utilizes the MutS/L/H enzyme system, was probably responsible for the heteroduplex repair.

Cited References

1. Arkin, A. P. and Youvan, D. C. (1992) An algorithm for protein engineering: simulations of recursive ensemble mutagenesis. *Proc Natl Acad Sci USA*, 89, 7811-7815.
2. Ausubel, F. M. (1987) Current protocols in molecular biology. Published by Greene Pub. Associates and Wiley-Interscience: J. Wiley, New York.
3. Ausubel, F. M. (1999) Short protocols in molecular biology: a compendium of methods from Current protocols in molecular biology. Wiley, New York.
4. Barnes, W. M. (1994) PCR amplification of up to 35-kb DNA with high fidelity and high yield from lambda bacteriophage templates. *Proc Natl Acad Sci USA*, 91, 2216-2220.

5. Bartel, D. P. and Szostak, J. W. (1993) isolation of new ribozymes from a large pool of random sequences. *Science*, 261, 1411-1418.
6. Cadwell, R. C. and Joyce, G. F. (1992) Randomization of genes by PCR mutagenesis. *PCR Methods Appl*, 2, 28-33.
7. Calogero, S., Bianchi, M. E. and Galizzi, A. (1992) in vivo recombination and the production of hybrid genes. *FEMS Microbiol Lett*, 76, 41-44.
8. Caren, R., Morkeberg, R. and Khosla, C. (1994) Efficient sampling of protein sequence space for multiple mutants. *Biotechnology (N Y)*, 12, 517-520.
9. Delagrave, S., Goldman, E. R. and Youvan, D. C. (1993) Recursive ensemble mutagenesis. *Protein Eng*, 6, 327-331.
10. Delagrave, S. and Youvan, D. C. (1993) Searching sequence space to engineer proteins: exponential ensemble mutagenesis. *Biotechnology (N Y)*, 11, 1548-1552.
11. Goldman, E. R. and Youvan, D. C. (1992) An algorithmically optimized combinatorial library screened by digital imaging spectroscopy. *Biotechnology (N Y)*, 10, 1557-1561.
12. Gram, H., Marconi, L. A., Barbas, C. F. d., Collet, T. A., Lerner, R. A. and Kang, A. S. (1992) in vitro selection and affinity maturation of antibodies from a naive combinatorial immunoglobulin library. *Proc Natl Acad Sci USA*, 89, 3576-3580.
13. Hayashi, N., Welschof, M., Zewe, M., Braunagel, M., Dubel, S., Breitling, F. and Little, M. (1994) Simultaneous mutagenesis of antibody CDR regions by overlap extension and PCR. *Biotechniques*, 17, 310, 312, 314-315.
14. Hermes, J. D., Blacklow, S. C. and Knowles, J. R. (1990) Searching sequence space by definably random mutagenesis: improving the catalytic potency of an enzyme. *Proc Natl Acad Sci USA*, 87, 696-700.
15. Holland, J. H. (1992) Adaptation in natural and artificial systems: an introductory analysis with applications to biology, control, and artificial intelligence. MIT Press, Cambridge, Mass.
16. Ji, G. and Silver, S. (1992) Regulation and expression of the arsenic resistance operon from *Staphylococcus aureus* plasmid pI258. *J Bacteriol*, 174, 3684-3694.
17. Kauffman, S. A. (1993) The origins of order: self-organization and selection in evolution. Oxford University Press, New York.
18. Marton, A., Delbecchi, L. and Bourgaux, P. (1991) DNA nicking favors PCR recombination. *Nucleic Acids Res*, 19, 2423-2426.
19. Meyerhans, A., Vartanian, J. P. and Wain-Hobson, S. (1990) DNA recombination during PCR. *Nucleic Acids Res*, 18, 1687-1691.
20. Nissim, A., Hoogenboom, H. R., Tomlinson, I. M., Flynn, G., Midgley, C., Lane, D. and Winter, G. (1994) Antibody fragments from a 'single pot' phage display library as immunochemical reagents. *EMBO J*, 13, 692-698.
21. Oleykowski, C. A., Bronson Mullins, C. R., Godwin, A. K. and Yeung, A. T. (1998) Mutation detection using a novel plant endonuclease. *Nucleic Acids Res*, 26, 4597-4602.
22. Oliphant, A. R., Nussbaum, A. L. and Struhl, K. (1986) Cloning of random-sequence oligodeoxynucleotides. *Gene*, 44, 177-183.
23. Sambrook, J., Maniatis, T. and Fritsch, E. F. (1989) Molecular cloning: a laboratory manual. Cold Spring Harbor Laboratory, Cold Spring Harbor, N.Y.
24. Stemmer, W. P. (1994a) DNA shuffling by random fragmentation and reassembly: in vitro recombination for molecular evolution. *Proc Natl Acad Sci USA*, 91, 10747-10751.
25. Stemmer, W. P. (1994b) Rapid evolution of a protein in vitro by DNA shuffling. *Nature*, 370, 389-391.
26. Stemmer, W. P., Morris, S. K. and Wilson, B. S. (1993) Selection of an active single chain Fv antibody from a protein linker library prepared by enzymatic inverse PCR. *Biotechniques*, 14, 256-265.
27. Winter, G., Griffiths, A. D., Hawkins, R. E. and Hoogenboom, H. R. (1994) Making antibodies by phage display technology. *Annu Rev Immunol*, 12, 433-455.
28. Yang, B., Wen, X., Kodali, N. S., Oleykowski, C. A., Miller, C. G., Kulinski, J., Besack, D., Yeung, J. A., Kowalski, D. and Yeung, A. T. (2000) Purification, cloning, and characterization of the CEL I nuclease. *Biochemistry*, 39, 3533-3541.
29. Sokurenko, E. V., Tchesnokova, V., Yeung, A. T., Oleykowski, C. A., Trintchina, E., Hughes, K. T., Rashid, R. A., Brint, J. M., Moseley, S. L., Lory, S. (2001) Detection of simple mutations and polymorphisms in large genomic regions. *Nucleic Acids Res*, 29, e111.
30. Yang, T. T., Sinai, P., Green, G., Kitts, P. A., Chen, Y. T., Lybarger, L., Chervenak, R., Patterson, G. H., Piston, D. W., Kain, S. R. (1998) improved fluorescence and dual color detection with enhanced blue and green variants of the green fluorescent protein. *J Biol Chem* 273, 8212-8216
31. Crameri, A., Whitehorn, E. A., Tate, E., Stemmer, W. P. (1996) improved green fluorescent protein by molecular evolution using DNA shuffling. *Nat Biotechnol* 14, 315-319.
32. Heim, R., Prasher, D. C., Tsien, R. Y. (1994) Wavelength mutations and posttranslational autoxidation of green fluorescent protein. *Proc Natl Acad Sci USA* 91, 12501-12504.
33. Del Tito, B. J., Jr., Poff, H. E., 3$^{rd}$, Novotny, M. A., Cartledge, D. M., Walker, R. I., 2$^{nd}$, Earl, C. D., Bailey, A. L. (1998) Automated fluorescent analysis procedure for enzymatic mutation detection. *Clin Chem* 44, 731-739.
34. Barnes, W. M.: The fidelity of Taq polymerase catalyzing PCR is improved by an N-terminal deletion. Gene 112 (1992) 29-35.
35. Bhagwat, M., Hobbs, L. J. and Nossal, N. G.: The 5'-exonuclease activity of bacteriophage T4 RNase H is stimulated by the T4 gene 32 single-stranded DNA-binding protein, but its flap endonuclease Is inhibited. J Biol Chem 272 (1997) 28523-30.
36. Hadi, M. Z., Ginalski, K., Nguyen, L. H. and Wilson, D. M., 3rd: Determinants in nuclease specificity of Ape1 and Ape2, human homologues of *Escherichia coli* exonuclease iii. J Mol Biol 316 (2002) 853-66.

The following non-limiting examples are provided to illustrate the present invention.

EXAMPLE 1

Cleavage of Mismatched DNA Substrate by CEL I

This example teaches the preparation of CEL I enzyme and its use in the cleavage of mismatched DNA substrate.

CEL I enzyme was prepared from celery stalks using the homogenization, ammonium sulfate, and Concanavalin A-Sepharose protocol described by Yang et al. (*Biochemistry*, 39:3533-3541 (2000), incorporated herein by reference. A 1.5 kg sample of chilled celery stalks was homogenized with a juice extractor. One liter of juice was collected, adjusted to 100 mM Tris-HCL, pH 7.7 with 100 micromolar phenylmethylsulfonyl fluoride (PMSF), and filtered through two layers of miracloth. Solid $(NH_4)_2SO_4$ was slowly added to 25% saturation while stirring on ice. After 30 minutes, the suspension was centrifuged at 27,000 g for 1.5 hours at 4° C. The supernatants were collected and adjusted with solid $(NH_4)_2SO_4$ to 80% saturation while stirring on ice followed by centrifugation at 27,000 g for 2 hours. The pellets were resuspended in buffer B (0.1 M Tris-HCL, pH 7.7, 0.5 M KCl, 100 micromolar PMSF) and dialyzed against the same buffer.

Conconavalin A (ConA) Sepharose affinity chromatography was performed by first incubating the dialyzed sample with 2 ml of ConA resin overnight with gentle agitation. The ConA resin was then packed into a 0.5 cm diameter column and washed with several column volumes of buffer B. Elution was performed using 0.3 M alpha-methyl-mannoside in buffer B. Fractions were collected in 1 ml aliquots. Fractions were assayed for mismatch cleavage activity on a radiolabeled mismatch substrate by incubating 0.1 microliter of each fraction with the mismatched probe in buffer D (20 mM Tris-HCL, pH 7.4, 25 mM KCL, 10 mM $MgCl_2$) for 30 minutes at 45° C. as described by Oleykowski et al. (Nucleic Acids Research 26: 4597-4602 (1998), incorporated herein by reference. Reaction products were visualized by separation on 10% TBE-PAGE gels containing 7% urea (Invitrogen), followed by autoradiography. Aliquots of the CEL I fractions having mismatch cleavage activity were stored frozen at −20° C. A series of five-fold dilutions of CEL I fraction #5 were then analyzed for mismatch cleavage of radiolabeled mismatch substrate. Reactions were performed either in buffer D, New England BioLabs (NEB) T4 DNA ligase buffer (50 mM Tris-HCL, pH 7.5, 10 mM $MgCl_2$, 10 mM dithiothreitol (DTT), 1 mM ATP, 25 microgram/ml BSA), or Gibco/BRL T4 DNA ligase buffer (50 mM Tris-HCL, pH 7.6, 10 mM $MgCl_2$, 1 mM DTT, 1 mM ATP, 5%(w/v) polyethylene glycol-8000). Reaction products were visualized as above. Cleavage activity in buffer D and in NEB T4 DNA ligase buffer were found to be roughly equivalent, whereas cleavage in the PEG-containing Gibco/BRL ligase buffer was enhanced by five to ten-fold compared to the other buffers.

Additional analysis of CEL I activity was carried out using defined heteroduplex DNAs from two different Green Fluorescent Protein (GFP) genes as substrate. This GFP heteroduplex substrate was prepared by annealing single stranded DNAs corresponding to cycle 3 GFP on the sense strand and wild-type GFP on the antisense strand. The single-stranded DNAs had been synthesized by asymmetric PCR and isolated by agarose gel electrophoresis. After annealing by heating to 90° C. and cooling in the presence of 1×NEB restriction enzyme buffer 2 (10 mM Tris-HCL, pH 7.9, 10 mM $MgCl_2$, 50 mM NaCl, 1 mM dithiothreitol), the heteroduplex DNA was isolated by agarose gel electrophoresis followed by excision of the heterduplex band and extraction using Qiaquick DNA spin columns. A total of twenty eight mismatches, one or two nucleotides in length, occur throughout the length of the heteroduplex molecule. The distribution of the mismatches ranges from small clusters of several mismatches separated by one or two nucleotides to mismatches separated by more than thirty base pairs on either side.

A series of three-fold dilutions of CEL I in 1×NEB T4 DNA ligase buffer were prepared and one microliter aliquots of each were incubated in two separate series of 10 microliter reactions, each containing as substrate either 0.5 microgram of a supercoiled plasmid preparation or one hundred nanograms of the cycle3/wild-type GFP heteroduplex. All reactions took place in 1×NEB T4 DNA ligase buffer. Reactions were incubated at 45° C. for 30 minutes and run on 1.5% TBE-agarose gel in the presence of ethidium bromide.

Treatment of the supercoiled plasmid preparation with increasing amounts of CEL I resulted in the conversion of supercoiled DNA to nicked circular, then linear molecules, and then to smaller fragments of DNA of random size. Treatment of the mismatched GFP substrate with the CEL I preparation resulted in the digestion of the full-length heteroduplex into laddered DNA bands which are likely to represent cleavage on opposite DNA strands in the vicinity of clusters of mismatches. Further digestion resulted in the conversion of the mismatched GFP substrate to smaller DNAs that may represent a limit digest of the heteroduplex DNA by the CEL I preparation.

EXAMPLE 2

Conservation of Full Length GFP Gene with Mismatch Resolution Cocktails

This example teaches various mismatch resolution cocktails that conserve the full length GFP Gene.

Mismatched GFP substrate was treated with various concentrations of CEL I in the presence of cocktails of enzymes that together constitute a synthetic mismatch resolution system. The enzymes used were CEL I, T4 DNA polymerase, Taq DNA polymerase and T4 DNA ligase. CEL I activity should nick the heteroduplex 3' of mismatched bases. T4 DNA polymerase contains 3'-5' exonuclease for excision of the mismatched base from the nicked heteroduplex. T4 DNA polymerase and Taq DNA polymerase contain DNA polymerase capable of filling the gap. T4 DNA ligase seals the nick in the repaired molecule. Taq DNA polymerase also has 5' flap-ase activity.

Matrix experiments were performed to identify the reaction conditions that would serve to resolve mismatches in the GFP heteroduplex substrate. In one experiment, cycle 3/wild-type GFP heteroduplex was incubated in a matrix format with serial dilutions of CEL I fraction number five (described above) at eight different concentrations. Each reaction contained 100 nanograms of heteroduplex substrate and 0.2 microliters of T4 DNA ligase (Gibco BRL) in 1×NEBT4 DNA ligase buffer and dNTPs at 250 micromolar each, in a reaction volume of 10 microliters. In all, the matrix contained 96 individual reactions. One full set of reactions was incubated at room temperature for 30 minutes while another full set was incubated at 37° C. for 30 minutes.

After incubation, PCR was used to amplify the GFP gene from each reaction. Aliquots from each PCR were then digested with HindIII and HpaI and electrophoresed on 3% agarose gels with ethidium bromide. Only cycle 3 GFP has a HindIII site and only wild-type encodes a HpaI site.

If DNA mismatch resolution occurred at either the HindIII or HpaI mismatched sites, then a proportion of the PCR product would be expected to contain both sites, yielding a novel band. The band was observed in all samples, including the negative control samples that had neither CEL I, nor T4 DNA polymerase, nor Taq DNA polymerase. The results suggested that a basal level of background recombination may have occurred at some point in the experiment other than in the GRAMMR reaction; possibly in the PCR step. PCR-mediated recombination is known to occur at some frequency between related sequences during amplification [reference Paabo, et al., DNA damage promotes jumping between templates during enzymatic amplification. J Biol Chem 265(90) 4718-4721].

In another experiment, 200 nanograms of cycle 3/wild-type GFP heteroduplex was treated with CEL I and T4 DNA polymerase In various concentrations along with 2.5 units of Taq DNA polymerase In the presence or absence of T4 DNA ligase (0.2 units; Gibco BRL). Each reaction contained 1×NEB T4 DNA ligase buffer with 0.05 mM each dNTP in a final volume of 20 microliters. Reactions were incubated for 30 minutes at 37° C. and 10 microliters were run on a 2% TBE-agarose gel in the presence of ethidium bromide. Results showed that in the presence of DNA ligase, but in the absence of T4 DNA polymerase, increasing amounts of CEL I caused greater degradation of the heteroduplexed DNA, but that this effect could be counteracted by increasing the amount of T4 DNA polymerase In the reaction. These results indicated that the various components of the complete reaction could act together to conserve the integrity of the full-length gene through DNA mismatch resolution.

Another matrix experiment was conducted to expand on these results and to identify additional conditions for DNA mismatch resolution for this synthetic system. 60 nanograms of cycle3/wild-type GFP heteroduplex were treated with CEL I and T4 DNA polymerase at various concentrations in the presence of 2.5 units of Taq DNA polymerase and 0.2 units of T4 DNA ligase in 1×NEB T4 DNA ligase buffer containing 0.5 mM of each dNTP in a reaction volume of 10 microliters. Each set of reactions was incubated for 1 hour at either 20° C., 30° C., 37° C., or at 45° C. All reactions were then run on a 1.5% TBE-agarose gels in the presence of ethidium bromide. The results showed that the GFP heteroduplex was cleaved into discrete fragments by the CEL I preparation alone. The success of DNA mismatch resolution was initially gauged by the degree to which the apparent full-length integrity of the GFP sequence was maintained by the other components of the mismatch resolution system in the presence of CEL I. Conditions of enzyme concentration and temperature were identified that conserved a high proportion of the DNA as full-length molecules in this assay. Namely, one microliter of the CEL I fraction five preparation (described in Example 1) with one microliter (1 unit) of the T4 DNA polymerase In the presence of the other reaction components which were held constant in the experiment. it was found that as the reaction temperature increased, the degradative activity of CEL I increased accordingly. Furthermore, it was shown that the other components of the repair reaction acted to conserve the integrity of the full-length DNA at 20° C., 30° C., and 37° C., but was remarkably less efficient at conserving the full-length DNA at 45° C. From these results, we concluded that under these experimental conditions, incubation at 45° C. was not optimal for the process of GRAMMR, and that incubation at 20° C., 30° C., and 37° C. were permissible.

Another experiment was performed in which alternative enzymes were used for the DNA mismatch resolution reaction. Instead of T4 DNA ligase, Taq DNA ligase was used. Pfu DNA polymerase (Stratagene) was employed in a parallel comparison to a set of reactions that contained T4 DNA polymerase as the 3' exonuclease/polymerase. Reactions were carried out in Taq DNA ligase buffer containing 8 units of Taq DNA ligase (NEB), 2.5 units Taq DNA polymerase, 0.5 mM of each dNTP, various dilutions of CEL I, and either T4 DNA polymerase or Pfu DNA polymerase). Reactions were run on a 1.5% TBE-agarose gels in the presence of ethidium bromide. If was found that in the presence of the Pfu DNA polymerase, Taq DNA polymerase, and Taq DNA ligase, the full-length integrity of the CEL I-treated substrate DNA was enhanced compared to DNA incubated with CEL I alone. This result shows that enzymes with functionally equivalent activities can be successfully substituted into the GRAMMR reaction.

EXAMPLE 3

Restoration of Restriction Sites to GFP Heteroduplex DNA after DNA Mismatch Resolution (GRAMMR)

This experiment teaches the operability of genetic reassortment by DNA mismatch resolution (GRAMMR) by demonstrating the restoration of restriction sites.

The full-length products of a twenty-fold scale-up of the GRAMMR reaction, performed at 37° C. for one hour, using the optimal conditions found above (the 1× reaction contained sixty nanograms of heteroduplex DNA, one microliter of CEL I fraction five (described in Example 1), one unit T4 DNA polymerase In the presence of 2.5 units of Taq DNA polymerase and 0.2 units of T4 DNA ligase in 1×NEB T4 DNA ligase buffer containing 0.5 mM of each dNTP in a reaction volume of 10 microliters) were gel-isolated and subjected to restriction analysis by endonucleases whose recognition sites overlap with mismatches in the GFP heteroduplex, thereby rendering those sites in the DNA resistant to restriction enzyme cleavage. The enzymes used were BamHI, HindIII, HpaI, and XhoI. Negative controls consisted of untreated GFP heteroduplex. Positive controls consisted of Cycle 3 or wild type GFP sequences, individually. All controls were digested with the same enzymes as the product of the DNA mismatch resolution reaction. All samples were run on a 2% TBE-agarose gel in the presence of ethidium bromide.

After treatment with the mismatch resolution cocktail, a proportion of the DNA gained sensitivity to BamHI and XhoI restriction endonucleases, indicating that DNA mismatch resolution had occurred. The HpaI-cut samples could not be interpreted since a low level of cleavage occurred in the negative control. The HindIII, BamHI and XhoI sites displayed different degrees of cleavage in the GRAMMR-treated samples. Restoration of the XhoI site was more extensive than that of the BamHI site, which was in turn, more extensive than restoration at HindIII site.

The extent to which cleavage occurs is indicative of the extent to which mismatches in the DNA have been resolved at that site. Differences in mismatch resolution efficiency may relate to the nature or density of mismatches present at those sites. For example, the XhoI site spans a three-mismatch cluster, whereas the BamHI site spans two mismatches and the HindIII site spans a single mismatch.

EXAMPLE 4

GRAMMR-Reassorted GFP Genes

This example demonstrates that GRAMMR can reassort sequence variation between two gene sequences in a heteroduplex and that there are no significant differences in GRAMMR products that were directly cloned, or PCR amplified prior to cloning.

The GRAMMR-treated DNA molecules of Example 3 were subsequently either directly cloned by ligation into pCR-Blunt ii-TOPO (Invitrogen), or amplified by PCR and ligated into pCR-Blunt II-TOPO according to the manufacturer's instructions, followed by transformation into E. coli. After picking individual colonies and growing in liquid culture, DNA was prepared and the sequences of the GFP inserts were determined. As negative controls, the untreated GFP heteroduplex substrate was either directly cloned or PCR amplified prior to cloning into the plasmid.

In GRAMMR, reassortment of sequence information results from a process of information transfer from one strand to the other. These sites of information transfer are analogous to crossover events that occur in recombination-based DNA shuffling methods. For the purposes of relating the results of these reassortment experiments, however, the GRAMMR output sequences are described in terms of crossovers. Sequences of twenty full-length GFP clones that were derived from the GRAMMR-treated GFP genes were analyzed. Four of these clones were derived from DNA that had been directly cloned into pZeroBlunt [ref] following GRAMMR treatment (no PCR amplification). The other sixteen sequences were cloned after PCR amplification. Analysis of these full-length GFP sequences revealed that all twenty sequences had undergone sequence reassortment having between one and ten crossovers per gene. A total of 99 crossovers were found in this set of genes, giving an average of about 5 crossovers per gene. With the distance between the first and last mismatches of about 590 nucleotides, an overall frequency of roughly one crossover per 120 base-pairs was calculated. Within this set of twenty clones, a total of seven point mutations had occurred within the sequences situated between the PCR primer sequences, yielding a mutation frequency of roughly 0.05%.

Thirty-five clones that had not been subjected to GRAMMR treatment were sequenced. Of these controls, fourteen were derived from direct cloning and twenty-one were obtained after PCR amplification using the GFP heteroduplex as template. Of these thirty-five non-GRAMMR treated control clones, eight were recombinants, ranging from one to three crossovers, with most being single crossover events. A total of twenty-five point mutations had occurred within the sequences situated between the PCR primers, yielding a mutation frequency of roughly 0.1%.

No significant differences were observed between the GRAMMR-treated products that were either directly cloned or PCR amplified. Notably, though, in the non-GRAMMR-treated controls, the frequency of recombinants was higher in the PCR amplified DNAs than in the directly cloned DNAs. This higher frequency is consistent with results obtained by others in which a certain level of recombination was found to be caused by "jumping PCR." [Paabo, et al., DNA damage promotes jumping between templates during enzymatic amplification. J Biol Chem 265(90)4718-4721].

EXAMPLE 5

Heteroduplex Substrate Preparation for Plasmid-on-Plasmid Genetic Reassortment By DNA Mismatch Resolution (POP GRAMMR) of GFP Plasmids This example teaches that heteroduplex substrate for Genetic Reassortment by DNA Mismatch Resolution can be in the form of intact circular plasmids. Cycle 3-GFP and wild-type GFP heteroduplex molecules were prepared plasmid-on-plasmid (POP) format. in this format, the GFP sequences were reasserted within the context of a circular double-stranded plasmid vector backbone. This made possible the recovery of the reasserted product by direct transformation of E. coli using an aliquot of the GRAMMR reaction. Consequently, neither PCR amplification nor other additional manipulation of the GRAMMR-treated DNA was necessary to obtain reasserted clones.

Mismatched DNA substrate for POP-GRAMMR reactions was generated containing wild-type GFP (SEQ ID NO:01) and Cycle 3 GFP (SEQ ID NO:02), resulting in the two pBluescript-based plasmids, pBSWTGFP (SEQ ID NO:03) and pBSC3GFP (SEQ ID NO:04), respectively. The GFPs were inserted between the KpnI and EcoRI sites of the pBluescript polylinker so that the only sequence differences between the two plasmids occurred at sites where the wild-type and Cycle 3 GFPs differ from one-another. Both plasmids were linearized by digestion of the plasmid backbone with SapI, cleaned up using a DNA spin-column, mixed, amended to 1×PCR buffer (Barnes, 1994; PNAS, 91, 2216-2220), heated in a boiling water bath for three minutes, and slow-cooled to room temperature to anneal the denatured DNA strands. Denaturing and annealing these DNAs led to a mixture of duplexes, the re-formation of parental duplexes, and the formation of heteroduplexes from the annealing of strands from each of the two input plasmids. Parental duplexes were deemed undesirable for GRAMMR and were removed by digestion with restriction enzymes that cut in one or the other parental duplex but not in the heteroduplexed molecules. PmlI and XhoI were chosen for this operation since PmlI cuts only in the wild-type GFP sequence and XhoI cuts only Cycle 3 GFP. After treatment with these enzymes, the products were resolved on an agarose gel. The full-length, uncut heteroduplex molecules were resolved from the PmlI- and XhoI-cut parental homoduplexes in an agarose gel and purified by excision of the band and purification with a DNA spin column.

The resulting population of heteroduplexed molecules was treated with DNA ligase to convert the linear DNA into circular, double-stranded DNA heteroduplexes. After confirmation by agarose gel-shift analysis, the circular double-stranded GFP heteroduplexed plasmid was used as substrate for GRAMMR reactions. Examples of the resulting clones are included as SEQ ID NO:05, SEQ ID NO:06, SEQ ID NO:07, and SEQ ID NO:08.

EXAMPLE 6

Exemplary Reaction Parameters for Genetic Reassortment by DNA Mismatch Resoluton CEL I and T4 DNA Polymerase Concentrations Compared The GRAMMR reaction involves the interaction of numerous enzymatic activities. Several parameters associated with the GRAMMR reaction were examined, such as CEL I concentration, T4 DNA polymerase concentration, reaction temperature, substitution of T4 DNA polymerase with T7 DNA polymerase, the presence of Taq DNA polymerase, and the source of the CEL I enzyme. A matrix of three different CEL I concentrations versus two concentrations of T4 DNA polymerase was set up to examine the limits of the in vitro DNA mismatch resolution reaction.

Twenty-one nanograms (21 ng) of the circular double-stranded heteroduplexed plasmid, prepared as described above, was used as substrate in a series of ten microliter reactions containing 1×NEB ligase buffer, 0.5 mM each dNTP, 1.0 unit Taq DNA polymerase, 0.2 units T4 DNA ligase (Gibco/BRL), either 1.0 or 0.2 units T4 DNA polymerase, and either 0.3, 0.1, or 0.03 microliters of a CEL I preparation (fraction 5, described in Example 1). Six reactions representing all six combinations of the two T4 DNA polymerase concentrations with the three CEL I concentrations were prepared, split into equivalent sets of five microliters, and incubated at either 20 degrees C. or 37 degrees C. A control reaction containing no CEL I and 0.2 unit of T4 DNA polymerase with the other reaction components was prepared and incubated at 37 degrees C. After 30 minutes, one microliter aliquots of each reaction were transformed into competent DH5-alpha *E. coli* which were then plated on LB amp plates. Colonies were picked and cultured. Plasmid DNA was extracted and examined by restriction fragment length polymorphism analysis (RFLP) followed by sequence analysis of the GFP gene sequences. RFLP analysis was based on differences in several restriction enzyme recognition sites between the wild-type and Cycle 3 GFP genes. The RFLP results showed that throughout the CEL I/T4 DNA polymerase/temperature matrix, reassortment of restriction sites, that is GRAMMR, had occurred, and that no such reassortment had occurred in the zero CEL I control clones. DNA sequence analysis confirmed that reassortment had occurred in all of the CEL I-containing samples. Sequencing also confirmed that the zero-CEL I controls were not reasserted, with the exception of a single clone of the 16 control clones, which had a single-base change from one gene sequence to the other, presumably resulting either from repair in *E. coli* or from random mutation. The sequences of several exemplary GRAMMR-reassorted GFP clones are shown; all of which came from the reaction containing 0.3 microliters of the CEL I preparation and 1.0 unit of T4 DNA polymerase Incubated at 37 degrees C. The parental wild-type and Cycle 3 GFP genes are shown first for reference.

EXAMPLE 7

Taq DNA Polymerase is Not Required for Genetic Reassortment by DNA Mismatch Resolution This experiment teaches that Taq DNA Polymerase does not dramatically, if at all, contribute or interfere with the functioning of Genetic Reassortment by DNA Mismatch Resolution (GRAMMR). Taq DNA polymerase Is reported to have a 5' flap-ase activity, and had been included in the teachings of the previous examples as a safeguard against the possible formation and persistence of undesirable 5' flaps in the heteroduplexed DNA undergoing GRAMMR.

GRAMMR reactions were set up, as in Example 6, with twenty-one nanograms of the circular double-stranded heteroduplexed GFP plasmid substrate in ten microliter reactions containing 1×NEB ligase buffer, 0.5 mM each dNTP, 0.2 units T4 DNA ligase, 1.0 unit T4 DNA polymerase, 1.0 microliter of a CEL I preparation (fraction 5, described in Example 1), and either 2.5 units, 0.5 units of Taq DNA polymerase, or no Taq DNA polymerase. After 30 minutes, one microliter aliquots of each reaction were transformed into competent DH5-alpha *E. coli* which were then plated on LB amp plates. Colonies were picked and cultured. Plasmid DNA was extracted and examined by RFLP analysis followed by sequence analysis of the GFP gene sequences. The RFLP results showed that reassortment of restriction sites, that is, GRAMMR, had occurred both in the presence and the absence of Taq DNA polymerase In the GRAMMR reaction. DNA sequence analysis confirmed these results. Therefore, the data shows that Taq DNA polymerase was unnecessary for GRAMMR.

EXAMPLE 8

Alternate Proofreading DNA Polymerases for Genetic Reassortment by DNA Mismatch Resolution This experiment teaches that Genetic Reassortment by DNA Mismatch Resolution is not limited to the use of T4 DNA polymerase, and that alternate DNA polymerases can be substituted for it.

Reactions were set up, as in Example 6, with twenty-one nanograms of the circular double-stranded heteroduplexed GFP plasmid substrate in ten microliter reactions containing 1×NEB ligase buffer, 0.5 mM each dNTP, 0.2 units T4 DNA ligase (Gibco/BRL), 10 units or 2 units of T7 DNA polymerase, 1.0 microliter of a CEL I preparation (fraction 5, described in Example 1), and 2.5 units of Taq DNA polymerase. After 30 minutes, one microliter aliquots of each reaction were transformed into competent DH5-alpha *E. coli* which were then plated on LB amp plates. Colonies were picked and cultured. Plasmid DNA was extracted and examined by RFLP analysis followed by sequence analysis of the GFP gene sequences. The RFLP results showed that reassortment of restriction sites, that is GRAMMR, had occurred in both T7 DNA polymerase-containing reactions. DNA sequence analysis confirmed these results. Therefore, the data shows that T7 DNA polymerase can substitute for T4 DNA polymerase for GRAMMR. In addition, it shows that individual components and functionalities can be broadly substituted in GRAMMR, while still obtaining similar results.

EXAMPLE 9

Use of Cloned CEL I in the GRAMMR Reaction

This example teaches that CEL I from a cloned source can be used in place of native CEL I enzyme purified from celery in Genetic Reassortment By DNA Mismatch Resolution without any noticeable change in results.

The cDNA of CEL I was cloned from celery RNA. The gene was inserted into a TMV viral vector and expressed. Transcripts of the construct were used to infect *Nicotiana benthamiana* plants. Infected tissue was harvested, and the CEL I enzyme was purified. The GRAMMR results obtained using the purified enzyme were compared to those using CEL I purified from celery, and were found to be similar.

Reactions were set up using twenty-one nanograms of the circular double-stranded heteroduplexed GFP plasmid substrate in ten microliters containing 1×NEB ligase buffer, 0.5 mM each dNTP, 0.2 units T4 DNA ligase (Gibco/BRL), 1 unit of T4 DNA polymerase, and either 1.0 microliter of CEL I purified from celery (fraction 5, described in Example 1), or 0.3 microliters of CEL I purified from a cloned source. After 30 minutes, one microliter aliquots of each reaction were transformed into competent DH5-alpha *E. coli* which were then plated on LB amp plates. Colonies were picked and cultured. Plasmid DNA was extracted and examined by RFLP analysis followed by sequence analysis of the GFP gene sequences. The RFLP results showed that reassortment of restriction sites, that is, GRAMMR had occurred in both celery-derived CEL I, as well as cloned CEL I-containing reactions. DNA sequence analysis confirmed these results. Therefore, the data shows CEL I from a cloned source can be used in lieu of CEL I from celery for GRAMMR. In addition, the data demonstrates that it is CEL I activity that is part of the GRAMMR method, rather than a coincidental effect resulting from the purifying steps used in extracting CEL I from celery.

EXAMPLE 10

Molecular Breeding of Tobamovirus 30K Genes in a Viral Vector.

In the preceding examples, Genetic Reassortment by DNA Mismatch Resolution has been taught to be useful for reasserting sequences that are highly homologous, for example, wtGFP and Cycle 3 GFP are 96% identical. The present example teaches that GRAMMR can be used to reassort more divergent nucleic acid sequences, such as genes encoding tobamovirus movement protein genes.

Heteroduplexes of two tobamovirus movement protein (MP) genes that are approximately 75% identical were generated. The heteroduplex substrate was prepared by annealing partially-complementary single-stranded DNAs of opposite strandedness synthesized by asymmetric PCR; one strand encoding the movement protein gene from the tobacco mosaic virus U1 type strain (TMV-U1) (SEQ ID NO:09), and the other strand encoding the movement protein gene from tomato mosaic virus (TOMV) (SEQ ID NO:10). The sequences of the two partially complementary movement protein genes were flanked by 33 nucleotides of absolute complementarity to promote annealing of the DNAs at their termini and to facilitate PCR amplification and cloning. The annealing reaction took place by mixing 2.5 micrograms of each single-stranded DNA in a 150 microliter reaction containing 333 mM NaCl, 33 mM MgCl2, 3.3 mM dithiothreitol, 166 mM Tris-HCl, pH 7, and incubating at 95° C. for one minute followed by slow cooling to room-temperature. GRAMMR was performed by incubating 5 microliters of the heteroduplex substrate in a 20 microliter reaction containing 1×NEB ligase buffer, 0.5 mM each dNTP, 0.4 units T4 DNA ligase (Gibco/BRL), 2.0 units of T4 DNA polymerase, and CEL I. The CEL I was from a cloned preparation and the amount that was used varied from 2 microliters of the prep, followed by five serial 3-fold dilutions. A seventh preparation with no CEL I was prepared, which served as a control.

After one hour at room-temperature, DNA was purified from the reactions using Strataprep spin DNA purification columns (Stratagene, LaJolla, Calif.) and used as templates for PCR reactions using primers designed to anneal to the flanking primer-binding sites of the two sequences. PCR products from each reaction were purified using Strataprep columns, digested with AvrII and PacI, and ligated into the movement protein slot of similarly-cut pGENEWARE-MP-Avr-Pac. This plasmid contained a full-length infectious tobamovirus-GFP clone modified with AvrII and PacI sites flanking the movement protein gene to permit its replacement by other movement protein genes. After transformation of DH5-alpha *E. coli* and plating, colonies were picked, cultures grown, and DNA was extracted. The movement protein inserts were subjected to DNA sequence analysis from both directions and the sequence data confirmed that in the majority of inserts derived from the GRAMMR-treated material were reasserted sequences made up of both TMV-U1 and ToMV movement protein gene sequences. The DNA sequences of several exemplary GRAMMR MP clones are shown as SEQ ID NO:11, SEQ ID NO:12, SEQ ID NO:13, SEQ ID NO:14, and SEQ ID NO:15.

EXAMPLE 11

GRAMMR Reassortment to Generate improved Arsenate Detoxifying Bacteria

Arsenic detoxification is important for mining of arsenopyrite-containing gold ores and other uses, such as environmental remediation. Plasmid pGJ103, containing an arsenate detoxification operon (Ji and Silver, 1992)(Ji, G. and Silver, S., Regulation and expression of the arsenic resistance operon from Staphylococcus aureus plasmid pI258, J. Bacteriol. 174, 3684-3694 (1992), incorporated herein by reference), is obtained from Prof. Simon Silver (U. of Illinois, Chicago, Ill.). *E. coli* TG1 containing pGJ103, containing the pI258 ars operon cloned into pUC19, has a MIC (minimum inhibitory concentration) of 4 μg/ml on LB ampicillin agar plates. The ars operon is amplified by mutagenic PCR [REF], cloned into pUC19, and transformed into *E. coli* TG1. Transformed cells are plated on a range of sodium arsenate concentrations (2, 4, 8, 16 mM). Colonies from the plates with the highest arsenate levels are picked. The colonies are grown in a mixed culture with appropriate arsenate selection. Plasmid DNA is isolated from the culture. The plasmid DNA is linearized by digestion with a restriction endonuclease that cuts once into the pUC19 plasmid backbone. The linearized plasmids are denatured by heating 10 min. at 94° C. The reaction is allowed to cool to promote annealing of the single strands. Partially complementary strands that hybridize have non-basepaired nucleotides at the sites of the mismatches. Treatment with CEL I (purified by the method of Example 9) causes nicking of one or the other polynucleotide strand 3' of each mismatch. The presence of a polymerase containing a 3'-to-5' exonuclease ("proofreading") activity, such as T4 DNA polymerase allows excision of the mismatch, and subsequent 5'-to-3' polymerase activity fills in the gap using the other strand as a template. T4 DNA ligase then seals the nick by restoring the phosphate backbone of the repaired strand. The result is a randomization of mutations among input strands to give output strands with potentially improved properties. These output polynucleotides are transformed directly into *E. coli* TG1 and the cells are plated at higher arsenate levels; 8, 16, 32, 64 mM. Colonies are picked from the plates with the highest arsenate levels and another round of reassortment is performed as above except that resulting transformed cells are plated at 32, 64, 128, 256 mM arsenate. The process can then be repeated one or more times with the selected clones in an attempt to obtain additional improvements.

EXAMPLE 12

Cloning, Expression and Purification of CEL I Endonuclease

This example teaches the preparation of nucleic acid molecules that were used for expressing CEL I endonuclease from plants, identified herein as, p1177 MP4-CELI Avr (SEQ ID NO:01), and p1177 MP4-CELI 6HIS (SEQ ID NO:02). In particular, this example refers to disclosures taught in U.S. Pat. Nos. 5,316,931, 5,589,367, 5,866,785, and 5,889,190, incorporated herein by reference.

The aforementioned clones were deposited with the American Type Culture Collection, Manassas, Va. 20110-2209 USA. The deposits were received and accepted on Dec. 13, 2001, and assigned the following Patent Deposit Designation numbers, PTA-3926 (p1177 MP4-CelI Avr, SEQ ID NO:01), and PTA-3927 (p1177 MP4-CelI 6HIS, SEQ ID NO:02).

1. Celery RNA Extraction:

Celery was purchased from a local market. Small amounts of celery tissue (0.5 to 0.75 grams) were chopped, frozen in liquid nitrogen, and ground in a mortar and pestle in the presence of crushed glass. After addition of 400 microliters of Trizol and further grinding, 700 microliters of the extract were removed and kept on ice for five minutes. Two hundred microliters of chloroform were then added and the samples were centrifuged, left at room temperature for three minutes, and re-centrifuged at 15,000 g for 10 minutes. The aqueous layer was removed to a new tube and an equal volume of isopropanol was added. Tubes were inverted to mix and left at room temperature for 10 minutes followed by centrifugation at 15,000 g for ten minutes at 4° C. The pellet was washed twice in 400 microliters of 70% ethanol, once in 100% ethanol, air dried, and resuspended in 40 microliters of distilled water. One microliter of RNasin was added and 3.5 microliters was run on a 1% agarose gel to check the quality of the RNA prep (Gel picture). The remainder was stored at −70° C. until further use.

2. CEL I Gene Cloning and Expression by a Viral Vector:

The total RNA from celery was subjected to reverse transcription followed by PCR to amplify the cDNA encoding the CEL I gene sequence. In separate reactions, eleven microliters of the total celery RNA prep was mixed with one microliter (50 picomoles) of either CelI-Avr-R, CelI-6H-R, or with two microliters of oligo dT primer. CelI-Avr-R was used to prime cDNA and amplify the native CEL I sequence at the 3' end of the gene, while CelI-6H-R was used to add a sequence encoding linker peptide and a 6-His tag to the 3' terminus of the CEL I gene. The samples were heated to 70° C. for one minute and quick-chilled on ice prior to the addition of 4 microliters of 5× Superscript II buffer, two microliters of 0.1M DTT, 1 microliter of 10 mM each dNTP, and 1 microliter of Superscript II (Gibco/BRL) to each reaction. The reactions were incubated at 42° C. for one hour.

PCR amplification of the CEL I cDNA sequence was performed using the method of W. M. Barnes (*Proc Natl Acad Sci. USA,* 1994 Mar. 15;91(6): 2216-20) with a Taq-Pfu mixture or with Pfu alone. The RT reaction primed with CelI-Avr-R was used as template for a PCR using primers CelI-Pac-F (as the forward primer) paired with CelI-Avr-R (as the reverse primer). In other PCRs, the RT reaction that was primed with oligo dT was used as template for both of the above primer pairs. All PCR reactions were performed in 100 microliters with 30 cycles of annealing at 50° C. and two minutes of extension at 72° C. Aliquots of the resulting reactions were analyzed by agarose gel electrophoresis. Reactions in which Pfu was used as the sole polymerase showed no product. All reactions performed with the Taq/Pfu mixtures yielded product of the expected size. However, those amplified from cDNA primed with CEL I specific primer pairs gave more product than reactions amplified from cDNA primed with oligo-dT. DNAs from the PCR reactions that gave the most product were purified using a Zymoclean DNA spin column kit and digested with PacI and AvrII, gel-isolated, and ligated into PacI and AvrII-digested plasmid pRT130, a tobamovirus-based GENEWARE® vector. 2 microliters of each ligation were transformed into DH5α competent *E. coli* and cultured overnight on LB-amp agar plates. Colonies were picked and grown overnight in liquid culture, and plasmid DNA was isolated using a Qiagen plasmid prep kit. 12 clones from each construct were screened by digestion with PacI and AvrII and 11 of 12 of each set were positive for insert of the correct size. Ten of the clones for each construct were transcribed in-vitro and RNA was inoculated to *N. benthamiana* plants. in addition, the CEL I gene inserts in both sets of ten clones were subjected to sequence analysis. Several clones containing inserts encoding the native form of CEL I had sequence identical to the published CEL I sequence in WO 01/62974 A1. One clone containing an insert encoding CEL I fused to a 6-Histidine sequence was identical to the published CEL I sequence. One clone of each (pRT130-CelI Avr-B3 and pRT130-CelI 6His-A9, respectively) was selected for further work. The CEL I-encoding sequences in these clones were subsequently transferred to another GENEWARE vector. The sequences of these clones, p1177 MP4-CelI Avr-B3, and p1177 MP4-CelI 6His-A9 are provided as SEQ ID NO:01 and SEQ ID NO:2, respectively. If should be noted that applicant's designations for each of the clones were shortened in the deposit to the aforementioned deposit with the American Type Culture Collection, that is, p1177 MP4-CelI Avr-B3 is referred to as p1177 MP4-CelI Avr; and p1177 MP4-CelI 6His-A9 is referred to as p1177 MP4-CelI 6His. The clone p1177 MP4-CelI Avr (SEQ ID NO:01) contained the CEL I open reading frame extending from nucleotide 5765 to 6655 (SEQ ID NO:03); and the clone p1177 MP4-celI 6His-A9 (SEQ ID NO:02) contained the CEL I open reading frame extending from nucleotide 5765-6679.

3. Assay of Cloned CEL I Activities.

To determine whether the GENEWARE constructs containing CEL I sequences could produce active CEL I enzyme, samples of pRT130-celI Avr (SEQ ID NO: 01) and pRT130-celI 6His (SEQ ID NO:2), and GFP-GENEWARE control-infected plants were harvested and homogenized in a small mortar and pestle in Tris-HCl at pH 8.0. Extracts were clarified and assayed for supercoiled DNA nicking activity. Each supercoiled DNA nicking assay was performed in a reaction containing 0.5 micrograms of a supercoiled plasmid prep of a pUC19-derivative in 1×NEB ligase buffer in a total volume of 10 microliters. The amounts of plant extract added to the reactions were 0.1 microliter, 0.01 microliter, or 0.001 microliter, incubated at 42° C. for 30 minutes, and run on a 1% TBE-agarose gel in the presence of ethidium bromide. Little or no nicking activity was detected in the GFP-GENEWARE control-infected plant extract whereas extracts from plants infected with the CEL I-GENEWARE constructs showed appreciable amounts of activity against the plasmid DNA substrate.

Additional activity assays were performed on extracts of plants inoculated with pRT130-celI Avr-B3 and pRT130-celI 6His-A9. In these assays, intracellular fluid was washed from infected leaves and assayed separately from material obtained from the remaining washed leaf tissues. Assays were performed as described above with the exception that the incubation was at 37° C. for one hour. Samples were run on a 1% TBE-agarose gel in the presence of ethidium bromide and photographed.

4. Purification of 6His-tagged CEL I from Infected *N. benthamiana* Plants.

*N. benthamiana* plants were inoculated with RNA transcripts from pRT130-celI 6His-A9 at 20-21 days post-sowing. Tissues were harvested from 96 infected plants at 10 days post-inoculation and subjected to intracellular fluid washes. Briefly, infected leaf and stem material was vacuum infiltrated for 30 seconds twice with chilled infiltration buffer (50 mM phosphate pH 4 in the presence of 7 mM β-ME). Infiltrated tissues were blotted to adsorb excess buffer and secreted proteins were recovered by centrifugation at 2500×g for 20 min using basket rotor (Beckman). PMSF was added to the extracted intracellular fluid (IF) containing recombinant CEL_I to a final concentration of 1 mM, and incubated at 25° C. for 15 min with stirring. After addition of imidazole (pH 6.0) and NaCl to the extract to the final concentration of 5 mM and 0.5 M respectively, IF was adjusted to pH 5.2 and filtered through 1.2μ Sartorius GF membrane (Whatman) to remove most of the Rubisco and green pigments. Immediately after clarification, pH was adjusted to 7.0 using concentrated NaOH solution and incubated on ice for 20 min to allow non-proteinaceous material to precipitate. IF was further clarified using 0.8 μ or 0.65/0.45 μ Sartorius GF (Whatman). Recombinant CEL I was purified from the clarified IF by metal chelating affinity chromatography using Ni$^{2+}$ Fast Flow Sepharose (Amersham Pharmacia Biotech, NJ) equilibrated with binding buffer (50 mM phosphate, 0.5 M NaCl; pH 7.0) containing 5 mM imidazole, with a linear velocity of 300 cm/hr. Unbound protein was washed with 20 mM imidazole/ binding buffer, and CEL I was eluted from $Ni^{2+}$ Sepharose with a linear gradient of 20 to 400 M imidazole in the binding buffer. Fractions still containing imidazole were assayed for supercoiled DNA nicking activity as described above but were found to have negligible activity. The same fractions were then dialyzed against 0.1 M Tris-HCl, pH 8.0 in the presence of $ZnCl_2$ using 10 kD MWCOF dialysis tubing (Pierce) and assayed again. The supercoiled DNA nicking activity was restored after this dialysis.

IF and purified CEL-I protein were analyzed using Sodium Dodecyl Sulfate Polyacrylamide Gel Electrophoresis (SDS-PAGE) precast Tris-glycine gels (Invitrogen, Carlbad, Calif.) in the buffer system of Laemmli with a Xcell ii Mini-Cell apparatus (Invitrogen, Carlsbad, Calif.). The protein bands were visualized by Coomassie brilliant blue and by silver staining. SDS-PAGE Gels were scanned and analyzed using Bio-Rad gel imager.

Mass Spectrometry of Purified CEL I

The average molecular mass of the purified CEL I was determined by matrix-assisted laser/desorption ionization time-of-flight mass spectrometry (MALDI-TOF). An aliquot of CEL I was diluted 1:10 with 50% acetonitrile/water and mixed with sinapinic acid matrix (1:1 v/v) using a PE Biosystem DE-Pro mass spectrometer. The mass spectrometry was performed using an accelerating voltage of 25 kV and in the positive-linear ion mode.

Mass Spectrometry of Peptides isolated from Purified CEL I.

CEL I was separated on SDS-PAGE on a 14% gel and stained with Coomassie brilliant blue. A single homogenous band was visible. This band was excised and de-stained completely. Protein was reduced in the presence of 10 mM DDT in 50% acetonitrile for 30 min at 37° C. and reduced sulfhydro groups were blocked in the presence of 28 mM iodoacetamide in 50% acetonitrile for 30 min at 24° C. in absence of light. Gel pieces were washed with 50% acetonitrile and after partial dehydration, the excised CEL I band was macerated in a solution of high purity trypsin (Promega). The proteolytic digestion was allowed to continue at 37° C. for 16 h. The resulting peptides were eluted from gel pieces with a 50% acetonitrile and 0.1% tri-fluoro-acetic acid (TFA) concentrated in a SpeedVac. The peptides were analyzed by MALDI-TOF. Mixed tryptic digests were crystallized in a matrix of α-cyano-4-hydroxycinnamic acid and analyzed by using a PerSeptive Biosystem DE-STR MALDI-TOF mass spectrometer equipped with delayed extraction operated in the reflector-positive ion mode and accelerating voltage of 20 kV. Expected theoretical masses were calculated by MS-digest (Protein Prospector) or GPMAW program (Lighthouse Data, Odense, Denmark). For tandem mass spectrometry (nano electrospray ionization (ESI), peptide samples were diluted with 5% acetonitrile/0.1% formic acid and subjected to LC MS/MS, analyzed on a quadropole orthogonal time-of-flight mass spectrometry instrument (micromass, inc., Manchester, UK). The data were processed by Mslynx and database was searched by Sonar.

Virally expressed, recombinant CEL I was secreted to the IF. Clarified IF-extracted material was used to purify the His-tag CEL I activity. CEL I was purified using one step $Ni^{2+}$ affinity chromatography separation. A highly purified homogeneous single protein band was purified as determined by Coomassie stained SDS-PAGE and mass spectrometry. The size of mature proteins and percent glycosylation concur with what has been reported for the CEL I protein isolated from celery (Yang et al., 2000). The purified CEL I has an average molecular mass of 40 kD as determined by MALDI-TOF mass spectrometry, indicates 23.5% glycosylation by mass. CEL I has four potential glycosylation cites at amino acid positions 58, 116, 134, and 208. A mono-isotopic mass of 2152.6086 (2152.0068 Theoretical) Da corresponding to the mass of the peptide 107-125 (K)DMCVAGAIQN-FTSQLGHFR(H) (SEQ ID NO: 35) that was recovered by MALDI-TOF, indicates that asparagine 116 is not glycosylated. Together, these gel analyses and mass spectrometry data indicate that a significant fraction of the CEL I protein was recoverable from the intracellular space, and that the protein was correctly processed in the N. benthamiana plant.

For subsequent experiments, the 6-His tagged CEL I gene was produced using p1177 MP4-cell 6His-A9. This clone was transcribed and inoculated onto N. benthamiana plants, which were harvested 8 days post infection. The plant material was combined with 2 volumes of extraction buffer (500 mM NaCl, 100 mM NaPi, 25 mM Tris pH 8.0, 7 mM Beta-mercaptoethanol, 2 mM PMSF) and vacuum infiltrated. Following buffer infiltration the tissue was macerated in a juice extractor, the resulting green juice adjusted to 4% w/v polyethyleneglycol, and let stand at 4° C. for one hour. The green juice was clarified by either centrifugation at low speed (3500×g) for 20 minutes or combined with perlite (2% w/v) and filtered through a 1.2 µm filter. The tagged CEL I can be selectively purified from the clarified green juice by metal affinity chromatography. The green juice was either combined with nickel-NTA resin, and batch binding of the CEL I performed, or purification was performed in column format, where the green juice was permitted to flow through a bed of nickel-NTA resin. For binding, the clarified green juice was adjusted to 10% w/v glycerol and 10 mM imidazole. Following binding the resin was washed extensively with wash buffer (330 mM NaCl, 100 mM NaPi, pH 8.0, 10 mM imidazole) and the bound CEL I enzyme eluted from the nickel-NTA resin in 2 resin-bed volumes of 1× phosphate-buffered saline (PBS) containing 400 mM imidazole. The CEL I preparation was subsequently dialyzed against 1×PBS to remove the imidazole, assayed for activity, and stored at 4° C. or at −20° C. with or without glycerol until use.

EXAMPLE 13

Cloning, Expression and Use of RES I Endonuclease

This example teaches the construction of a cDNA library from Selaginella lepidophylla, the identification of a nucleic acid sequence from the library that encodes an endonuclease, and the expression of the new endonuclease, herein designated as "RES I."

RNA was extracted from tissues of the resurrection plant, Selaginella lepidophylla, using the Trizol method, and oligo-dT primed cDNA that was prepared using standand methodology. Resulting cDNAs were ligated into a GENEWARE-based cloning vector and the ligation products were transformed into competent E. coli cells. Bacterial colonies containing GENEWARE cDNA clones were picked at random and grown as liquid cultures prior to DNA prepping and determination of the cloned cDNA sequences. The sequence files for the cloned Selaginella cDNAs were loaded into a database which was then searched by BLAST analysis for sequences that had similarity to the DNA sequence of the CEL I gene. BLAST analysis was also performed on other DNA sequence databases containing sequences of cDNAs obtained from other species.

BLAST hits that showed some level of homology to the celery CEL I sequence were identified in libraries from several species and the corresponding GENEWARE-cDNA clones were re-arrayed into a single set of GENEWARE-cDNA clones. This set of cDNA clones was then transcribed in vitro to generate infectious GENEWARE transcripts which were then inoculated onto leaves on *Nicotiana benthamiana* plants for expression analysis of the cDNA sequences encoded within the GENEWARE viral genome. At seven days post-inoculation, leaf samples were taken from the infected plants and homogenized in two volumes of water. The extracts were then assayed for supercoiled DNA nicking and cleavage activity.

Each supercoiled DNA nicking assay was performed in a reaction containing 0.5 micrograms of a supercoiled plasmid prep of a pUC19-derivative in 1×NEB T4 DNA ligase buffer in a total volume of 10 microliters. The amounts of plant extract added to the reactions were 1 microliter, 0.33 microliter, or 0.011 microliter, incubated at 37° C. for 30 minutes, and run on a 1% TAE-agarose gel in the presence of Gelstar fluorescent DNA staining reagent. Little or no nicking activity was detected in uninfected plant extracts whereas only extracts from plants infected with GENEWARE constructs containing cDNAs for a single gene from *Selaginella lepidophylla* showed appreciable amounts of activity against the plasmid DNA substrate.

A sample of the aforementioned *Selaginella lepidophylla* gene, as shown in FIG. 3 (SEQ ID NO: 16), was mailed to the American Type Culture Collection, Manassas, Va. 20110-2209 USA on Jul. 29, 2002. The deposit was received on Jul. 30, 2002. The sample was accepted on Aug. 29, 2002, and assigned the following Patent Deposit Designation number, PTA-4562.

The complete gene sequences of these clones were determined and PCR primers were designed to amplify the open reading frame minus any non-coding 5' and 3' sequences and to add a six histidine tail to the C-terminus of the encoded protein. The primers were then used to amplify the ORF from one of the active full-length Selaginella clones. The resulting PCR product was then cloned into the GENEWARE vector pDN4 between the PacI and AvrII sites for expression in planta. The resulting clone, pLSB2225, was sequenced to confirm that the gene had been inserted correctly, and then transcribed in vitro followed by inoculation of the infectious transcripts onto *N. benthamiana* plants. Seven days post inoculation, infected plant extracts were made as above and assayed for supercoiled DNA nicking and digestion activity to confirm the activity of the cloned enzyme.

Each supercoiled DNA nicking assay was performed in a reaction containing 0.5 micrograms of a supercoiled plasmid prep of a pUC19-derivative in 1×NEB *E. coli* DNA ligase buffer in the presence of 50 mM KCl in a total volume of 10 microliters. The amounts of plant extract added to the reactions were 0.2 microliter, 0.04 microliter, 0.008 microliter, or 0.0016 microliter, incubated at 37° C. for 30 minutes, and run on a 0.8% TAE-agarose gel in the presence of Gelstar fluorescent DNA staining reagent. Little or no nicking activity was detected in uninfected plant extracts whereas extracts from plants infected with the GENEWARE-Selaginella construct pLSB2225 showed appreciable amounts of activity against the plasmid DNA substrate.

After positive results were obtained in that assay, extracts of pLSB2225 infected plants were used in a GRAMMR shuffling experiment to test the ability of this enzyme to operate as a component of the mismatch resolution reaction in place of the GENEWARE-produced CEL I enzyme of celery origin.

EXAMPLE 14

Use of RES I in the GRAMMR Reaction

This example teaches that RES I can be used in place of native CEL I enzyme purified from celery in Genetic Reassortment By DNA Mismatch Resolution without any noticeable change in results.

GRAMMR shuffling was performed between the wild-type *Aequorea victoria* GFP gene (Prasher, et al., Gene 111 (92)229) in a pBS derivative (Stratagene, La Jolla, Calif.) encoded by pBSWTGFP (SEQ ID NO:03) and a variant with mutations to increase fluorescence intensity in *E. coli*, and to alter the emission wavelength to blue light emission (Crameri, et al., Nat Biotechnol 14(96)315; Heim et al., PNAS91(94)12501; Yang, et al., J Biol Chem 273(98)8212). This variant gene, encoded by the plasmid pBSC3BFP, as shown in FIG. 5 (SEQ ID NO: 32), encodes a fluorescent protein that emits bright blue light when excited by longwave UV light.

The GRAMMR reactions were performed on GFP/c3BFP heteroduplexes in a circular, double-stranded plasmid DNA context. The circular, whole-plasmid heteroduplex DNA substates were prepared by first linearizing pBSWTGFP (SEQ ID NO:03) and pBSC3BFP (FIG. 5, SEQ ID NO:17) by digestion with Kpn I and NgoM IV, respectively, then purifying the digested DNA using DNA spin columns. Next, 200 nanograms of each of the two linearized plasmids were mixed and brought to 1×SSPE (180 nM NaCl, 10 mM $NaH_2PO_4$, 1 mM EDTA at pH 7.4) in a volume of 20 microliters. The mixture was then incubated at 95 degrees Celsius for 4 minutes, plunged into icewater where it remained for 10 minutes prior to incubation at 37 degrees Celsius. After 30 minutes, the annealed DNA sample was then transferred back to ice where it was held until use in GRAMMR reactions.

Two independent series of shuffling reactions were performed to compare CEL I with RES I in their abilities to facilitate sequence shuffling by GRAMMR. Each GRAMMR reaction contained 1 unit of T4 DNA polymerase, 2 units of *E. coli* DNA ligase, and 5 nanomoles of each dNTP in 1×NEB *E. coli* ligase buffer supplemented with KCl to 50 mM. Two separate enzyme dilution series were then performed. To each of two series of tubes containing aliquots of the above cocktail, one microliter aliquots of GENEWARE-expressed CEL I or RES I extracts at dilutions of 1/3, 1/9, 1/27, 1/81, or 1/243 were added. An endonuclease-free control reaction was also prepared. To each of the reactions, one microliter aliquots containing 20 nanograms of the annealed DNA heteroduplex substrate were added and the reactions incubated at room temperature for one hour and on ice for 30 minutes prior to transformation into competent *E. coli*.

Green fluorescent protein (GFP) and blue fluorescent protein (BFP) could be visualized in the resulting colonies by long wave UV illumination. The parental wild-type GFP has dim green fluorescence, and the parental c3BFP gave bright blue fluorescence. In the genes encoding these fluorescent proteins, the sequences that determine the emission color and those that govern fluorescence intensity are at different positions from one another. If is expected that DNA shuffling would result in the "de-linking" of the sequences that determine the emission color from those that govern fluorescence intensity. As a consequence, the resultant progeny would be expected to exhibit reassortment of the functional properties of emission color and intensity. Therefore a measure of the extent of the DNA shuffling that had taken place in each reaction could be scored by examining the color and intensity of fluorescence from the bacterial colonies on the corresponding plates. In the zero-nuclease control, only dim green and bright blue colonies were observed. However, on plates with cells transformed with DNAs from the reactions containing either CEL I or RES I, some bright green as well as some dim blue colonies were observed, indicating that shuffling of DNA sequences had taken place. DNA sequence analysis confirmed that this was indeed the case and that on average, the recovery of shuffled clones was greater than 85% for both CEL I and RES I and that the number and distribution of information transfer events was similar for both enzymes. However, it appeared that the activity of RES I in this experiment was several-fold higher than that of CEL I, as indicated by the low transformation efficiency of reactions treated with the higher concentrations of the RES I preparation.

EXAMPLE 15

Molecular Breeding of Highly Divergent Tobamovirus 30K Genes in Viral Vectors Using Plasmid-on-Plasmid Genetic Reassortment By DNA Mismatch Resolution (POP GRAMMR)

Example 10 taught the reassortment of movement protein (MP) genes from several divergent strains of tobamovirus (approximately 75% identical; cloned into the pGENEWARE-MP-Avr-Pac vector) using Genetic Reassortment by DNA Mismatch Resolution (GRAMMR). This example teaches the use of Plasmid-on-plasmid GRAMMR (POP GRAMMR) for reasserting even more highly divergent species.

Starting parental MP genes from the tobamoviruses TMV-Cg (FIG. 6, SEQ ID NO:18), TMV-Ob (FIG. 7, SEQ ID NO:19), TMV-U2 (FIG. 8, SEQ ID NO:20), TMV-U1 (SEQ ID NO:09), and tomato mosaic virus (TOMV) (SEQ ID NO:10) were used. The plasmid of pGENEWARE-ToMV MP was linearized by digestion with Sma I. The plasmids of pGENEWARE containing the MP genes from either TMV-Cg, TMV-Ob, TMV-U2, or TMV-U1 were digested with Stu I. The digested pGENEWARE-MP constructs were purified using DNA spin columns. The following heterduplex pairs were generated: pGENEWARE-Cg MP and pGENEWARE-ToMV MP, pGENEWARE-TMV-Ob MP and pGENEWARE-ToMV MP, pGENEWARE-TMV-U2 MP and pGENEWARE-ToMV MP, pGENEWARE-TMV-U1 MP and pGENEWARE-TOMV MP. The heteroduplexes of these MP gene sequences are approximately 47%, 58%, 62%, and 75% identical, respectively. Heteroduplex DNA was generated by mixing 200 nanograms of each of the two linearized plasmids in 1×SSPE (180 mM NaCl, 10 mM $NaH_2PO_4$, 1 mM EDTA, at pH 7.4) in a volume of 20 microliters. The mixture was incubated at 95 degrees Celsius for 4 minutes, plunged into ice water where it remained for 10 minutes prior to incubation at 37 degrees Celsius. After 30 minutes, the annealed DNA sample was then transferred back to ice where it was held until use in GRAMMR reactions.

Each 10 microliter GRAMMR reaction contained 1 unit of T4 DNA polymerase, 2 units of *E. coli* DNA ligase, and 0.5 mM of each dNTP in 1×NEB *E. coli* DNA ligase buffer supplemented with KCl to 50 mM. A one microliter aliquot of CEL I (diluted 1/3, 1/9, 1/27, 1/81, 1/243, or 1/729) was next added. An endonuclease-free control reaction was also prepared. To each of the reactions, a one microliter aliquot containing 20 nanograms of the annealed DNA heteroduplex substrate was added and the reactions were incubated at room temperature for one hour and on ice for 30 minutes prior to transformation into competent *E. coli.*

DNA sequence analysis was performed from both directions, and the sequence data showed that a significant number of clones derived from the GRAMMR-treated material were reasserted sequences containing information from both parental movement protein gene sequences. The DNA sequences of several exemplary GRAMMR pGENEWARE-MP clones are shown as follows, TMV-Cg/ToMV clones, FIG. 9, SEQ ID NO:21, and FIG. 10, SEQ ID NO:22; TMV-Ob/ToMV clones, FIG. 11, SEQ ID NO:23, and FIG. 12, SEQ ID NO:24; TMV-U2/ToMV clones, FIG. 13, SEQ ID NO:25, and FIG. 14, SEQ ID NO:26; and TMV-U1/ToMV clones, FIG. 15, SEQ ID NO:27, and FIG. 16, SEQ ID NO:28.

EXAMPLE 16

GRAMMR with 3' to 5' Exonuclease and 5' to 3' Polymerase Activities on Separate Enzymes This example teaches a GRAMMR reaction using appropriate enzymes such that the 3' to 5' exonuclease and the 5' to 3' polymerase activities are present on separate enzymes.

GRAMMR reassortment is performed between the wild-type *Aequorea victoria* GFP gene (Prasher, et al., Genell1 (92)229) in a pBS derivative (Stratagene, La Jolla, Calif.) encoded by pBSWTGFP (SEQ ID NO:03) and a variant with mutations to increase fluorescence intensity in *E. coli*, and to alter the emission wavelength to blue light emission (Crameri, et al., Nat Biotechnol 14(96)315; Heim et al., PNAS91(94)12501; Yang, et al., J Biol Chem 273(98)8212). This variant gene, encoded by the plasmid pBSC3BFP (SEQ ID NO:17), encodes a fluorescent protein that emits bright blue light when excited by longwave UV light.

The GRAMMR reactions are performed on GFP/c3BFP heteroduplexes in a circular, double-stranded plasmid DNA context. The circular, whole-plasmid heteroduplex DNA substates are prepared by first linearizing pBSWTGFP (SEQ ID NO:03) and pBSC3BFP (SEQ ID NO:17) by digestion with Kpn I and NgoM IV, respectively, then purifying the digested DNA using DNA spin columns. Next, 200 nanograms of each of the two linearized plasmids are mixed and brought to 1×SSPE (180 nM NaCl, 10 mM NaH2PO4, 1 mM EDTA at pH 7.4) in a volume of 20 microliters. The mixture is then incubated at 95 degrees Celsius for 4 minutes, plunged into icewater where it remains for 10 minutes prior to incubation at 37 degrees Celsius. After 30 minutes, the annealed DNA sample is then transferred back to ice where it is held until use in GRAMMR reactions.

Two independent series of reassortment reactions are performed to compare CEL I with RES I in their abilities to facilitate sequence reassortment by GRAMMR. Each GRAMMR reaction contains 1 unit of KlenTaq polymerase, 5 units of *E. coli* Exonuclease III, 2 units of *E. coli* DNA ligase, and 5 nanomoles of each dNTP in 1×NEB *E. coli* ligase buffer supplemented with KCl to 50 mM. Two separate enzyme dilution series are then performed. To each of two series of tubes containing aliquots of the above cocktail, one microliter aliquots of GENEWARE-expressed CEL I or RES I extracts at dilutions of 1/3, 1/9, 1/27, 1/81, or 1/243 are added. An endonuclease-free control reaction is also prepared. To each of the reactions, one microliter aliquots containing 20 nanograms of the annealed DNA heteroduplex substrate are added and the reactions incubated at room temperature for one hour and on ice for 30 minutes prior to transformation into competent *E. coli.*

Green fluorescent protein (GFP) and blue fluorescent protein (BFP) is visualized in the resulting colonies by long wave UV illumination. The parental wild-type GFP gives dim green fluorescence, and the parental c3BFP gives bright blue fluorescence. In the genes encoding these fluorescent proteins, the sequences that determine the emission color and those that govern fluorescence intensity are at different positions from one another. If is expected that DNA reassortment would result in the "de-linking" of the sequences that determine the emission color from those that govern fluorescence intensity. As a consequence, the resultant progeny would be expected to exhibit reassortment of the functional properties of emission color and intensity. Therefore a measure of the extent of the DNA reassortment that had taken place in each reaction can be scored by examining the color and intensity of fluorescence from the bacterial colonies on the corresponding plates.

EXAMPLE 17

GRAMMR on Linearized DNA Substrate Using Endonucleases that Cleave within a Selectable Marker This example teaches a GRAMMR process where DNA substrate molecules are linearized with restriction endonucleases that cleave within a selectable marker gene.

GRAMMR reassortment is performed between the wild-type Aequorea victoria GFP gene (Prasher, et al., Genell1 (92)229) in a pBS derivative (Stratagene, La Jolla, Calif.) encoded by pBSWTGFP (SEQ ID NO:03) and a variant with mutations to increase fluorescence intensity in $E.\ coli$, and to alter the emission wavelength to blue light emission (Crameri, et al., Nat Biotechnol 14 (96) 315; Heim et al., PNAS91 (94)12501; Yang, et al., J Biol Chem 273 (98)8212). This variant gene, encoded by the plasmid pBSC3BFP (SEQ ID NO:17), encodes a fluorescent protein that emits bright blue light when excited by longwave UV light.

The GRAMMR reactions are performed on GFP/c3BFP heteroduplexes in a circular, double-stranded plasmid DNA context. The circular, whole-plasmid heteroduplex DNA substates are prepared by first linearizing pBSWTGFP (SEQ ID NO:03) and pBSC3BFP (SEQ ID NO:17) by digestion with Ahd I and Bcg I, respectively, then purifying the digested DNA using DNA spin columns. Next, 200 nanograms of each of the two linearized plasmids are mixed and brought to 1×SSPE (180 nM NaCl, 10 mM NaH2PO4, 1 mM EDTA at pH 7.4) in a volume of 20 microliters. The mixture is then incubated at 95 degrees Celsius for 4 minutes, plunged into icewater where it remains for 10 minutes prior to incubation at 37 degrees Celsius. After 30 minutes, the annealed DNA sample is then transferred back to ice where it is held until use in GRAMMR reactions.

Two independent series of reassortment reactions are performed to compare CEL I with RES I in their abilities to facilitate sequence reassortment by GRAMMR. Each reaction is first treated for 10 minutes at room-temperature with 1 unit of T4 DNA polymerase In the presence of 5 nanomoles of each dNTP in 1×NEB $E.\ coli$ ligase buffer supplemented with KCl to 50 mM. Subsequently, 2 units of $E.\ coli$ DNA ligase are added. Two separate enzyme dilution series are then performed. To each of two series of tubes containing aliquots of the above cocktail, one microliter aliquots of GENEWARE-expressed CEL I or RES I extracts at dilutions of 1/3, 1/9, 1/27, 1/81, or 1/243 are added. An endonuclease-free control reaction is also prepared. To each of the reactions, one microliter aliquots containing 20 nanograms of the annealed DNA heteroduplex substrate are added and the reactions incubated at room temperature for one hour and on ice for 30 minutes prior to transformation into competent $E.\ coli$.

Green fluorescent protein (GFP) and blue fluorescent protein (BFP) is visualized in the resulting colonies by long wave UV illumination. The parental wild-type GFP gives dim green fluorescence, and the parental c3BFP gives bright blue fluorescence. In the genes encoding these fluorescent proteins, the sequences that determine the emission color and those that govern fluorescence intensity are at different positions from one another.

It is expected that DNA reassortment would result in the "de-linking" of the sequences that determine the emission color from those that govern fluorescence intensity. As a consequence, the resultant progeny would be expected to exhibit reassortment of the functional properties of emission color and intensity. Therefore a measure of the extent of the DNA reassortment that had taken place in each reaction can be scored by examining the color and intensity of fluorescence from the bacterial colonies on the corresponding plates.

EXAMPLE 18

Alternative Method for DNA Shuffling by Using DNAase I and pol I

This experiment replicates those described by Moore et al., WO 02/24953 in which heteroduplex DNA is treated with a non-specific endonuclease (DNase I). Subsequently, heteroduplex DNA is contacted with a nick-translating DNA polymerase (Pol I) which nick-translates on the heteroduplex DNA to bring-about a form of DNA shuffling.

GFP and c3BFP genes were used in the experiment. Heteroduplexes between the GFP/c3BFP genew were generated in a circular, double-strnaded plasmid DNA context. The circular, whole-plasmid heteroduplex DNA substrates were prepared by first linearizing pBSWTGFP (SEQ ID NO:31) and pBSC3BFP (FIG. 5, SEQ ID NO: 32) by digestion with Kpn I and NgoM IV, respectively, then purifying the digested DNA using DNA spin columns. Next, 125 nanograms of each of the two linearized plasmids were mixed in a volume of 10 microliters and incubated at 95 degrees Celsius for 4 minutes, plunged into ice water for 10 minutes. Subsequently, 1.1 ul of 10×SSPE (1800 mM NaCl, 100 mM $NaH_2PO_4$, 10 mM EDTA at pH 7.4) was added prior to incubation at 37 degrees Celsius After 30 minutes, the annealed DNA sample was then transferred back to ice. The sample was run out on a 2% low melt agarose gel and the nicked-circular heteroduplex band was gel isolated and purified using a DNA spin column.

The following reagents were mixed on ice: 5.4 microliters water; 1.0 microliters 10×NT buffer (0.5M Tris-HCl pH 7.5; 0.1M $MgCl_2$; 10 mM dithiothreitol [DTT]; 0.5 mg/mL BSA); 0.4 microliters Pol I (4 units), 1.8 microliters 2 mM dNTP, 0.4 microliters DNase I (0.18 units; diluted from 10 units/ul stock in 1×NT buffer in 50% glycerol); and one microliter heteroduplex DNA (20 ng). Control reactions in which lacked either or both DNase I or Pol I were also set up. All reactions were carried out at 14 degrees Celsius for 15 mins and stopped with 0.5 microliters 500 mM EDTA. One microliter of the reaction was transformed into competent $E.\ coli$.

DNA sequence analysis was performed from both directions. In reactions containing both DNase I and Pol i, results showed that 44% of the clones analyzed were chimeras of the two parent genes. Each clone contained only one crossover site. In addition, all these chimeras were made up of c3BFP sequences upstream of the crossover site and wild-type GFP sequences downstream of the crossover site. These marked polarity effects and exclusively single-crossover chimeras are consistent with what would be expected from a purely nick-translation based mechanism of DNA shuffling. In the control reaction lacking DNase I, 34% of the clones analyzed were chimeras of the two parent genes and also exhibited the same polarity effect as observed with the DNase I plus Pol I reaction. In the control reaction lacking Pol I, 17% of the clones analyzed were chimeras of the two parent genes. In the control reaction lacking both DNase I and Pol I, 10% of the clones analyzed were chimeras of the two parent genes.

EXAMPLE 19

Use of Varying Ratios of DNA Polymerases and DNA Ligase to Regulate the Granularity of the Genetic Reassortment by DNA Mismatch Resolution Reaction This experiment teaches that the length of sites of information transfer (granularity) can be regulated by manipulating the concentrations of certain components of a GRAMMR reaction. The longer the blocks of sequence information transferred, the coarser the granularity. The shorter the blocks of sequence information transferred, the finer the granularity. The GFP and c3BFP genes were used in the experiment. Heteroduplexes between the GFP/c3BFP genes were generated in a circular, double-stranded plasmid DNA context as described in Example 14. Matrix experiments were performed in which the relative concentration of DNA polymerase and DNA ligase in the GRAMMR was varied. NEB *E. coli* DNA polymerase I (Pol I, which after proofreading, can nick-translate from sites on CEL I nicking) and NEB *E. coli* DNA ligase were used. These two enzymes were diluted from the stock concentration in 1× *E. coli* ligase buffer. The concentrations of Pol I used were 0.01, 0.1, 1.0, and 5.0 units/uL. The concentrations of *E. coli* DNA ligase used were 0.0, 0.02, 0.2, and 2.0 units/uL. In all, the matrix contained 16 individual reactions. Each reaction contained 0.5 mM of each dNTP, 1×NEB *E. coli* ligase buffer supplemented with KCl to 50 mM, one microliter of diluted *E. coli* DNA ligase, one microliter of diluted Pol I, one microliter of a GENEWARE®-expressed CEL I preparation (containing 27 ng protein), and 20 nanograms of the annealed DNA heteroduplex. The reactions were incubated at room temperature for one hour before direct transformation into competent *E. coli*.

DNA sequence analysis was performed from both directions on a number of randomly-selected clones, and the sequence data showed varying degrees of granularity and crossover frequency among progeny clones depending on the relative concentration of Pol I to DNA ligase used. For instance, in reactions in which no DNA ligase and 1.0 units of Pol I was used, progeny clones showed a larger granularity with only one crossover between the parental clones. In reactions in which 0.2 units of DNA ligase and 0.1 units of Pol I was used, the granularity was finer with an average of approximately three crossovers between parental clones. In reactions in which 2.0 units of DNA ligase and 0.1 units of Pol 1 was used, the granularity was relatively much finer with an average of approximately seven crossovers between parental clones.

From this experiment, a trend emerged where the higher the ligase: Pol I ratio, the finer the granularity. When the concentration of ligase is low in relation to Pol I, it is likely that the Pol I enzyme can nick-translate for longer distances before the nick becomes sealed by the ligase. However, as the concentration of ligase is increased, the potential for nick-sealing is increased, which will tend to terminate nick-translation events earlier, thus shortening the average length of the sites of information transfer.

EXAMPLE 20

Plasmid-on-Plasmid Zonal Mutagenesis Using Genetic Reassortment by DNA Mismatch Resolution (POP zmGRAMMR) of GFP Plasmids This example teaches that random or semi-random mutations can be incorporated at and in the immediate vicinity of mismatched residues by performing GRAMMR in the presence of nucleotide analogs that have multi base-pairing potential. The end result is a population of shuffled genes with random mutations concentrated in regions of heterogeneity between the starting genes.

Unlike conventional GRAMMR methods, zonal mutagenesis GRAMMR requires only one nucleotide pair mismatch in the heteroduplex. Instead of resolving diversity between the two polynucleic acids in the heteroduplex, one is increasing diversity. One of the polynucleotides need not be full length and may be an oligonucleotide sufficiently long to hybridize and still have one base mismatched. If is partially complementary to the desired polynucleotide strand. In this manner, one can direct mutagenesis to a particular zone using a synthetic oligo or polynucleotide without ever having full length parent strands with a mismatch at or near the zone.

The mutagenesis zone on each strand forming the heteroduplex includes the mismatched base pair and a region within 1 to about 50 nucleotides upstream and downstream on both strands. More preferably, the mutagenesis zone includes the mismatched base pair and 1 to about 10 nucleotides on either side of the mismatch.

The nucleotide analogue may be any one or a combination of plural nucleotide analogues which will induce a change in base in the same or a complementary strand immediately or after replication of the polynucleotide strand incorporating the nucleotide analogue or a complementary strand. The nucleotide analogue may also induce an insertion or deletion of one or more nucleotides on either strand. A large number of nucleotide analogues are known per se.

Heteroduplexes between the GFP/c3BFP genes were generated in a circular, double-stranded plasmid DNA context as described in Example 14. Several zmGRAMMR reactions were set up in which the ratio of ligase to polymerase and analog nucleotide to dNTP ratios varied. The zmGRAMMR reactions contained the following: 0.1 unit of Pol I DNA polymerase; 2 or 10 units of *E. coli* DNA ligase; 0 or 0.5 mM of 2'-deoxy-P-nucleoside-5'-triphosphate (dPTP); 0 or 0.5 mM 8-oxo-2'-deoxyguanosine-5'-triphosphate (8-oxo-dGTP); 0, 5, 25, 50, or 500 nM of each dNTP; and 1×NEB *E. coli* ligase buffer supplemented with KCl to 50 mM. Reactions were also set up in which 1 unit of T4 DNA polymerase or 5 units of Klenow polymerase was used in lieu of Pol I. A one microliter aliquot of a GENEWARE-expressed RES I preparation containing 2 ng protein was then added. An endonuclease-free control reaction was also prepared. Finally, 20 nanograms of the annealed DNA heteroduplex substrate was added and the complete reaction was incubated at 25° C. for one hour. The zmGRAMMR treated heteroduplex was then column purified and transformed into competent *E. coli*.

The resulting colonies were examined under UV illumination. ZmGRAMMR reactions with high concentrations of nucleotide analog relative to dNTPs gave rise to a high proportion of non-fluorescent colonies, whereas colonies resulting from control reactions performed in the absence of analog showed few, if any non-fluorescent colonies. Reactions containing Klenow polymerase gave rise to very few colonies, all of which were non-fluorescent. DNA sequence analysis performed on a number of randomly-picked clones showed that a significant number of clones derived from nucleotide analog-containing GRAMMR reactions contained mutations (i.e. sequences unrelated to both parents) focused at or very near sites of mismatch between the GFP/c3BFP genes. Reactions containing a higher ratio of nucleotide-analog to dNTP yielded a higher percentage of clones containing mutations. ZmGRAMMR reactions using Klenow were largely unsuccessful, as few colonies were recovered, even for control reactions with no analogs. Clones derived from zmGRAMMR reactions using T4 DNA polymerase showed mutations that were more focused to sites of mismatch than those from the Pol I containing reactions. This result was as expected, since T4 DNA polymerase does not nick-translate, and thus, is expected in incorporate analogs only at or very near the site of the excised mismatch.

As the base analogs are incorporated during the GRAMMR reaction, these mutations serve to mark the tract of the polymerase during the course of the reaction. By varying the ratios of ligase to Pol I as taught in example 18, the width of those mutated tracts can also be manipulated.

SEQUENCE LISTING

<160> NUMBER OF SEQ ID NOS: 42

<210> SEQ ID NO 1
<211> LENGTH: 10600
<212> TYPE: DNA
<213> ORGANISM: Artificial
<220> FEATURE:
<223> OTHER INFORMATION: TMV infectious clone containing CEL I gene

<400> SEQUENCE: 1

```
gtatttttac aacaattacc aacaacaaca aacaacaaac aacattacaa ttactattta      60
caattacaat ggcatacaca cagacagcta ccacatcagc tttgctggac actgtccgag     120
gaaacaactc cttggtcaat gatctagcaa agcgtcgtct ttacgacaca gcggttgaag     180
agtttaacgc tcgtgaccgc aggcccaagg tgaacttttc aaaagtaata agcgaggagc     240
agacgcttat tgctacccgg gcgtatccag aattccaaat tacattttat aacacgcaaa     300
atgccgtgca ttcgcttgca ggtggattgc gatctttaga actggaatat ctgatgatgc     360
aaattcccta cggatcattg acttatgaca taggcggaa ttttgcatcg catctgttca     420
agggacgagc atatgtacac tgctgcatgc ccaacctgga cgttcgagac atcatgcggc     480
acgaaggcca gaaagacagt attgaactat acctttctag gctagagaga ggggggaaaa     540
cagtccccaa cttccaaaag gaagcatttg acagatacgc agaaattcct gaagacgctg     600
tctgtcacaa tacttttccag acaatgcgac atcagccgat gcagcaatca ggcagagtgt     660
atgccattgc gctacacagc atatatgaca taccagccga tgagttcggg gcggcactct     720
tgaggaaaaa tgtccatacg tgctatgccg ctttccactt ctctgagaac ctgcttcttg     780
aagattcata cgtcaatttg gacgaaatca acgcgtgttt tcgcgcgat ggagacaagt     840 tgacctttc ttttgcatca gagagtactc ttaattattg tcatagttat tctaatattc     900
ttaagtatgt gtgcaaaact tacttcccgg cctctaatag agaggtttac atgaaggagt     960
ttttagtcac cagagttaat acctggtttt gtaagttttc tagaatagat acttttcttt    1020
tgtacaaagg tgtggcccat aaaagtgtag atagtgagca gttttatact gcaatggaag    1080
acgcatggca ttacaaaaag actcttgcaa tgtgcaacag cgagagaatc ctccttgagg    1140
attcatcatc agtcaattac tggtttccca aaatgaggga tatggtcatc gtaccattat    1200
tcgacatttc tttggagact agtaagagga cgcgcaagga agtcttagtg tccaaggatt    1260
tcgtgtttac agtgcttaac cacattcgaa cataccaggc gaaagctctt acatacgcaa    1320
atgttttgtc ctttgtcgaa tcgattcgat cgagggtaat cattaacggt gtgacagcga    1380
ggtccgaatg ggatgtggac aaatctttgt tacaatcctt gtccatgacg ttttacctgc    1440
atactaagct tgccgttcta aaggatgact tactgattag caagttagt ctcggttcga    1500
```

```
aaacggtgtg ccagcatgtg tgggatgaga tttcgctggc gtttgggaac gcatttccct      1560
ccgtgaaaga gaggctcttg aacaggaaac ttatcagagt ggcaggcgac gcattagaga      1620
tcagggtgcc tgatctatat gtgaccttcc acgacagatt agtgactgag tacaaggcct      1680
ctgtggacat gcctgcgctt gacattagga agaagatgga agaaacggaa gtgatgtaca      1740
atgcactttc agagttatcg gtgttaaggg agtctgacaa attcgatgtt gatgtttttt      1800
cccagatgtg ccaatctttg gaagttgacc caatgacggc agcgaaggtt atagtcgcgg      1860
tcatgagcaa tgagagcggt ctgactctca catttgaacg acctactgag gcgaatgttg      1920
cgctagcttt acaggatcaa gagaaggctt cagaaggtgc tttggtagtt acctcaagag      1980
aagttgaaga accgtccatg aagggttcga tggccagagg agagttacaa ttagctggtc      2040
ttgctggaga tcatccggag tcgtcctatt ctaagaacga ggagatagag tctttagagc      2100
agtttcatat ggcaacggca gattcgttaa ttcgtaagca gatgagctcg attgtgtaca      2160
cgggtccgat taaagttcag caaatgaaaa actttatcga tagcctggta gcatcactat      2220
ctgctgcggt gtcgaatctc gtcaagatcc tcaaagatac agctgctatt gaccttgaaa      2280
cccgtcaaaa gtttggagtc ttggatgttg catctaggaa gtggttaatc aaaccaacgg      2340
ccaagagtca tgcatggggt gttgttgaaa cccacgcgag gaagtatcat gtggcgcttt      2400
tggaatatga tgagcagggt gtggtgacat gcgatgattg gagaagagta gctgtcagct      2460
ctgagtctgt tgtttattcc gacatggcga aactcagaac tctgcgcaga ctgcttcgaa      2520
acggagaacc gcatgtcagt agcgcaaagg ttgttcttgt ggacggagtt ccgggctgtg      2580
ggaaaaccaa agaaattctt tccagggtta attttgatga agatctaatt ttagtacctg      2640
ggaagcaagc cgcggaaatg atcagaagac gtgcgaattc ctcagggatt attgtggcca      2700
cgaaggacaa cgttaaaacc gttgattctt tcatgatgaa ttttgggaaa agcacacgct      2760
gtcagttcaa gaggttattc attgatgaag ggttgatgtt gcatactggt tgtgttaatt      2820
ttcttgtggc gatgtcattg tgcgaaattg catatgttta cggagacaca cagcagattc      2880
catacatcaa tagagtttca ggattcccgt accccgccca ttttgccaaa ttggaagttg      2940
acgaggtgga gacacgcaga actactctcc gttgtccagc cgatgtcaca cattatctga      3000
acaggagata tgagggcttt gtcatgagca cttcttcggt taaaaagtct gtttcgcagg      3060
agatggtcgg cggagccgcc gtgatcaatc cgatctcaaa acccttgcat ggcaagatcc      3120
tgacttttac ccaatcggat aaagaagctc tgctttcaag agggtattca gatgttcaca      3180
ctgtgcatga agtgcaaggc gagacatact ctgatgtttc actagttagg ttaaccccta      3240
caccagtctc catcattgca ggagacagcc acatgttttt ggtcgcattg tcaaggcaca      3300
cctgttcgct caagtactac actgttgtta tggatccttt agttagtatc attagagatc      3360
tagagaaact tagctcgtac ttgttagata tgtataaggt cgatgcagga acacaatagc      3420
aattacagat tgactcggtg ttcaaaggtt ccaatctttt tgttgcagcg ccaaagactg      3480
gtgatatttc tgatatgcag ttttactatg ataagtgtct cccaggcaac agcaccatga      3540
tgaataattt tgatgctgtt accatgaggt tgactgacat ttcattgaat gtcaaagatt      3600
gcatattgga tatgtctaag tctgttgctg cgcctaagga tcaaatcaaa ccactaatac      3660
ctatggtacg aacggcggca gaaatgccac gccagactgg actattggaa aatttagtgg      3720
cgatgattaa aaggaacttt aacgcacccg agtgtctgg catcattgat attgaaaata      3780
ctgcatcttt agttgtagat aagttttttg atagttattt gcttaaagaa aaagaaaaac      3840
```

```
caaataaaaa tgtttctttg ttcagtagag agtctctcaa tagatggtta gaaaagcagg    3900
aacaggtaac aataggccag ctcgcagatt ttgattttgt agatttgcca gcagttgatc    3960
agtacagaca catgattaaa gcacaaccca agcaaaaatt ggacacttca atccaaacgg    4020
agtacccggc tttgcagacg attgtgtacc attcaaaaaa gatcaatgca atatttggcc    4080
cgttgtttag tgagcttact aggcaattac tggacagtgt tgattcgagc agatttttgt    4140
ttttcacaag aaagacacca gcgcagattg aggatttctt cggagatctc gacagtcatg    4200
tgccgatgga tgtcttggag ctggatatat caaaatacga caaatctcag aatgaattcc    4260
actgtgcagt agaatacgag atctggcgaa gattgggttt tgaagacttc ttgggagaag    4320
tttggaaaca agggcataga aagaccaccc tcaaggatta taccgcaggt ataaaaactt    4380
gcatctggta tcaaagaaag agcggggacg tcacgacgtt cattggaaac actgtgatca    4440
ttgctgcatg tttggcctcg atgcttccga tggagaaaat aatcaaagga gccttttgcg    4500
gtgacgatag tctgctgtac tttccaaagg gttgtgagtt tccggatgtg caacactccg    4560
cgaatcttat gtggaatttt gaagcaaaac tgtttaaaaa acagtatgga acttttgcg    4620 gaagatatgt aatacatcac gacagaggat gcattgtgta ttacgatccc ctaaagttga    4680
tctcgaaact tggtgctaaa cacatcaagg attgggaaca cttggaggag ttcagaaggt    4740
ctctttgtga tgttgctgtt tcgttgaaca attgtgcgta ttacacacag ttggacgacg    4800
ctgtatggga ggttcataag accgcccctc caggttcgtt tgtttataaa agtctggtga    4860
agtatttgtc tgataaagtt cttttttagaa gtttgtttat agatggctct agttgttaaa    4920
ggaaaagtga atatcaatga gtttatcgac ctgacaaaaa tggagaagat cttaccgtcg    4980
atgtttaccc ctgtaaagag tgttatgtgt tccaaagttg ataaaataat ggttcatgag    5040
aatgagtcat tgtcagaggt gaaccttctt aaaggagtta agcttattga tagtggatac    5100
gtctgtttag ccggttttggt cgtcacgggc gagtggaact tgcctgacaa ttgcagagga    5160
ggtgtgagcg tgtgtctggt ggacaaaagg atggaaagag ccgacgaggc cactctcgga    5220
tcttactaca cagcagctgc aaagaaaaga tttcagttca aggtcgttcc caattatgct    5280
ataaccaccc aggacgcgat gaaaaacgtc tggcaagttt tagttaatat tagaaatgtg    5340
aagatgtcag cgggtttctg tccgctttct ctggagtttg tgtcggtgtg tattgtttat    5400
agaaataata taaaattagg tttgagagag aagattacaa acgtgagaga cggagggccc    5460
atggaactta cagaagaagt cgttgatgag ttcatggaag atgtccctat gtcgatcagg    5520
cttgcaaagt ttcgatctcg aaccggaaaa aagagtgatg tccgcaaagg gaaaaatagt    5580
agtaatgatc ggtcagtgcc gaacaagaac tatagaaatg ttaaggattt tggaggaatg    5640
agttttaaaa agaataattt aatcgatgat gattcggagg ctactgtcgc cgaatcggat    5700
tcgttttaaa tagatcttac agtatcacta ctccatctca gttcgtgttc ttgtcattaa    5760
ttaaatgacg cgattatatt ctgtgttctt tcttttgttg gctcttgtag ttgaaccggg    5820
tgttagagcc tggagcaaag aaggccatgt catgacatgt caaattgcgc aggatctgtt    5880
ggagccagaa gcagcacatg ctgtaaagat gctgttaccg gactatgcta atggcaactt    5940
atcgtcgctg tgtgtgtggc ctgatcaaat tcgacactgg tacaagtaca ggtggactag    6000
ctctctccat ttcatcgata cacctgatca agcctgttca tttgattacc agagagactg    6060
tcatgatcca catggaggga aggacatgtg tgttgctgga gccattcaaa atttcacatc    6120
tcagcttgga catttccgcc atggaacatc tgatcgtcga tataatatga cagaggcttt    6180 gttatttta tcccacttca tgggagatat tcatcagcct atgcatgttg gatttacaag    6240
```

```
tgatatggga ggaaacagta tagatttgcg ctggtttcgc cacaaatcca acctgcacca   6300
tgtttgggat agagagatta ttcttacagc tgcagcagat taccatggta aggatatgca   6360
ctctctccta caagacatac agaggaactt tacagagggt agttggttgc aagatgttga   6420
atcctggaag gaatgtgatg atatctctac ttgcgccaat aagtatgcta aggagagtat   6480
aaaactagcc tgtaactggg gttacaaaga tgttgaatct ggcgaaactc tgtcagataa   6540
atacttcaac acaagaatgc caattgtcat gaaacggata gctcagggtg gaatccgttt   6600
atccatgatt ttgaaccgag ttcttggaag ctccgcagat cattctttgg catgacctag   6660
gccagtagtt tggtttaaac ccaactgcga ggggtagtca agatgcataa taaataacgg   6720
attgtgtccg taatcacacg tggtgcgtac gataacgcat agtgttttc cctccactta    6780 aatcgaaggg ttgtgtcttg gatcgcgcgg gtcaaatgta tatggttcat atacatccgc   6840
aggcacgtaa taaagcgagg ggttcgggtc gaggtcggct gtgaaactcg aaaaggttcc   6900
ggaaaacaaa aagagatgg taggtaatag tgttaataat aagaaaataa ataatagtgg    6960
taagaaaggt ttgaaagttg aggaaattga ggataatgta agtgatgacg agtctatcgc   7020
gtcatcgagt acgttttaat caatatgcct tatacaatca actctccgag ccaatttgtt   7080
tacttaagtt ccgcttatgc agatcctgtg cagctgatca atctgtgtac aaatgcattg   7140
ggtaaccagt ttcaaacgca acaagctagg acaacagtcc aacagcaatt tgcggatgcc   7200
tggaaacctg tgcctagtat gacagtgaga tttcctgcat cggatttcta tgtgtataga   7260
tataattcga cgcttgatcc gttgatcacg gcgttattaa atagcttcga tactagaaat   7320
agaataatag aggttgataa tcaacccgca ccgaatacta ctgaaatcgt taacgcgact   7380
cagagggtag acgatgcgac tgtagctata agggcttcaa tcaataattt ggctaatgaa   7440
ctggttcgtg gaactggcat gttcaatcaa gcaagctttg agactgctag tggacttgtc   7500
tggaccacaa ctccggctac ttagctattg ttgtgagatt tcctaaaata aagtcactga   7560
agacttaaaa ttcagggtgg ctgataccaa atcagcagt ggttgttcgt ccacttaaat    7620
ataacgattg tcatatctgg atccaacagt taaaccatgt gatggtgtat actgtggtat   7680
ggcgtaaaac aacggaaaag tcgctgaaga cttaaaattc agggtggctg ataccaaaat   7740
cagcagtggt tgttcgtcca cttaaaaata acgattgtca tatctggatc caacagttaa   7800
accatgtgat ggtgtatact gtggtatggc gtaaacaac ggagaggttc gaatcctccc    7860
ctaaccgcgg gtagcggccc aggtacccgg atgtgttttc cggctgatg agtccgtgag    7920 gacgaaaccc ggcatgcaag cttggcgtaa tcatggtcat agctgtttcc tgtgtgaaat   7980
tgttatccgc tcacaattcc acacaacata cgagccggaa gcataaagtg taaagcctgg   8040
ggtgcctaat gagtgagcta actcacatta attgcgttgc gctcactgcc cgctttccag   8100
tcgggaaacc tgtcgtgcca gctgcattaa tgaatcggcc aacgcgcggg gagaggcggt   8160
ttgcgtattg ggcgctcttc cgcttcctcg ctcactgact cgctgcgctc ggtcgttcgg   8220
ctgcggcgag cggtatcagc tcactcaaag gcggtaatac ggttatccac agaatcaggg   8280
gataacgcag gaaagaacat gtgagcaaaa ggccagcaaa aggccaggaa ccgtaaaaag   8340
gccgcgttgc tggcgttttt ccataggctc cgcccccctg acgagcatca caaaaatcga   8400
cgctcaagtc agaggtggcg aaacccgaca ggactataaa gataccaggc gtttccccct   8460
ggaagctccc tcgtgcgctc tcctgttccg accctgccgc ttaccggata cctgtccgcc   8520
tttctccctt cgggaagcgt ggcgctttct catagctcac gctgtaggta tctcagttcg   8580
```

```
gtgtaggtcg ttcgctccaa gctgggctgt gtgcacgaac cccccgttca gcccgaccgc   8640
tgcgccttat ccggtaacta tcgtcttgag tccaacccgg taagacacga cttatcgcca   8700
ctggcagcag ccactggtaa caggattagc agagcgaggt atgtaggcgg tgctacagag   8760
ttcttgaagt ggtggcctaa ctacggctac actagaagga cagtatttgg tatctgcgct   8820
ctgctgaagc cagttacctt cggaaaaaga gttggtagct cttgatccgg caaacaaacc   8880
accgctggta gcggtggttt ttttgtttgc aagcagcaga ttacgcgcag aaaaaaagga   8940
tctcaagaag atcctttgat cttttctacg gggtctgacg ctcagtggaa cgaaaactca   9000
cgttaaggga ttttggtcat gagattatca aaaaggatct tcacctagat ccttttaaat   9060
taaaaatgaa gttttaaatc aatctaaagt atatatgagt aaacttggtc tgacagttac   9120
caatgcttaa tcagtgaggc acctatctca gcgatctgtc tatttcgttc atccatagtt   9180
gcctgactcc ccgtcgtgta gataactacg atacgggagg gcttaccatc tggccccagt   9240
gctgcaatga taccgcgaga cccacgctca ccggctccag atttatcagc aataaaccag   9300
ccagccggaa gggccgagcg cagaagtggt cctgcaactt tatccgcctc catccagtct   9360
attaattgtt gccgggaagc tagagtaagt agttcgccag ttaatagttt gcgcaacgtt   9420
gttgccattg ctacaggcat cgtggtgtca cgctcgtcgt ttggtatggc ttcattcagc   9480
tccggttccc aacgatcaag gcgagttaca tgatccccca tgttgtgcaa aaaagcggtt   9540
agctccttcg gtcctccgat cgttgtcaga agtaagttgg ccgcagtgtt atcactcatg   9600
gttatggcag cactgcataa ttctcttact gtcatgccat ccgtaagatg cttttctgtg   9660
actggtgagt actcaaccaa gtcattctga gaatagtgta tgcggcgacc gagttgctct   9720
tgcccggcgt caatacggga taataccgcg ccacatagca gaactttaaa agtgctcatc   9780
attggaaaac gttcttcggg gcgaaaactc tcaaggatct taccgctgtt gagatccagt   9840
tcgatgtaac ccactcgtgc acccaactga tcttcagcat cttttacttt caccagcgtt   9900
tctgggtgag caaaaacagg aaggcaaaat gccgcaaaaa agggaataag ggcgacacgg   9960
aaatgttgaa tactcatact cttcctttt  caatattatt gaagcattta tcagggttat  10020
tgtctcatga gcggatacat atttgaatgt atttagaaaa ataaacaaat aggggttccg  10080
cgcacatttc cccgaaaagt gccacctgac gtctaagaaa ccattattat catgacatta  10140
acctataaaa ataggcgtat cacgaggccc tttcgtctcg cgcgtttcgg tgatgacggt  10200
gaaaacctct gacacatgca gctcccggag acggtcacag cttgtctgta agcggatgcc  10260
gggagcagac aagcccgtca gggcgcgtca gcgggtgttg gcgggtgtcg ggctggctt   10320 aactatgcgg catcagagca gattgtactg agagtgcacc atatgcggtg tgaaataccg  10380
cacagatgcg taaggagaaa ataccgcatc aggcgccatt cgccattcag gctgcgcaac  10440
tgttgggaag ggcgatcggt gcgggcctct tcgctattac gccagctggc gaaaggggga  10500
tgtgctgcaa ggcgattaag ttgggtaacg ccagggtttt cccagtcacg acgttgtaaa  10560
acgacggcca gtgaattcaa gcttaatacg actcactata                        10600
```

<210> SEQ ID NO 2
<211> LENGTH: 10624
<212> TYPE: DNA
<213> ORGANISM: Artificial
<220> FEATURE:
<223> OTHER INFORMATION: TMV infectous clone containing CEL I gene fused
      to a 6HIS encoding sequence

<400

```
gtattttac  aacaattacc  aacaacaaca  aacaacaaac  aacattacaa  ttactattta    60
caattacaat  ggcatacaca  cagacagcta  ccacatcagc  tttgctggac  actgtccgag   120
gaaacaactc  cttggtcaat  gatctagcaa  agcgtcgtct  ttacgacaca  gcggttgaag   180
agtttaacgc  tcgtgaccgc  aggcccaagg  tgaacttttc  aaaagtaata  agcgaggagc   240
agacgcttat  tgctacccgg  gcgtatccag  aattccaaat  tacattttat  aacacgcaaa   300
atgccgtgca  ttcgcttgca  ggtggattgc  gatctttaga  actggaatat  ctgatgatgc   360
aaattcccta  cggatcattg  acttatgaca  taggcgggaa  ttttgcatcg  catctgttca   420
agggacgagc  atatgtacac  tgctgcatgc  ccaacctgga  cgttcgagac  atcatgcggc   480
acgaaggcca  gaaagacagt  attgaactat  acctttctag  gctagagaga  gggggaaaa    540 cagtccccaa  cttccaaaag  gaagcatttg  acagatacgc  agaaattcct  gaagacgctg   600
tctgtcacaa  tactttccag  acaatgcgac  atcagccgat  gcagcaatca  ggcagagtgt   660
atgccattgc  gctacacagc  atatatgaca  taccagccga  tgagttcggg  gcggcactct   720
tgaggaaaaa  tgtccatacg  tgctatgccg  cttccacct  ctctgagaac  ctgcttcttg    780
aagattcata  cgtcaatttg  gacgaaatca  acgcgtgttt  ttcgcgcgat  ggagacaagt   840 tgacctttc   ttttgcatca  gagagtactc  ttaattattg  tcatagttat  tctaatattc   900
ttaagtatgt  gtgcaaaact  tacttcccgg  cctctaatag  agaggtttac  atgaaggagt   960
ttttagtcac  cagagttaat  acctggtttt  gtaagttttc  tagaatagat  acttttctt   1020 tgtacaaagg  tgtggcccat  aaaagtgtag  atagtgagca  gttttatact  gcaatggaag  1080
acgcatggca  ttacaaaaag  actcttgcaa  tgtgcaacag  cgagagaatc  ctccttgagg  1140
attcatcatc  agtcaattac  tggtttccca  aaatgaggga  tatggtcatc  gtaccattat  1200
tcgacatttc  tttggagact  agtaagagga  cgcgcaagga  agtcttagtg  tccaaggatt  1260
tcgtgtttac  agtgcttaac  cacattcgaa  cataccaggc  gaaagctctt  acatacgcaa  1320
atgttttgtc  ctttgtcgaa  tcgattcgat  cgagggtaat  cattaacggt  gtgacagcga  1380
ggtccgaatg  ggatgtggac  aaatctttgt  tacaatcctt  gtccatgacg  ttttacctgc  1440
atactaagct  tgccgttcta  aaggatgact  tactgattag  caagtttagt  ctcggttcga  1500
aaacggtgtg  ccagcatgtg  tgggatgaga  tttcgctggc  gtttgggaac  gcatttccct  1560
ccgtgaaaga  gaggctcttg  aacaggaaac  ttatcagagt  ggcaggcgac  gcattagaga  1620
tcagggtgcc  tgatctatat  gtgaccttcc  acgacagatt  agtgactgag  tacaaggcct  1680
ctgtggacat  gcctgcgctt  gacattagga  agaagatgga  agaaacggaa  gtgatgtaca  1740
atgcactttc  agagttatcg  gtgttaaggg  agtctgacaa  attcgatgtt  gatgttttt   1800 cccagatgtg  ccaatctttg  gaagttgacc  caatgacggc  agcgaaggtt  atagtcgcgg  1860
tcatgagcaa  tgagagcggt  ctgactctca  catttgaacg  acctactgag  gcgaatgttg  1920
cgctagcttt  acaggatcaa  gagaaggctt  cagaaggtgc  tttggtagtt  acctcaagag  1980
aagttgaaga  accgtccatg  aagggttcga  tggccagagg  agagttacaa  ttagctggtc  2040
ttgctggaga  tcatccggag  tcgtcctatt  ctaagaacga  ggagatagag  tctttagagc  2100
agtttcatat  ggcaacggca  gattcgttaa  ttcgtaagca  gatgagctcg  attgtgtaca  2160
cgggtccgat  taaagttcag  caaatgaaaa  acttttatcg  tagcctggta  gcatcactat  2220
ctgctgcggt  gtcgaatctc  gtcaagatcc  tcaaagatac  agctgctatt  gaccttgaaa  2280
cccgtcaaaa  gtttggagtc  ttggatgttg  catctaggaa  gtggttaatc  aaaccaacgg  2340
ccaagagtca  tgcatggggt  gttgttgaaa  cccacgcgag  gaagtatcat  gtggcgcttt  2400
```

```
tggaatatga tgagcagggt gtggtgacat gcgatgattg gagaagagta gctgtcagct   2460
ctgagtctgt tgtttattcc gacatggcga aactcagaac tctgcgcaga ctgcttcgaa   2520
acggagaacc gcatgtcagt agcgcaaagg ttgttcttgt ggacggagtt ccgggctgtg   2580
ggaaaaccaa agaaattctt tccagggtta attttgatga agatctaatt ttagtacctg   2640
ggaagcaagc cgcggaaatg atcagaagac gtgcgaattc ctcagggatt attgtggcca   2700
cgaaggacaa cgttaaaacc gttgattctt tcatgatgaa ttttgggaaa agcacacgct   2760
gtcagttcaa gaggttattc attgatgaag ggttgatgtt gcatactggt tgtgttaatt   2820
ttcttgtggc gatgtcattg tgcgaaattg catatgttta cggagacaca cagcagattc   2880
catacatcaa tagagtttca ggattcccgt accccgccca ttttgccaaa ttggaagttg   2940
acgaggtgga gacacgcaga actactctcc gttgtccagc cgatgtcaca cattatctga   3000
acaggagata tgagggcttt gtcatgagca cttcttcggt taaaaagtct gtttcgcagg   3060
agatggtcgg cggagccgcc gtgatcaatc cgatctcaaa acccttgcat ggcaagatcc   3120 tgactttttac ccaatcggat aaagaagctc tgcttttcaag agggtattca gatgttcaca   3180
ctgtgcatga agtgcaaggc gagacatact ctgatgtttc actagttagg ttaacccta   3240 caccagtctc catcattgca ggagacagcc cacatgtttt ggtcgcattg tcaaggcaca   3300
cctgttcgct caagtactac actgttgtta tggatccttt agttagtatc attagagatc   3360
tagagaaact tagctcgtac ttgttagata tgtataaggt cgatgcagga acacaatagc   3420
aattacagat tgactcggtg ttcaaaggtt ccaatctttt tgttgcagcg ccaaagactg   3480
gtgatatttc tgatatgcag ttttactatg ataagtgtct cccaggcaac agcaccatga   3540
tgaataattt tgatgctgtt accatgaggt tgactgacat ttcattgaat gtcaaagatt   3600
gcatattgga tatgtctaag tctgttgctg cgcctaagga tcaaatcaaa ccactaatac   3660
ctatggtacg aacggcggca gaaatgccac gccagactgg actattggaa atttagtgg   3720 cgatgattaa aaggaacttt aacgcacccg agttgtctgg catcattgat attgaaaata   3780
ctgcatcttt agttgtagat aagttttttg atagttattt gcttaaagaa aaagaaaac   3840 caaataaaaa tgtttctttg ttcagtagag agtctctcaa tagatggtta gaaaagcagg   3900
aacaggtaac aataggccag ctcgcagatt ttgattttgt agatttgcca gcagttgatc   3960
agtacagaca catgattaaa gcacaaccca agcaaaaatt ggacacttca atccaaacgg   4020
agtacccggc tttgcagacg attgtgtacc attcaaaaaa gatcaatgca atatttggcc   4080
cgttgtttag tgagcttact aggcaattac tggacagtgt tgattcgagc agatttttgt   4140
ttttcacaag aaagacacca gcgcagattg aggatttctt cggagatctc gacagtcatg   4200
tgccgatgga tgtcttggag ctggatatat caaaatacga caaatctcag aatgaattcc   4260
actgtgcagt agaatacgag atctggcgaa gattgggttt tgaagacttc ttgggagaag   4320
tttggaaaca agggcataga aagaccaccc tcaaggatta taccgcaggt ataaaaactt   4380
gcatctggta tcaaagaaag agcgggggacg tcacgacgtt cattgaaaac actgtgatca   4440
ttgctgcatg tttggcctcg atgcttccga tggagaaaat aatcaaagga gcctttttgcg   4500 gtgacgatag tctgctgtac tttccaaagg gttgtgagtt tccggatgtg caacactccg   4560
cgaatcttat gtggaatttt gaagcaaaac tgtttaaaaa acagtatgga tacttttgcg   4620
gaagatatgt aatacatcac gacagaggat gcattgtgta ttcgatccc taaagttga   4680 tctcgaaact tggtgctaaa cacatcaagg attgggaaca cttggaggag ttcagaaggt   4740
```

```
ctctttgtga tgttgctgtt tcgttgaaca attgtgcgta ttacacacag ttggacgacg    4800
ctgtatggga ggttcataag accgcccctc caggttcgtt tgtttataaa agtctggtga    4860
agtatttgtc tgataaagtt cttttttagaa gtttgtttat agatggctct agttgttaaa   4920
ggaaaagtga atatcaatga gtttatcgac ctgacaaaaa tggagaagat cttaccgtcg    4980
atgtttaccc ctgtaaagag tgttatgtgt tccaaagttg ataaaataat ggttcatgag    5040
aatgagtcat tgtcagaggt gaaccttctt aaaggagtta agcttattga tagtggatac    5100
gtctgtttag ccggtttggt cgtcacgggc gagtggaact tgcctgacaa ttgcagagga    5160
ggtgtgagcg tgtgtctggt ggacaaaagg atggaaagag ccgacgaggc cactctcgga    5220
tcttactaca cagcagctgc aaagaaaaga tttcagttca aggtcgttcc caattatgct    5280
ataaccaccc aggacgcgat gaaaaacgtc tggcaagttt tagttaatat tagaaatgtg    5340
aagatgtcag cgggtttctg tccgctttct ctggagtttg tgtcggtgtg tattgtttat    5400
agaaataata taaaattagg tttgagagag aagattacaa acgtgagaga cggagggccc    5460
atggaactta cagaagaagt cgttgatgag ttcatggaag atgtccctat gtcgatcagg    5520
cttgcaaagt ttcgatctcg aaccggaaaa aagagtgatg tccgcaaagg gaaaaatagt    5580
agtaatgatc ggtcagtgcc gaacaagaac tatagaaatg ttaaggattt tggaggaatg    5640
agttttaaaa agaataattt aatcgatgat gattcggagg ctactgtcgc cgaatcggat    5700 tcgtttttaaa tagatcttac agtatcacta ctccatctca gttcgtgttc ttgtcattaa   5760
ttaaatgacg cgattatatt ctgtgttctt tcttttgttg gctcttgtag ttgaaccggg    5820
tgttagagcc tggagcaaag aaggccatgt catgacatgt caaattgcgc aggatctgtt    5880
ggagccagaa gcagcacatg ctgtaaagat gctgttaccg gactatgcta atggcaactt    5940
atcgtcgctg tgtgtgtggc ctgatcaaat tcgacactgg tacaagtaca ggtggactag    6000
ctctctccat ttcatcgata cacctgatca agcctgttca tttgattacc agagagactg    6060
tcatgatcca catggaggga aggacatgtg tgttgctgga gccattcaaa atttcacatc    6120
tcagcttgga catttccgcc atggaacatc tgatcgtcga tataatatga cagaggcttt    6180 gttatttta tcccacttca tgggagatat tcatcagcct atgcatgttg gatttacaag     6240
tgatatggga ggaaacagta tagatttgcg ctggtttcgc cacaaatcca acctgcacca    6300
tgtttgggat agagagatta ttcttacagc tgcagcagat taccatggta aggatatgca    6360
ctctctccta caagacatac agaggaactt tacagagggt agttggttgc aagatgttga    6420
atcctggaag gaatgtgatg atatctctac ttgcgccaat aagtatgcta aggagagtat    6480
aaaactagcc tgtaactggg gttacaaaga tgttgaatct ggcgaaactc tgtcagataa    6540
atacttcaac acaagaatgc caattgtcat gaaacggata gctcagggtg gaatccgttt    6600
atccatgatt ttgaaccgag ttcttggaag ctccgcagat cattctttgg caggaggtca    6660
ccatcaccat caccattgac ctaggccagt agtttggttt aaacccaact gcagggggta    6720
gtcaagatgc ataataaata acggattgtg tccgtaatca cacgtggtgc gtacgataac    6780
gcatagtgtt tttccctcca cttaaatcga agggttgtgt cttggatcgc gcgggtcaaa    6840
tgtatatggt tcatatacat ccgcaggcac gtaataaagc gaggggttcg ggtcgaggtc    6900
ggctgtgaaa ctcgaaaagg ttccggaaaa caaaaagag atggtaggta atagtgttaa     6960
taataagaaa ataataata gtggtaagaa aggtttgaaa gttgaggaaa ttgaggataa     7020
tgtaagtgat gacgagtcta tcgcgtcatc gagtacgttt taatcaatat gccttataca    7080
atcaactctc cgagccaatt tgtttactta agttccgctt atgcagatcc tgtgcagctg    7140
```

```
atcaatctgt gtacaaatgc attgggtaac cagtttcaaa cgcaacaagc taggacaaca     7200
gtccaacagc aatttgcgga tgcctggaaa cctgtgccta gtatgacagt gagatttcct     7260
gcatcggatt tctatgtgta tagatataat tcgacgcttg atccgttgat cacggcgtta     7320
ttaaatagct tcgatactag aaatagaata atagaggttg ataatcaacc cgcaccgaat     7380
actactgaaa tcgttaacgc gactcagagg gtagacgatg cgactgtagc tataagggct     7440
tcaatcaata atttggctaa tgaactggtt cgtggaactg gcatgttcaa tcaagcaagc     7500
tttgagactg ctagtggact tgtctggacc acaactccgg ctacttagct attgttgtga     7560
gatttcctaa aataaagtca ctgaagactt aaaattcagg gtggctgata ccaaaatcag     7620
cagtggttgt tcgtccactt aaatataacg attgtcatat ctggatccaa cagttaaacc     7680
atgtgatggt gtatactgtg gtatggcgta aaacaacgga aaagtcgctg aagacttaaa     7740
attcagggtg gctgatacca aaatcagcag tggttgttcg tccacttaaa ataacgatt     7800 gtcatatctg gatccaacag ttaaaccatg tgatggtgta tactgtggta tggcgtaaaa     7860
caacggagag gttcgaatcc tcccctaacc gcgggtagcg gcccaggtac ccggatgtgt     7920
tttccgggct gatgagtccg tgaggacgaa acccggcatg caagcttggc gtaatcatgg     7980
tcatagctgt ttcctgtgtg aaattgttat ccgctcacaa ttccacacaa catacgagcc     8040
ggaagcataa agtgtaaagc ctggggtgcc taatgagtga gctaactcac attaattgcg     8100
ttgcgctcac tgcccgcttt ccagtcggga aacctgtcgt gccagctgca ttaatgaatc     8160
ggccaacgcg cggggagagg cggtttgcgt attgggcgct cttccgcttc ctcgctcact     8220
gactcgctgc gctcggtcgt tcggctgcgg cgagcggtat cagctcactc aaaggcggta     8280
atacggttat ccacagaatc aggggataac gcaggaaaga acatgtgagc aaaaggccag     8340
caaaaggcca ggaaccgtaa aaaggccgcg ttgctggcgt ttttccatag gctccgcccc     8400
cctgacgagc atcacaaaaa tcgacgctca agtcagaggt ggcgaaaccc gacaggacta     8460
taaagatacc aggcgtttcc ccctggaagc tccctcgtgc gctctcctgt tccgaccctg     8520
ccgcttaccg gatacctgtc cgcctttctc ccttcgggaa gcgtggcgct ttctcatagc     8580
tcacgctgta ggtatctcag ttcggtgtag gtcgttcgct ccaagctggg ctgtgtgcac     8640
gaaccccccg ttcagcccga ccgctgcgcc ttatccggta actatcgtct tgagtccaac     8700
ccggtaagac acgacttatc gccactggca gcagccactg gtaacaggat tagcagagcg     8760
aggtatgtag gcggtgctac agagttcttg aagtggtggc ctaactacgg ctacactaga     8820
aggacagtat ttggtatctg cgctctgctg aagccagtta ccttcggaaa aagagttggt     8880
agctcttgat ccggcaaaca aaccaccgct ggtagcggtg gtttttttgt ttgcaagcag     8940
cagattacgc gcagaaaaaa aggatctcaa gaagatcctt tgatcttttc tacggggtct     9000
gacgctcagt ggaacgaaaa ctcacgttaa gggattttgg tcatgagatt atcaaaaagg     9060
atcttcacct agatcctttt aaattaaaaa tgaagtttta aatcaatcta agtatatat      9120 gagtaaactt ggtctgacag ttaccaatgc ttaatcagtg aggcacctat ctcagcgatc     9180
tgtctatttc gttcatccat agttgcctga ctccccgtcg tgtagataac tacgatacgg     9240
gagggcttac catctggccc cagtgctgca atgataccgc gagacccacg ctcaccggct     9300
ccagatttat cagcaataaa ccagccagcc ggaagggccg agcgcagaag tggtcctgca     9360
actttatccg cctccatcca gtctattaat tgttgccggg aagctagagt aagtagttcg     9420
ccagttaata gtttgcgcaa cgttgttgcc attgctacag gcatcgtggt gtcacgctcg     9480
```

-continued

```
tcgtttggta tggcttcatt cagctccggt tcccaacgat caaggcgagt tacatgatcc    9540
cccatgttgt gcaaaaaagc ggttagctcc ttcggtcctc cgatcgttgt cagaagtaag    9600
ttggccgcag tgttatcact catggttatg gcagcactgc ataattctct tactgtcatg    9660
ccatccgtaa gatgcttttc tgtgactggt gagtactcaa ccaagtcatt ctgagaatag    9720
tgtatgcggc gaccgagttg ctcttgcccg gcgtcaatac gggataatac cgcgccacat    9780
agcagaactt taaaagtgct catcattgga aaacgttctt cggggcgaaa actctcaagg    9840
atcttaccgc tgttgagatc cagttcgatg taacccactc gtgcacccaa ctgatcttca    9900
gcatctttta ctttcaccag cgtttctggg tgagcaaaaa caggaaggca aaatgccgca    9960
aaaaagggaa taagggcgac acggaaatgt tgaatactca tactcttcct ttttcaatat   10020
tattgaagca tttatcaggg ttattgtctc atgagcggat acatatttga atgtatttag   10080
aaaaataaac aaatagggt tccgcgcaca tttccccgaa aagtgccacc tgacgtctaa    10140
gaaaccatta ttatcatgac attaacctat aaaaataggc gtatcacgag gccctttcgt   10200
ctcgcgcgtt tcggtgatga cggtgaaaac ctctgacaca tgcagctccc ggagacggtc   10260
acagcttgtc tgtaagcgga tgccgggagc agacaagccc gtcagggcgc gtcagcgggt   10320
gttggcgggt gtcggggctg gcttaactat gcggcatcag agcagattgt actgagagtg   10380
caccatatgc ggtgtgaaat accgcacaga tgcgtaagga gaaaataccg catcaggcgc   10440
cattcgccat tcaggctgcg caactgttgg gaagggcgat cggtgcgggc ctcttcgcta   10500
ttacgccagc tggcgaaagg gggatgtgct gcaaggcgat taagttgggt aacgccaggg   10560
ttttcccagt cacgacgttg taaaacgacg gccagtgaat tcaagcttaa tacgactcac   10620
tata                                                                10624
```

<210> SEQ ID NO 3
<211> LENGTH: 891
<212> TYPE: DNA
<213> ORGANISM: Apium graveolens

<400> SEQUENCE: 3

```
atgacgcgat tatattctgt gttctttctt ttgttggctc ttgtagttga accgggtgtt     60
agagcctgga gcaaagaagg ccatgtcatg acatgtcaaa ttgcgcagga tctgttggag    120
ccagaagcag cacatgctgt aaagatgctg ttaccggact atgctaatgg caacttatcg    180
tcgctgtgtg tgtggcctga tcaaattcga cactggtaca agtacaggtg gactagctct    240
ctccatttca tcgatacacc tgatcaagcc tgttcatttg attaccagag agactgtcat    300
gatccacatg gagggaagga catgtgtgtt gctggagcca ttcaaaattt cacatctcag    360
cttggacatt tccgccatgg aacatctgat cgtcgatata atatgacaga ggctttgtta    420
tttttatccc acttcatggg agatattcat cagcctatgc atgttggatt tacaagtgat    480
atgggaggaa acagtataga tttgcgctgg tttcgccaca atccaacct gcaccatgtt    540 tgggatagag agattattct tacagctgca gcagattacc atggtaagga tatgcactct    600
ctcctacaag acatacagag gaactttaca gagggtagtt ggttgcaaga tgttgaatcc    660
tggaaggaat gtgatgatat ctctacttgc gccaataagt atgctaagga gagtataaaa    720
ctagcctgta actggggtta caagatgtt gaatctggcg aaactctgtc agataaatac     780
ttcaacacaa gaatgccaat tgtcatgaaa cggatagctc agggtggaat ccgtttatcc    840
atgattttga accgagttct tggaagctcc gcagatcatt ctttggcatg a             891
```

```
<210> SEQ ID NO 4
<211> LENGTH: 915
<212> TYPE: DNA
<213> ORGANISM: Apium graveolens

<400> SEQUENCE: 4
atgacgcgat tatattctgt gttctttctt ttgttggctc ttgtagttga accgggtgtt      60
agagcctgga gcaaagaagg ccatgtcatg acatgtcaaa ttgcgcagga tctgttggag     120
ccagaagcag cacatgctgt aaagatgctg ttaccggact atgctaatgg caacttatcg     180
tcgctgtgtg tgtggcctga tcaaattcga cactggtaca agtacaggtg gactagctct     240
ctccatttca tcgatacacc tgatcaagcc tgttcatttg attaccagag agactgtcat     300
gatccacatg gagggaagga catgtgtgtt gctggagcca ttcaaaattt cacatctcag     360
cttggacatt tccgccatgg aacatctgat cgtcgatata atatgacaga ggctttgtta     420
tttttatccc acttcatggg agatattcat cagcctatgc atgttggatt acaagtgat      480
atgggaggaa acagtataga tttgcgctgg tttcgccaca atccaaccct gcaccatgtt     540
tgggatagag agattattct tacagctgca gcagattacc atggtaagga tatgcactct     600
ctcctacaag acatacagag gaactttaca gagggtagtt ggttgcaaga tgttgaatcc     660
tggaaggaat gtgatgatat ctctacttgc gccaataagt atgctaagga gagtataaaa     720
ctagcctgta actggggtta caaagatgtt gaatctggcg aaactctgtc agataaatac     780
ttcaacacaa gaatgccaat tgtcatgaaa cggatagctc agggtggaat ccgtttatcc     840
atgatttttga accgagttct tggaagctcc gcagatcatt ctttggcagg aggtcaccat     900
caccatcacc attga                                                     915

<210> SEQ ID NO 5
<211> LENGTH: 717
<212> TYPE: DNA
<213> ORGANISM: Artificial
<220> FEATURE:
<223> OTHER INFORMATION: This construct was derived by GRAMMR shuffling
      in accordance with the methodology of the present invention.

<400> SEQUENCE: 5
atgagtaaag gagaagaact tttcactgga gttgtcccaa ttcttgttga attagatggt      60
gatgttaatg ggcacaaatt ttctgtcagt ggagagggtg aaggtgatgc aacatacgga     120
aaacttaccc ttaaatttat ttgcactact ggaaaactac ctgttccatg gccaacactt     180
gtcactactt tctcttatgg tgttcaatgc ttttcaagat acccagatca tatgaaacgg     240
catgactttt tcaagagtgc catgcccgaa ggttatgtac aggaacgcac tatattttc      300
aaggatgacg ggaactacaa gacacgtgct gaagtcaagt ttgaaggtga taccctttgtt    360
aatagaatcg agttaaaagg tattgatttt aagaagatgg aaacattctt ggacacaaa      420
ttggaataca actataactc acacaatgta tacatcatgg cagacaaaca aaagaatgga     480
atcaaagtta acttcaaaat tagacacaac attgaagatg gaagcgttca actagcagac     540
cattatcaac aaaatactcc aattggcgat ggccctgtcc ttttaccaga caaccattac     600
ctgtccacac aatctgccct ttcgaaagat cccaacgaaa agagagacca catggtcctt     660
cttgagtttg taacagctgc tgggattaca catggcatgg atgaactata caaataa        717

<210> SEQ ID NO 6
<211> LENGTH: 717
<212> TYPE: DNA
<213> ORGANISM: Artificial
```

```
<220> FEATURE:
<223> OTHER INFORMATION: This construct was derived by GRAMMR shuffling
      in accordance with the methodology of the present invention.

<400> SEQUENCE: 6
atgagtaaag gagaagaact tttcactgga gttgtcccaa ttcttgttga attagatggt      60
gatgttaatg ggcacaaatt ttctgtcagt ggagagggtg aaggtgatgc tacatacgga     120
aagcttaccc ttaaatttat ttgcactact ggaaaactac ctgttccatg gccaacactt    180
gtcactactt tctcttatgg tgttcaatgc ttttcaagat acccagatca tatgaaacgg    240
catgactttt tcaagagtgc catgcccgaa ggttatgtac aggaacgcac tatatctttc    300
aaagatgacg ggaactacaa gacacgtgct gaagtcaagt ttgaaggtga tacccttgtt    360
aatagaatcg agttaaaagg tattgatttt aaagaagatg aaacattct tggacacaaa     420 ctcgagtaca actataactc acacaatgta tacatcatgg cagacaaaca aaagaatgga    480
atcaaagtta acttcaaaat tagacacaac attgaagatg aagcgttca actagcagac     540 cattatcaac aaaatactcc aattggcgat ggccctgtcc ttttaccaga caaccattac    600
ctgtccacac aatctgccct ttcgaaagat cccaacgaaa agagagacca catggtcctt    660
cttgagtttg taacagctgc tgggattaca catggcatgg atgaactata caaataa       717

<210> SEQ ID NO 7
<211> LENGTH: 717
<212> TYPE: DNA
<213> ORGANISM: Artificial
<220> FEATURE:
<223> OTHER INFORMATION: This construct was derived by GRAMMR shuffling
      in accordance with the methodology of the present invention.

<400> SEQUENCE: 7
atgagtaaag gagaagaact tttcactgga gttgtcccaa ttcttgttga attagatggt      60
gatgttaatg ggcacaaatt ttctgtcagt ggagagggtg aaggtgatgc tacatacgga     120
aagcttaccc ttaaatttat ttgcactact ggaaaactac ctgttccatg gccaacactt    180
gtcactactt tctcttatgg tgttcaatgc ttttcccgtt atccggatca tatgaaacgg    240
catgactttt tcaagagtgc catgcccgaa ggttatgtac aggaacgcac tatatctttc    300
aaagatgacg ggaactacaa gacgcgtgct gaagtcaagt ttgaaggtga tacccttgtt    360
aatagaatcg agttaaaagg tattgatttt aaagaagatg aaacattct cggacacaaa     420 ttggaataca actataactc acacaatgta tacatcacgg cagacaaaca aaagaatgga    480
atcaaagcta acttcaaaat tcgccacaac attgaagatg gatccgttca actagcagac    540
cattatcaac aaaatactcc aattggcgat ggccctgtcc ttttaccaga caaccattac    600
ctgtcgacac aatctgccct ttcgaaagat cccaacgaaa agcgtgacca catggtcctt    660
cttgagtttg taactgctgc tgggattaca catggcatgg atgaactata caaataa       717

<210> SEQ ID NO 8
<211> LENGTH: 717
<212> TYPE: DNA
<213> ORGANISM: Artificial
<220> FEATURE:
<223> OTHER INFORMATION: This construct was derived by GRAMMR shuffling
      in accordance with the methodology of the present invention.

<400> SEQUENCE: 8
atgagtaaag gagaagaact tttcactgga gttgtcccaa ttcttgttga attagatggt      60
gatgttaatg ggcacaaatt ttctgtcagt ggagagggtg aaggtgatgc aacatacgga    120
```

```
aaacttaccc ttaaatttat ttgcactact ggaaaactac ctgttccatg gccaacactt    180
gtcactactt tctcttatgg tgttcaatgc ttttcaagat acccagatca tatgaaacgg    240
catgactttt tcaagagtgc catgcccgaa ggttatgtac aggaaagaac tatattttc    300 aaggatgacg ggaactacaa gacacgtgct gaagtcaagt ttgaaggtga tacccttgtt    360
aatagaatcg agttaaaagg tattgatttt aaagaagatg gaaacattct cggacacaaa    420
ctcgagtaca actataactc acacaatgta tacatcatgg cagacaaaca aaagaatgga    480
atcaaagtta acttcaaaat tcgccacaac attgaagatg gatccgttca actagcagac    540
cattatcaac aaaatactcc aattggcgat ggccctgtcc ttttaccaga caaccattac    600
ctgtccacac aatctgccct ttcgaaagat cccaacgaaa agagagacca catggtcctt    660
cttgagtttg taacagctgc tgggattaca catggcatgg atgaactata caaataa     717
```

<210> SEQ ID NO 9
<211> LENGTH: 807
<212> TYPE: DNA
<213> ORGANISM: Tobacco mosaic virus
<400> SEQUENCE: 9

```
atggctctag ttgttaaagg aaaagtgaat atcaatgagt ttatcgacct gacaaaaatg     60
gagaagatct taccgtcgat gtttacccct gtaaagagtg ttatgtgttc caagttgat    120 aaaataatgg ttcatgagaa tgagtcattg tcagggtga accttcttaa aggagttaag    180
cttattgata gtggatacgt ctgtttagcc ggtttggtcg tcacgggcga gtggaacttg    240
cctgacaatt gcagaggagg tgtgagcgtg tgtctggtgg acaaaaggat ggaaagagcc    300
gacgaggcca ctctcggatc ttactacaca gcagctgcaa gaaaagatt tcagttcaag    360 gtcgttccca attatgctat aaccacccag gacgcgatga aaaacgtctg gcaagtttta    420
gttaatatta gaaatgtgaa gatgtcagcg ggtttctgtc cgctttctct ggagtttgtg    480
tcggtgtgta ttgtttatag aaataatata aaattaggtt tgagagagaa gattacaaac    540
gtgagagacg gagggcccat ggaacttaca gaagaagtcg ttgatgagtt catggaagat    600
gtccctatgt cgatcaggct tgcaaagttt cgatctcgaa ccggaaaaaa gagtgatgtc    660
cgcaaaggga aaaatagtag tagtgatcgg tcagtgccga acaagaacta tagaaatgtt    720
aaggattttg gaggaatgag ttttaaaaag aataatttaa tcgatgatga ttcggaggct    780
actgtcgccg aatcggattc gttttaa                                       807
```

<210> SEQ ID NO 10
<211> LENGTH: 793
<212> TYPE: DNA
<213> ORGANISM: Tomato mosaic virus
<400> SEQUENCE: 10

```
atggctctag ttgttaaagg taaggtaaat attaatgagt ttatcgatct gtcaaagtct     60
gagaaacttc tcccgtcgat gttcacgcct gtaaagagtg ttatggtttc aaaggttgat    120
aagattatgg tccatgaaaa tgaatcattg tctgaagtaa atctcttaaa aggtgtaaaa    180
cttatagaag gtgggtatgt ttgcttagtt ggtcttgttg tgtccggtga gtggaattta    240
ccagataatt gccgtggtgg tgtgagtgtc tgcatggttg acaagagaat ggaaagagcg    300
gacgaagcca cactgggtc atattacact gctgctgcta aaagcggtt tcagtttaaa    360 gtggtcccaa attacggtat tactacaaag gatgcagaaa agaacatatg gcaggtctta    420
```

```
gtaaatatta aaaatgtaaa aatgagtgcg ggctactgcc ctttgtcatt agaatttgtg    480
tctgtgtgta ttgtttataa aaataatata aaattgggtt tgagggagaa agtaacgagt    540
gtgaacgatg gaggacccat ggaactttca gaagaagttg ttgatgagtt catggagaat    600
gttccaatgt cggttagact cgcaaagttt cgaaccaaat cctcaaaaag aggtccgaaa    660
aataataata atttaggtaa ggggcgttca ggcggaaggc ctaaaccaaa agttttgat     720 gaagttgaaa aagagtttga aatttgatt gaagatgaag ccgagacgtc ggtcgcggat     780
tctgattcgt att                                                      793

<210> SEQ ID NO 11
<211> LENGTH: 795
<212> TYPE: DNA
<213> ORGANISM: Artificial
<220> FEATURE:
<223> OTHER INFORMATION: This construct was derived by GRAMMR shuffling
      in accordance with the methodology of the present invention.

<400> SEQUENCE: 11
atggctctag ttgttaaagg taaggtaaat attaatgagt ctatcgatct gtcaaagtct     60
gagaaacttc tcccgtcgat gttcacgcct gtaaagagtg ttatggtttc aaaggttgat   120
aagattatgg tccatgaaaa tgaatcattg tctgaagtaa atctcttaaa aggtgtaaaa   180
cttatagaag gtgggtatgt ttgcttagtt ggtcttgttg tgtccggtga gtggaattta   240
ccagataatt gccgtggtgg tgtgagtgtc tgcatggttg acaagagaat ggaaagagcg   300
gacgaagcca cactggggtc atattacact gctgctgcta aaaagcggtt tcagttcaag   360
gtcgttccca attatgctat aaccacccag gatgcagaaa agaacatatg gcaggtctta   420
gtaaatatta aaaatgtaaa aatgagtgcg ggctactacc ctttgtcatt agaatttgtg   480
tctgtgtgta ttgtttataa aaataatata aaattgggtt tgagggagaa agtaacgagt   540
gtgaacgatg gaggacccat ggaactttca gaagaagttg ttgatgagtt catggagaat   600
gttccaatgt cgatcaggct tgcaaagttt cgaaccaaat cctcaaaaag aggtccgaaa   660
aataataata atttaggtaa ggggcgttca ggcggaaggc ctaaaccaag aagttttgat   720
gaagttgaaa aagagtttga aatttgatt gaagatgaag ccgagacgtc ggtcgcggat    780
tctgattcgt attaa                                                   795

<210> SEQ ID NO 12
<211> LENGTH: 795
<212> TYPE: DNA
<213> ORGANISM: Artificial
<220> FEATURE:
<223> OTHER INFORMATION: This construct was derived by GRAMMR shuffling
      in accordance with the methodology of the present invention.

<400> SEQUENCE: 12
atggctctag ttgttaaagg taaggtaaat attaatgagt ttatcgatct gtcaaagtct     60
gagaaacttc tcccgtcgat gttcacgcct gtaaagagtg ttatggtttc aaaggttgat   120
aagattatgg tccatgaaaa tgaatcattg tctgaagtaa atctcttaaa aggtgtaaaa   180
cttatagaag gtgggtatgt ttgcttagtt ggtcttgttg tgtccggtgt gtggaattta   240
ccagataatt gccgtggtgg tgtgagtgtc tgcatggttg acaagagaat ggaaagagcg   300
gacgaggcca cactcggatc ttactacact gctgctgcta aaaagcggtt tcagttcaag   360
gtcgttccca attatgctat aaccacccag gatgcagaaa agaacatatg gcaggtctta   420
gtaaatatta aaaatgtaaa aatgagtgcg ggctactgcc ctttgtcatt agaatttgtg   480
```

```
tctgtgtgta ttgtttataa aaataatata aaattgggtt tgagggagaa agtaacgagt    540
gtgaacgatg gaggacccat ggaactttca gaagaagttg ttgatgagtt catggagaat    600
gttccaatgt cggttagact cgcaaagttt cgaaccaaat cctcaaaaag aggtccgaaa    660
aataataata atttaggtaa ggggcgttca ggcggaaggc ctaaaccaaa agttttgat    720 gaagttggaa aagagtttga aatttgatt gaagatgaag ccgagacgtc ggtcgcggat    780
tctgattcgt attaa                                                     795

<210> SEQ ID NO 13
<211> LENGTH: 795
<212> TYPE: DNA
<213> ORGANISM: Artificial
<220> FEATURE:
<223> OTHER INFORMATION: This construct was derived by GRAMMR shuffling
      in accordance with the methodogy of the present invention.

<400> SEQUENCE: 13
atggctctag ttgttaaagg taaggtaaat attaatgagt ttatcgatct gtcaaagtct     60
gagaaacttc tcccgtcgat gttcacgcct gtaaggagtg ttatggtttc aaaggttgat    120
aagattatgg tccatgaaaa tgaatcattg tctgaagtaa atctcttaaa aggtgtaaaa    180
cttatagaag gtgggtatgt ttgcttagtt ggtcttgttg tgtccggtga gtggaattta    240
ccagataatt gccgtggtgg tgtgagtgtc tgcatggttg acaagagaat ggaaagagcg    300
gacgaagcca cactggggtc atattacact gctgctgcta aaaagcggtt tcagtttaaa    360
gtggtcccaa attacggtat tactacccag gacgcgatga aaaacgtctg gcaggtctta    420
gtaaatatta aaaatgtaaa aatgagtgcg ggctactgcc ctttgtcatt agaatttgtg    480
tctgtgtgta ttgtttataa aaataatata aaattgggtt tgagggagaa agtaacgagt    540
gtgaacgatg gaggacccat ggaactttca gaagaagttg ttgatgagtt catggagaat    600
gttccaatgt cgatcagact cgcaaagttt cgaaccaaat cctcaaaaag aggtccgaaa    660
aataataata atttaggtaa ggggcgttca ggcggaaggc ctaaaccaaa agttttgat    720 gaagttgaaa aagagtttga aatttgatt gaagatgaag ccgagacgtc ggtcgcggat    780
tctgattcgt attaa                                                     795

<210> SEQ ID NO 14
<211> LENGTH: 796
<212> TYPE: DNA
<213> ORGANISM: Artificial
<220> FEATURE:
<223> OTHER INFORMATION: This construct was derived by GRAMMR shuffling
      in accordance with the methodogy of the present invention.

<400> SEQUENCE: 14
atggctctag ttgttaaagg taaggtaaat attaatgagt ttatcgatct gtcaaagtct     60
gagaaacttc tcccgtcgat gttcacgcct gtaaagagtg ttatggtttc aaaggttgat    120
aagattatgg tccatgaaaa tgaatcattg tctgaagtaa atctcttaaa aggtgttaag    180
cttattgata gtggatacgt ctgtttagcc ggtttggtcg tcacgggcga gtggaattta    240
ccagataatt gccgtggtgg tgtgagtgtc tgcatggttg acaagagaat ggaaagagcg    300
gacgaagcca cactggggtc atattacact gctgctgcta aaaagcggtt tcagttcaag    360
gtcgttccca attacggta ttactaccca ggatgcagaa aagaacatat ggcaggtctt    420
agtaaatatt aaaaatgtaa aatgagtgc gggctactgc ccgctttctc tggagtttgt    480
```

```
gtctgtgtgt attgtttata aaaataatat aaaattgggt ttgagggaga agtaacgag      540 tgtgaacgat ggaggaccca tggaactttc agaagaagtt gttgatgagt tcatggagaa    600
tgttccaatg tcggttagac tcgcaaagtt tcgaaccaaa tcctcaaaaa gaggtccgaa    660
aaataataat aatttaggta aggggcgttc aggcggaagg cctaaaccaa aaagttttga    720
tgaagttgaa aaagagtttg ataatttgat tgaggatgat tcggaggcta ctgtcgccga    780
ttctgattcg tattaa                                                    796

<210> SEQ ID NO 15
<211> LENGTH: 795
<212> TYPE: DNA
<213> ORGANISM: Artificial
<220> FEATURE:
<223> OTHER INFORMATION: This construct was derived by GRAMMR shuffling
      in accordance with the methodology of the present invention.

<400> SEQUENCE: 15
atggctctag ttgttaaagg aaaagtgaat attaatgagt ttatcgatct gtcaaagtct     60
gagaaacttc tcccgtcgat gttcacgcct gtaaagagtg ttatggtttc aaaggttgat    120
aagattatgg tccatgaaaa tgaatcattg tctgaagtaa atctcttaaa aggtgtaaaa    180
cttatagaag gtgggtatgt ttgcttagtt ggtcttgttg tgtccggcga gtggaattta    240
ccagataatt gccgtggtgg tgtgagtgtc tgcatggtta caagagaat ggaaagagcg     300 gacgaagcca cactggggtc atattacact gctgctgcaa agaaaagatt tcagttcaag    360
gtcgttccca attatgctat aaccacccag gatgcagaaa agaacatatg gcgggtctta    420
gtaaatatta aaaatgtaaa aatgagtgcg ggctactgcc cgctttctct ggagtttgtg    480
tctgtgtgta ttgtttataa aaataatata aaattgggtt tgagggagaa agtaacgagt    540
gtgaacgatg aaggacccat ggaactttca gaagaagttg ttgatgagtt catggagaat    600
gttccaatgt cgatcaggct cgcaaagttt cgaaccaaat cctcaaaaag aggtccgaaa    660
aataataata atttaggtaa ggggcgttca ggcggaaggc taaaccaaa aagttttgat     720 gaagttgaaa aagagtttga atttgattg gaagatgaag ccgagacgtc ggtcgcggat    780
tctgattcgt actaa                                                    795

<210> SEQ ID NO 16
<211> LENGTH: 888
<212> TYPE: DNA
<213> ORGANISM: Selaginella lepidophylla

<400> SEQUENCE: 16
atggcaacga ccaagacgag cgggatggcg ctggctttgc tcctcgtcgc cgccctggcc     60
gtgggagctg cggcctgggg gaaagagggc catcgcctca cttgtatggt cgccgagccc    120
tttctaagct ctgaatccaa gcaagctgtg gaggagcttc tctctggaag agatctcccg    180
gacttgtgtt catgggccga tcagattcga agatcgtata agtttagatg gactggtcct    240
ttgcactaca tcgatactcc agacaacctc tgcacctatg actatgatcg tgactgccac    300
gattcccatg ggaagaagga cgtgtgtgtc gctggtggga tcaacaatta ctcgtcgcag    360
ctggaaacgt ttctagattc agagagctcg tcgtataact tgaccgaggc gctgctcttc    420
ctggctcact ttgtcgggga tatacaccag cccttgcacg tagcatttac gagtgatgcc    480
ggaggcaatg gcgtgcacgt ccgctggttt ggacgaaagg ccaacttgca tcacgtctgg    540
gatacagaat ttatttctag agccaatcgt gtgtactacc acgacatttc caagatgctc    600
```

```
cggaacatta ccaggagcat aactaagaag aatttcaata gttggagcag atgtaagact    660
gatccggcgg cttgtattga tagttatgcg acagaaagta tagatgcttc ttgcaactgg    720
gcatacaaag acgcacccga cggaagctct ctagatgatg attacttctc ttcacgcctt    780
ccaattgttg agcagcgtct tgctcaaggg ggcgtcaggc tggcgtcaat actcaacagg    840 attttggag gagcaaagtc gaacaggtcc agtcgctcaa gcatgtag              888
```

<210> SEQ ID NO 17
<211> LENGTH: 3637
<212> TYPE: DNA
<213> ORGANISM: Artificial
<220> FEATURE:
<223> OTHER INFORMATION: Encodes cycle 3 GFP

<400> SEQUENCE: 17

```
gtggcacttt tcggggaaat gtgcgcggaa cccctatttg tttatttttc taaatacatt     60
caaatatgta tccgctcatg agacaataac cctgataaat gcttcaataa tattgaaaaa    120
ggaagagtat gagtattcaa catttccgtg tcgcccttat cccttttttt gcggcatttt    180
gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcacttttaa agttctgcta tgtggcgcgg    360
tattatcccg tattgacgcc gggcaagagc aactcggtcg ccgcatacac tattctcaga    420
atgacttggt tgagtactca ccagtcacag aaaagcatct tacgatggc atgacagtaa     480 gagaattatg cagtgctgcc ataaccatga gtgataacac tgcggccaac ttacttctga    540
caacgatcgg aggaccgaag gagctaaccg cttttttgca acatggggg gatcatgtaa     600 ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag cgcagcggt cgggctgaac ggggggttcg tgcacacagc    1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
```

-continued

```
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct gggtaccgat gagtaaagga   2220
gaagaacttt tcactggagt tgtcccaatt cttgttgaat tagatggtga tgttaatggg   2280
cacaaatttt ctgtcagtgg agagggtgaa ggtgatgcta catacggaaa gcttaccctt   2340
aaatttattt gcactactgg aaaactacct gttccatggc caacacttgt cactactttc   2400
tcttatggtg ttcaatgctt ttcccgttat ccggatcata tgaaacggca tgactttttc   2460
aagagtgcca tgcccgaagg ttatgtacag gaacgcacta tatctttcaa agatgacggg   2520
aactacaaga cgcgtgctga agtcaagttt gaaggtgata cccttgttaa tcgtatcgag   2580
ttaaaaggta ttgattttaa agaagatgga aacattctcg gacacaaact cgagtacaac   2640
tataactcac acaatgtata catcacggca gacaaacaaa agaatggaat caaagctaac   2700
ttcaaaattc gccacaacat tgaagatgga tccgttcaac tagcagacca ttatcaacaa   2760
aatactccaa ttggcgatgg ccctgtcctt ttaccagaca accattacct gtcgacacaa   2820
tctgcccttt cgaaagatcc caacgaaaag cgtgaccaca tggtccttct tgagtttgta   2880
actgctgctg ggattacaca tggcatggat gaactataca aataagaatt cctgcagccc   2940
gggggatcca ctagttctag agcggccgcc accgcggtgg agctccaatt cgccctatag   3000
tgagtcgtat tacgcgcgct cactggccgt cgttttacaa cgtcgtgact gggaaaaccc   3060
tggcgttacc caacttaatc gccttgcagc acatccccct ttcgccagct ggcgtaatag   3120
cgaagaggcc cgcaccgatc gcccttccca acagttgcgc agcctgaatg gcgaatggga   3180
cgcgccctgt agcggcgcat taagcgcggc gggtgtggtg gttacgcgca gcgtgaccgc   3240
tacacttgcc agcgccctag cgcccgctcc tttcgctttc ttcccttcct ttctcgccac   3300
gttcgccggc tttccccgtc aagctctaaa tcgggggctc cctttagggt tccgatttag   3360
tgctttacgg cacctcgacc ccaaaaaact tgattagggt gatggttcac gtagtgggcc   3420
atcgccctga tagacggttt ttcgcccttt gacgttggag tccacgttct ttaatagtgg   3480
actcttgttc caaactggaa caacactcaa ccctatctcg gtctattctt ttgatttata   3540
agggattttg ccgatttcgg cctattggtt aaaaaatgag ctgatttaac aaaaatttaa   3600
cgcgaatttt aacaaaatat taacgcttac aatttag                            3637
```

<210> SEQ ID NO 18
<211> LENGTH: 796
<212> TYPE: DNA
<213> ORGANISM: Tobamovirus Cg

<400> SEQUENCE: 18

```
atgtcttacg agcctaaagt gagcgacttc cttgctctta cgaaaaagga ggaaatttta     60
cccaaggctc ttacgaggtt aaagactgtc tctattagta ctaaggatgt tatatctgtt    120
aaggattctg agtccctgtg tgatatagat ttactagtta atgtgccatt agataagtat    180
agatatgtgg gtgttttagg tgttgttttt accggtgagt ggttagtgcc ggatttcgtt    240
```

```
aaaggtggag taacagtgag cgtgattgac aaacggcttg agaactccaa agagtgcata    300
attggtacgt acagagctgc tgcgaaagac aaaaggttcc agttcaagct ggttccaaat    360
tacttcgtgt ctgttgcaga tgccaagcga aaaccgtggc aagttcatgt gcgtattcaa    420
aatttaagga ttgaagctgg atggcaacct ctggccttag aggtggtttc tgttgctatg    480
gtcactaata acgtggttgt taagggtttg agagaaaagg tcatcgcagt gaatgatccg    540
aatgtcgaag gtttcgaagg cgtggttgac gatttcgtcg attcggtcgc agcattcaag    600
gcggttgaca ctttcagaaa gaaaagaaa aggattggag aaaggatgt aaataataat    660 aagtttagat atagaccgga gagatacgcc ggtcaggatt cgttaaatta taagaagaa    720 aacgtcttac aacatcacga actcgaatca gtaccagtat ttcgcagcga cgtgggcaga    780
gcccacagcg atgctt                                                    796
```

<210> SEQ ID NO 19
<211> LENGTH: 823
<212> TYPE: DNA
<213> ORGANISM: Tobamovirus Ob

<400> SEQUENCE: 19

```
atgtcaaagg ctattgtcaa gatcgatgaa ttcattaaat tatccaagtc tgaagaggtt     60
ttaccttctg cattcacaag aatgaagtcg gtcagagtct caacagtgga taagataatg    120
gccaaagaga atgacaatat ttccgaagta gatttactta agggtgttaa gttagttaaa    180
aatggttatg tttgtttagt aggtcttgtg gtgtcaggag agtggaattt acccgacaac    240
tgcagaggtg gtgtaagtat ctgtctgata gacaaacgta tgcaacgtca taacgaagct    300
actttaggtt cgtacactac caaagccagc aagaaaaact tttcgttcaa gcttataccg    360
aattactcga taacctctca agatgctgaa aggcgtcctt gggaagttat ggtaaatatt    420
cgtggtgtgg ctatgtccga aggttggtgt ccattatcct tagagttcgt ttctgtttgt    480
attgttcata aaaacaatgt tagaaagggt ctaagagaga aggtgactgc cgtgtccgaa    540
gacgacgcta tagaactcac agaagaggtt gttgatgagt ttatagaagc cgtaccgatg    600
gcgcgacgtt tgcagaactt gagaaaaccc aagtacaaca agaaaaaga aaataaaaat    660 ttgaataata aaaatagtat aggagtttcc aaacctgtcg gtttggaaag aaataaagta    720
aggagtgtag ttagaaaagg ggttaggagt gatagtagtt taggtgtgac tgatatgagt    780
caggacggta gctcaagcga gatatcatcc gattcgttta ttt                      823
```

<210> SEQ ID NO 20
<211> LENGTH: 769
<212> TYPE: DNA
<213> ORGANISM: Tobacco mosaic virus U2

<400> SEQUENCE: 20

```
atggctgtta gtctcagaga tactgtcaaa attagcgagt tcattgatct ttcgaaacag     60
gatgagatac ttccggcatt catgactaag gtcaagagcg tcagaatatc gactgtggac    120
aagattatgg ctgttaagaa tgatagtctt tctgatgtag atttacttaa aggtgttaag    180
ttagttaaga atgggtacgt gtgcttagct ggtttggtag tgtctgggga gtggaatctc    240
ccggacaact gccgtggtgg tgtcagtgtt tgtattgtag ataagagaat gaaaaggagt    300
aaggaggcaa cgctgggtgc gtatcacgcc cctgcttgca aaagaatttt ttcctttaag    360
ctaatcccta attattcaat aacatccgag gatgctgaga agcacccatg gcaagtatta    420
gtgaatatca aaggagtggc tatggaagaa ggatactgtc ctttatcttt ggagttcgtt    480
```

```
tcaatttgtg tagtacataa aaataatgta agaaaaggtt tgagggaacg tattttgaga      540
gtaacagacg gctcgccaat tgaactcact gaaaaagttg ttgaggagtt catagatgaa      600
gtaccaatgg ctgtgaaact cgaaaggttc cggaaaacaa aaagagagt ggtaggtaat       660 agtgttaata ataagaaaat aaataatagt ggtaagaaag gtttgaaagt tgaggaaatt     720
gaggataatg taagtgatga cgagtctatc gcgtcatcga gtacgtttt                  769
```

<210> SEQ ID NO 21
<211> LENGTH: 808
<212> TYPE: DNA
<213> ORGANISM: Artificial
<220> FEATURE:
<223> OTHER INFORMATION: This construct was derived by GRAMMR shuffling
      in accordance with the methodolgy of the present invention.

<400> SEQUENCE: 21

```
atggctctag ttgttaaagg taaggtaaat attaatgagt ttatcgatct gtcaaagtct      60
gagaaacttc tcccgtcgat gttcacgcct gtaaagagtg ttatggtttc aaaggttgat    120
aagattatgg tccatgaaaa tgaatcattg tctgaagtaa atctcttaaa aggtgtaaaa    180
cttatagaag gtgggtatgt ttgcttagtt ggtcttgttg tgtccggtga gtggaattta    240
ccagataatt gccgtggtgg tgtgagtgtc tgcatggttg acaagagaat ggaaagagcg    300
gacgaagcca cactggggtc atattacact gctgctgcta aaaagcggtt tcagtttaaa    360
gtggtcccaa attacggtat tactacaaag gatgcagaaa agaacatatg gcaagttcat    420
gtgcgtattc aaaatttaag gattgaagct ggatggcaac ctctggcctt agaggtggtt    480
tctgttgcta tggtcactaa taacgtggtt gttaagggtt tgagagaaaa ggtcatcgca    540
gtgaatgatc cgaatgtcga aggtttcgaa ggcgtggttg acgatttcgt cgattcggtc    600
gcagcattca aggcggttga cactttcaga aagaaaaaga aaaggattgg aggaaaggat    660
gtaaataata ataagtttag atatagaccg gagagatacg ccggtcagga ttcgttaaat    720
tataaagaag aaaacgtctt acaacatcac gaactcgaat cagtaccagt atttcgcagc    780
gacgtgggca gagcccacag cgatgctt                                       808
```

<210> SEQ ID NO 22
<211> LENGTH: 799
<212> TYPE: DNA
<213> ORGANISM: Artificial
<220> FEATURE:
<223> OTHER INFORMATION: This construct was derived by GRAMMR shuffling
      in accordance with the methodolgy of the present invention.

<400> SEQUENCE: 22

```
atgtcttacg agcctaaagt gagcgacttc cttgctctta cgaaaaagga ggaaatttta    60
cccaaggctc ttacgaggtt aaagactgtc tctattagta ctaaggatgt tatatctgtt   120
aaggattctg agtccctgtg tgatatagat ttactagtta atgtgccatt agataagtat   180
agatatgtgg gtgttttagg tgttgttttt accggtgagt ggaatttacc agataattgc   240
cgtggtggtg tgagtgtctg catggttgac aagagaatgg aaagagcgga cgaagccaca   300
ctggggtcat attacactgc tgctgcgaaa gacaaaaggt tccagttcaa gctggttcca   360
aattacttcg tgtctgttgc agatgccaag cgaaaaccgg gcaagttca tgtgcgtatt    420 caaaatttaa ggattgaagc tggatggcaa cctctggcct tagaggtggt ttctgttgct    480
atggtcacta ataacgtggt tgttaagggt ttgagagaaa aggtcatcgc agtgaatgat   540
```

```
ccgaatgtcg aaggtttcga aggcgtggtt gacgatttcg tcgattcggt cgcagcattc    600
aaggcggttg acactttcag aaagaaaaag aaaggattg gaggaaagga tgtaaataat     660
aataagttta gatatagacc ggagagatac gccggtcagg attcgttaaa ttataaagaa    720
gaaaacgtct tacaacatca cgaactcgaa tcagtaccag tatttcgcag cgacgtgggc    780
agagcccaca gcgatgctt                                                 799
```

```
<210> SEQ ID NO 23
<211> LENGTH: 823
<212> TYPE: DNA
<213> ORGANISM: Artificial
<220> FEATURE:
<223> OTHER INFORMATION: This construct was derived by GRAMMR shuffling
      in accordance with the methodology of the present invention.

<400> SEQUENCE: 23
aaataaacga atcggatgat atctcgcttg agctaccgtc ctgactcata tcagtcacac     60
ctaaactact atcactccta acccctttc taactacact ccttacttta tttctttcca    120
aaccgacagg tttggaaact cctatactat ttttattatt caaattttta ttttcttttt   180
ctttgttgta cttgggtttt ctcaagttct gcaaacgtcg cgccatcggt acggcttcta   240
taaactcatc aacaacctct tctgtgagtt ctatagcgtc gtcttcggac acggcagtca   300
ccttctctct tagacccttt ctaacattgt ttttatgaac aatacaaaca gaaacgaact   360
ctaaggataa tggacaccaa ccttcggaca tagccacacc acgaatattt accataactt   420
cccaaggacg cctttcagca tcttgagagg ttatcgagta attcggtata agcttgaacg   480
aaaagttttt cttgctggct ttggtagtgt acgaacctaa agtagcttcg ttatgacgtt   540
gcatacgttt gtctatcaga cagatactta caccacctct gcagttgtcg ggtaaattcc   600
actctcctga caccacaaga cctactaaac aaacataacc accttctata agttttacac   660
cttttaagag atttacttca gacaatgatt cattctcttt ggccattatc ttatccactg   720
ttgagactct gaccgacttc attcttgtga atgcagaagg taaaacctct tcagacttgg   780
ataatttaat gaattcatcg atcttgacaa tagcctttga cat                     823
```

```
<210> SEQ ID NO 24
<211> LENGTH: 792
<212> TYPE: DNA
<213> ORGANISM: Artificial
<220> FEATURE:
<223> OTHER INFORMATION: This construct was derived by GRAMMR shuffling
      in accordance with the methodology of the present invention.

<400> SEQUENCE: 24
aatacgaatc agaatccgcg accgacgtct cggcttcatc ttcaatcaaa ttatcaaact     60 cttttcaac ttcatcaaaa cttttggtt taggccttcc gcctgaacgc cccttaccta    120
aattattatt attttcgga cctcttttg aggatttggt tcgaaacttt gcgagtctaa    180
ccgacattgg aacattctcc atgaactcat caacaacctc ttctgtgagt tctatagcgt   240
cgtcttcgga cacggcagtc accttctctc ttagacccct tctaacattg ttttatgaa   300 caatacaaac agaaacgaac tctaatgaca aagggcagta gcccgcactc attttacat    360 ttttaatatt tactaagacc tgccatatgt tctttctgc atcctttgta gtaataccgt    420
aatttgggac cactttaaac tgaaaccgct tttagcagc agcagtgtaa tatgacccca   480
gtgtggcttc gtccgctctt tccattctct tgtcaaccat gcagacactc acaccaccac   540
ggcaattatc tggtaaattc cactctcctg acaccacaag acctactaaa caaacataac   600
```

```
catttttaac taacttaaca cccttaagag atttacttcg gacaatgatt cattttcatg      660
gaccataatc ttatcaacct ttgaaaccat aacactcttt acaggcgtga atgcagaagg      720
taaaacctct tcagactttg acagatcgat aaactcatta atatttacct tacctttaac      780
aactagagcc at                                                         792

<210> SEQ ID NO 25
<211> LENGTH: 769
<212> TYPE: DNA
<213> ORGANISM: Artificial
<220> FEATURE:
<223> OTHER INFORMATION: This construct was derived by GRAMMR shuffling
      in accordance with the methodology of the present invention.

<400> SEQUENCE: 25
aatacgaatc agaatccgcg atagactcgt catcacttac attatcctca atttcctcaa       60
ctttcaaacc tttcttacca ctattattta ttttcttatt attaacacta ttacctacca      120
ctctcttttt tgttttccgg aacctttcga gtttcacagc cattggtact tcatctatga      180
actcatcaac aacttcttct gaaagttcca tgggtcctcc atcgttcaca ctcgttactt      240
tctccctcaa acccaatttt atattatttt tataaacaat acacacagac acaaattcta      300
aagataaagg gcagtatcct tcttccatag ccactccttt gatattcact aatacttgcc      360
atgggtgctt ttctgcatcc tcggatgtta ttgaataatt agggaccact ttaaactgaa      420
accgcttttt agcagcaggg gcgtgatacg cacccagcgt tgcctcctta ctcctttcca      480
ttctcttgtc aaccatgcag acactcacac caccacggca gttgtccggg agattccact      540
caccggacac aacaagacca actaagcaaa catacccacc ttctataagt tttacacctt      600
ttaagagatt tacttcagac aatgattcat tttcatggac cataatctta tcaacctttg      660
aaaccataac actctttaca ggcgtgaaca tcgacgggag aagtttctca gactttgaca      720
gatcgataaa ctcattaata tttaccttac ctttaacaac tagagccat                 769

<210> SEQ ID NO 26
<211> LENGTH: 772
<212> TYPE: DNA
<213> ORGANISM: Artificial
<220> FEATURE:
<223> OTHER INFORMATION: This construct was derived by GRAMMR shuffling
      in accordance with the methodology of the present invention.

<400> SEQUENCE: 26
aatacgaatc agaatccgcg accgacgtct cggcttcact tacattatcc tcaatttcct       60
caactttcaa actttcttac cactattatt tattttcttc attattaaca ctattaccta      120
ccactctctt ttttgttttc cggaaccttt cgagtttcac agccattggt acttcatcta      180
tgaactcatc aacaactttt tcagtgagtt caattggcga gccgtctgtt actctcaaaa      240
tacgttccct caaacccaat tttatattat ttttataaac aatacacaca gacacaaatt      300
ctaatgacaa agggcagtag cccgcactca ttttttacatt tttaatattt actaagacct      360
gccatgggtg cttctcagca tcctcggatg ttattgaata attagggatt agcttaaagg      420
aaaaattctt tttgcaagca ggggcgtgat acgcacccag tgtggcttcg tccgctcttt      480
ccattctctt gtcaaccatg cagacactca caccaccacg gcagttgtcc gggagattcc      540
actcaccgga cacaacaaga ccaactaagc acacgtaccc attcttaact aacttaacac      600
ctttaagtaa atctacatca gacaatgatt cattttcatg gaccataatc ttatcaacct      660
```

```
ttgaaaccat aacactcttt acaggcgtga acatcgacgg gagaagtttc tcagactttg    720
acagatcgat aaactcgcta attttgacag tatctctgag actaacagcc at            772
```

<210> SEQ ID NO 27
<211> LENGTH: 805
<212> TYPE: DNA
<213> ORGANISM: Artificial
<220> FEATURE:
<223> OTHER INFORMATION: This construct was derived by GRAMMR shuffling
      in accordance with the methody of the present invention.

<400> SEQUENCE: 27

```
atggctctag ttgttaaagg aaaagtgaat attaatgagt ttatcgatct gtcaaagtct    60
gagaaacttc tcccgtcgat gttcacgcct gtaaagagtg ttatggtttc aaaggttgat   120
aagattatgg tccatgaaaa tgaatcattg tctgaagtaa atctcttaaa aggtgtaaaa   180
cttatagaag gtgggtatgt ttgcttagtt ggtcttgttg tgtccggtga gtggaattta   240
ccagataatt gccgtggtgg tgtgagtgtc tgcatggttg acaagagaat ggaaagagcg   300
gacgaagcca ctctcggatc ttactacaca gcagctgcaa agaaaagatt tcagttcaag   360
gtcgttccca attatgctat aaccacccag gacgcgatga aaaacgtctg gcaagtttta   420
gttaatatta gaaatgtgaa gatgtcagcg ggtttctgtc cgctttctct ggagtttgtg   480
tctgtgtgta ttgtttataa aaataatata aaattgggtt tgaggagaa agtaacgagt    540 gtgaacgatg gaggacccat ggaactttca gaagaagttg ttgatgagtt catggaagat   600
gtcccaatgt cggttagact cgcaaagttt cgatctcgaa ccggaaaaaa gagtgatgtc   660
cgcaaaggga aaaatagtag tagtgatcgg tcagtgccga acaagaacta tagaaatgtt   720
aaggattttg gaggaatgag ttttaaaaag aataatttaa tcgatgatga ttcggagacg   780
tcggtcgcgg attctgattc gtatt                                        805
```

<210> SEQ ID NO 28
<211> LENGTH: 804
<212> TYPE: DNA
<213> ORGANISM: Artificial
<220> FEATURE:
<223> OTHER INFORMATION: This construct was derived by GRAMMR shuffling
      in accordance with the methody of the present invention.

<400> SEQUENCE: 28

```
atggctctag ttgttaaagg aaaagtgaat atcaatgagt ttatcgacct gacaaagtct    60
gagaaacttc tcccgtcgat gtttacccct gtaaagagtg ttatggttcc aaagttgata   120
agattatggt tcatgagaat gagtcattgt caggggtgaa ccttcttaaa ggagttaagc   180
ttattgatag tggatacgtc tgtttagccg gtttggtcgt cacgggcgag tggaacttgc   240
ctgacaattg ccgtggtggt gtgagcgtgt gtctggtgga caagagaatg aaagagcgg    300 acgaagccac actggggtca tattcactg ctgctgctaa aaagcggttt cagttcaagg    360
tcgttcccaa ttatgctata accacccagg atgcagaaaa gaacatatgg caggtcttag   420
taaatattaa aaatgtgaag atgagtgcgg gctactgccc tttgtcatta gaatttgtgt   480
cggtgtgtat tgtttataga aataatataa aattgggttt gagagagaaa gtaacgagtg   540
tgaacgatgg agggcccatg gaacttacag aagaagtcgt tgatgagttc atggaagatg   600
tccctatgtc gatcaggctt gcaaagtttc gatctcgaat cctcaaaaag agtgatgtcc   660
gcaaagggaa aaatagtagt agtgatcggt cagtgccgaa caagaactat agaaatgtta   720
aggattttgg aggaatgagt tttaaaaaga ataatttaat cgatgatgat tcggaggcta   780
```

```
ctgtcgcgga ttctgattcg tttt                                         804

<210> SEQ ID NO 29
<211> LENGTH: 717
<212> TYPE: DNA
<213> ORGANISM: Aequorea victoria GFP ORF

<400> SEQUENCE: 29
atgagtaaag gagaagaact tttcactgga gttgtcccaa ttcttgttga attagatggt    60
gatgttaatg gcacaaaatt tctgtcagt ggagagggtg aaggtgatgc aacatacgga   120
aaacttaccc ttaaatttat ttgcactact ggaaaactac ctgttccatg gccaacactt   180
gtcactactt tctcttatgg tgttcaatgc ttttcaagat acccagatca tatgaaacgg   240
catgactttt tcaagagtgc catgcccgaa ggttatgtac aggaaagaac tatatttttc   300
aaggatgacg ggaactacaa gacacgtgct gaagtcaagt ttgaaggtga tacccttgtt   360
aatagaatcg agttaaaagg tattgatttt aaagaagatg gaaacattct tggacacaaa   420
ttggaataca actataactc acacaatgta tacatcatgg cagacaaaca aaagaatgga   480
atcaaagtta acttcaaaat tagacacaac attgaagatg gaagcgttca actagcagac   540
cattatcaac aaaatactcc aattggcgat ggccctgtcc ttttaccaga caaccattac   600
ctgtccacac aatctgccct ttcgaaagat cccaacgaaa agagagacca catggtcctt   660
cttgagtttg taacagctgc tgggattaca catggcatgg atgaactata caaataa     717

<210> SEQ ID NO 30
<211> LENGTH: 717
<212> TYPE: DNA
<213> ORGANISM: Aequorea victoria GFP cycle3 ORF

<400> SEQUENCE: 30
atgagtaaag gagaagaact tttcactgga gttgtcccaa ttcttgttga attagatggt    60
gatgttaatg gcacaaaatt tctgtcagt ggagagggtg aaggtgatgc tacatacgga   120
aagcttaccc ttaaatttat ttgcactact ggaaaactac ctgttccatg gccaacactt   180
gtcactactt tctcttatgc tgttcaatgc ttttcccgtt atccggatca tatgaaacgg   240
catgactttt tcaagagtgc catgcccgaa ggttatgtac aggaacgcac tatatctttc   300
aaagatgacg ggaactacaa gacgcgtgct gaagtcaagt ttgaaggtga tacccttgtt   360
aatcgtatcg agttaaaagg tattgatttt aaagaagatg gaaacattct cggacacaaa   420
ctcgagtaca actataactc acacaatgta tacatcacgg cagacaaaca aaagaatgga   480
atcaaagcta acttcaaaat tcgccacaac attgaagatg gatccgttca actagcagac   540
cattatcaac aaaatactcc aattggcgat ggccctgtcc ttttaccaga caaccattac   600
ctgtcgacac aatctgccct ttcgaaagat cccaacgaaa agcgtgacca catggtcctt   660
cttgagtttg taactgctgc tgggattaca catggcatgg atgaactata caaataa     717

<210> SEQ ID NO 31
<211> LENGTH: 3637
<212> TYPE: DNA
<213> ORGANISM: Artificial
<220> FEATURE:
<223> OTHER INFORMATION: Plasmid encoding wild type Aequorea victoria
      GFP Cycle 3 ORF

<400> SEQUENCE: 31
gtggcacttt tcggggaaat gtgcgcggaa cccctatttg tttatttttc taaatacatt    60
```

```
caaatatgta tccgctcatg agacaataac cctgataaat gcttcaataa tattgaaaaa    120
ggaagagtat gagtattcaa catttccgtg tcgcccttat tccctttttt gcggcatttt    180
gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcacttttaa agttctgcta tgtggcgcgg    360
tattatcccg tattgacgcc gggcaagagc aactcggtcg ccgcatacac tattctcaga    420
atgacttggt tgagtactca ccagtcacag aaaagcatct tacgatggc atgacagtaa     480 gagaattatg cagtgctgcc ataaccatga gtgataacac tgcggccaac ttacttctga    540
caacgatcgg aggaccgaag gagctaaccg cttttttgca caacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg ctggctggt ttattgctga taaatctgga gccggtgagc     840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag cgcagcggt cgggctgaac ggggggttcg tgcacacagc    1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct gggtaccgat gagtaaagga   2220
gaagaacttt tcactggagt tgtcccaatt cttgttgaat tagatggtga tgttaatggg   2280
cacaaatttt ctgtcagtgg agagggtgaa ggtgatgcaa catacggaaa acttaccctt   2340
aaatttattt gcactactgg aaaactacct gttccatggc caacacttgt cactactttc   2400
```

```
tcttatggtg ttcaatgctt ttcaagatac ccagatcata tgaaacggca tgactttttc    2460
aagagtgcca tgcccgaagg ttatgtacag gaaagaacta tattttttcaa ggatgacggg    2520 aactacaaga cacgtgctga agtcaagttt gaaggtgata cccttgttaa tagaatcgag    2580
ttaaaaggta ttgattttaa agaagatgga acacttcttg gacacaaatt ggaatacaac    2640
tataactcac acaatgtata catcatggca gacaaacaaa agaatggaat caaagttaac    2700
ttcaaaatta gacacaacat tgaagatgga agcgttcaac tagcagacca ttatcaacaa    2760
aatactccaa ttggcgatgg ccctgtcctt ttaccagaca accattacct gtccacacaa    2820
tctgcccttt cgaaagatcc caacgaaaag agagaccaca tggtccttct tgagtttgta    2880
acagctgctg ggattacaca tggcatggat gaactataca ataagaatt cctgcagccc    2940 gggggatcca ctagttctag agcggccgcc accgcggtgg agctccaatt cgccctatag    3000
tgagtcgtat tacgcgcgct cactggccgt cgttttacaa cgtcgtgact gggaaaaccc    3060
tggcgttacc caacttaatc gccttgcagc acatccccct ttcgccagct ggcgtaatag    3120
cgaagaggcc cgcaccgatc gcccttccca acagttgcgc agcctgaatg gcgaatggga    3180
cgcgccctgt agcggcgcat taagcgcggc gggtgtggtg gttacgcgca gcgtgaccgc    3240
tacacttgcc agcgccctag cgcccgctcc tttcgctttc ttcccttcct ttctcgccac    3300
gttcgccggc tttccccgtc aagctctaaa tcggggctc cctttagggt tccgatttag    3360
tgctttacgg cacctcgacc ccaaaaaact tgattagggt gatggttcac gtagtgggcc    3420
atcgccctga tagacggttt ttcgcccttt gacgttggag tccacgttct ttaatagtgg    3480
actcttgttc caaactggaa caacactcaa ccctatctcg gtctattctt ttgatttata    3540
agggattttg ccgatttcgg cctattggtt aaaaaatgag ctgatttaac aaaaatttaa    3600
cgcgaatttt aacaaaatat taacgcttac aatttag                            3637
```

<210> SEQ ID NO 32
<211> LENGTH: 3637
<212> TYPE: DNA
<213> ORGANISM: Artificial
<220> FEATURE:
<223> OTHER INFORMATION: Encodes Cycle 3 BFP gene

<400> SEQUENCE: 32

```
gtggcacttt tcggggaaat gtgcgcggaa cccctatttg tttatttttc taaatacatt     60
caaatatgta tccgctcatg agacaataac cctgataaat gcttcaataa tattgaaaaa    120
ggaagagtat gagtattcaa catttccgtg tcgcccttat ccctttttt gcggcatttt    180 gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcacttttaa agttctgcta tgtggcgcgg    360
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca acatggggg gatcatgtaa    600 ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
```

```
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc cttttttgata  1080
atctcatgac caaaatccct taacgtgagt tttcgttcca ctgagcgtca gaccccgtag   1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag cgcagcggt cgggctgaac ggggggttcg tgcacacagc    1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatgaaaaa cgccagcaac gcggccttt tacggttcct ggccttttgc tggccttttg    1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct gggtaccgat gagtaaagga   2220
gaagaacttt tcactggagt tgtcccaatt cttgttgaat tagatggtga tgttaatggg   2280
cacaaatttt ctgtcagtgg agagggtgaa ggtgatgcta catacggaaa gcttacactt   2340
aaatttattt gcactactgg aaaactacct gttccatggc caacacttgt cactactttc   2400
tctcatggtg ttcaatgctt ttctcgttat ccggatcata tgaaacggca tgactttttc   2460
aagagtgcca tgcccgaagg ttatgtacag gaacgcacta tatctttcaa agatgacggg   2520
aactacaaga cgcgtgctga agtcaagttt gaaggtgata cccttgttaa tcgtatcgag   2580
ttaaaaggta ttgattttaa agaagatgga acattctcg acacaaact cgagtacaac    2640
tttaactcac acaatgtata catcacggca gacaaacaaa gaatggaat caaagctaac    2700
ttcaaaattc gccacaacat tgaagatgga tccgttcaac tagcagacca ttatcaacaa   2760
aatactccaa ttggcgatgg ccctgtcctt ttaccagaca accattacct gtcgacacaa   2820
tctgcccttt cgaaagatcc caacgaaaag cgtgaccaca tggtccttct tgagtttgta   2880
actgctgctg ggattacaca tggcatggat gaactataca ataagaatt cctgcagccc    2940
gggggatcca ctagttctag agcggccgcc accgcggtgg agctccaatt cgccctatag   3000
tgagtcgtat tacgcgcgct cactggccgt cgttttacaa cgtcgtgact gggaaaaccc   3060
tggcgttacc caacttaatc gccttgcagc acatccccct ttcgccagct ggcgtaatag   3120
cgaagaggcc cgcaccgatc gcccttccca acagttgcgc agcctgaatg gcgaatggga   3180
```

```
cgcgccctgt agcggcgcat taagcgcggc gggtgtggtg gttacgcgca gcgtgaccgc    3240
tacacttgcc agcgccctag cgcccgctcc tttcgctttc ttcccttcct ttctcgccac    3300
gttcgccggc ttccccgtc aagctctaaa tcggggctc cctttagggt tccgatttag     3360
tgctttacgg cacctcgacc ccaaaaaact tgattagggt gatggttcac gtagtgggcc    3420
atcgccctga tagacggttt ttcgcccttt gacgttggag tccacgttct ttaatagtgg    3480
actcttgttc caaactggaa caacactcaa ccctatctcg gtctattctt ttgatttata    3540
agggattttg ccgatttcgg cctattggtt aaaaatgag ctgatttaac aaaaatttaa     3600
cgcgaatttt aacaaaatat taacgcttac aatttag                             3637

<210> SEQ ID NO 33
<211> LENGTH: 717
<212> TYPE: DNA
<213> ORGANISM: Aequorea victoria BFP Cycle 3 ORF

<400> SEQUENCE: 33
atgagtaaag gagaagaact tttcactgga gttgtcccaa ttcttgttga attagatggt      60
gatgttaatg ggcacaaatt ttctgtcagt ggagagggtg aaggtgatgc tacatacgga     120
aagcttacac ttaaatttat ttgcactact ggaaaactac ctgttccatg ccaacactt     180 gtcactactt tctctcatgg tgttcaatgc ttttctcgtt atccggatca tatgaaacgg    240
catgactttt tcaagagtgc catgcccgaa ggttatgtac aggaacgcac tatatctttc    300
aaagatgacg ggaactacaa gacgcgtgct gaagtcaagt ttgaaggtga tacccttgtt    360
aatcgtatcg agttaaaagg tattgatttt aaagaagatg gaaacattct cggacacaaa    420
ctcgagtaca actttaactc acacaatgta tacatcacgg cagacaaaca aaagaatgga    480
atcaaagcta acttcaaaat tcgccacaac attgaagatg gatccgttca actagcagac    540
cattatcaac aaaatactcc aattggcgat ggccctgtcc ttttaccaga caaccattac    600
ctgtcgacac aatctgccct ttcgaaagat cccaacgaaa agcgtgacca catggtcctt    660
cttgagtttg taactgctgc tgggattaca catggcatgg atgaactata caaataa       717

<210> SEQ ID NO 34
<211> LENGTH: 295
<212> TYPE: PRT
<213> ORGANISM: Selaginella lepidophylla

<400> SEQUENCE: 34

Met Ala Thr Thr Lys Thr Ser Gly Met Ala Leu Ala Leu Leu Leu Val
1               5                   10                  15

Ala Ala Leu Ala Val Gly Ala Ala Ala Trp Gly Lys Glu Gly His Arg
            20                  25                  30

Leu Thr Cys Met Val Ala Glu Pro Phe Leu Ser Ser Glu Ser Lys Gln
        35                  40                  45

Ala Val Glu Glu Leu Leu Ser Gly Arg Asp Leu Pro Asp Leu Cys Ser
    50                  55                  60

Trp Ala Asp Gln Ile Arg Arg Ser Tyr Lys Phe Arg Trp Thr Gly Pro
65                  70                  75                  80

Leu His Tyr Ile Asp Thr Pro Asp Asn Leu Cys Thr Tyr Asp Tyr Asp
                85                  90                  95

Arg Asp Cys His Asp Ser His Gly Lys Lys Asp Val Cys Val Ala Gly
            100                 105                 110

Gly Ile Asn Asn Tyr Ser Ser Gln Leu Glu Thr Phe Leu Asp Ser Glu
        115                 120                 125
```

```
Ser Ser Ser Tyr Asn Leu Thr Glu Ala Leu Leu Phe Leu Ala His Phe
        130                 135                 140

Val Gly Asp Ile His Gln Pro Leu His Val Ala Phe Thr Ser Asp Ala
145                 150                 155                 160

Gly Gly Asn Gly Val His Val Arg Trp Phe Gly Arg Lys Ala Asn Leu
                165                 170                 175

His His Val Trp Asp Thr Glu Phe Ile Ser Arg Ala Asn Arg Val Tyr
            180                 185                 190

Tyr His Asp Ile Ser Lys Met Leu Arg Asn Ile Thr Arg Ser Ile Thr
        195                 200                 205

Lys Lys Asn Phe Asn Ser Trp Ser Arg Cys Lys Thr Asp Pro Ala Ala
        210                 215                 220

Cys Ile Asp Ser Tyr Ala Thr Glu Ser Ile Asp Ala Ser Cys Asn Trp
225                 230                 235                 240

Ala Tyr Lys Asp Ala Pro Asp Gly Ser Ser Leu Asp Asp Tyr Phe
                245                 250                 255

Ser Ser Arg Leu Pro Ile Val Glu Gln Arg Leu Ala Gln Gly Gly Val
                260                 265                 270

Arg Leu Ala Ser Ile Leu Asn Arg Ile Phe Gly Gly Ala Lys Ser Asn
            275                 280                 285

Arg Ser Ser Arg Ser Ser Met
        290                 295

<210> SEQ ID NO 35
<211> LENGTH: 19
<212> TYPE: PRT
<213> ORGANISM: Apium graveolens fragment of Cel I expressed by TMV

<400> SEQUENCE: 35

Asp Met Cys Val Ala Gly Ala Ile Gln Asn Phe Thr Ser Gln Leu Gly
1               5                   10                  15

His Phe Arg

<210> SEQ ID NO 36
<211> LENGTH: 14
<212> TYPE: DNA
<213> ORGANISM: Artificial
<220> FEATURE:
<223> OTHER INFORMATION: oligonucleotide

<400> SEQUENCE: 36
agatcgatca attg                                                         14

<210> SEQ ID NO 37
<211> LENGTH: 14
<212> TYPE: DNA
<213> ORGANISM: Artificial
<220> FEATURE:
<223> OTHER INFORMATION: oligonucleotide

<400> SEQUENCE: 37
agaccgatcg attg                                                         14

<210> SEQ ID NO 38
<211> LENGTH: 14
<212> TYPE: DNA
<213> ORGANISM: Artificial
<220> FEATURE:
<223> OTHER INFORMATION: oligonucleotide
```

-continued

```
<400> SEQUENCE: 38
agatcgatcg attg                                                         14

<210> SEQ ID NO 39
<211> LENGTH: 14
<212> TYPE: DNA
<213> ORGANISM: Artificial
<220> FEATURE:
<223> OTHER INFORMATION: oligonucleotide

<400> SEQUENCE: 39
agaccgatca attg                                                         14

<210> SEQ ID NO 40
<211> LENGTH: 10
<212> TYPE: DNA
<213> ORGANISM: Artificial
<220> FEATURE:
<223> OTHER INFORMATION: oligonucleotide

<400> SEQUENCE: 40
agatcaattg                                                              10

<210> SEQ ID NO 41
<211> LENGTH: 10
<212> TYPE: DNA
<213> ORGANISM: Artificial
<220> FEATURE:
<223> OTHER INFORMATION: oligonucleotide

<400> SEQUENCE: 41
agaccgattg                                                              10

<210> SEQ ID NO 42
<211> LENGTH: 4
<212> TYPE: PRT
<213> ORGANISM: Artificial
<220> FEATURE:
<223> OTHER INFORMATION: linker
<220> FEATURE:
<221> NAME/KEY: misc_feature
<222> LOCATION: (2)..(2)
<223> OTHER INFORMATION: Xaa can be any naturally occurring amino acid

<400> SEQUENCE: 42

Pro Xaa Gly Pro
1
```

What is claimed is:

1. An in vitro method of generating mutations in a zone around a particular nucleotide within a desired polynucleotide comprising:
    (a) preparing at least one partially complementary polynucleotide having at least one non-complementary nucleotide within the corresponding zone of the desired polynucleotide;
    (b) forming at least one heteroduplex between said desired polynucleotide and said partially complementary polynucleotide;
    (c) combining said heteroduplex with at least one nucleotide analogue and an effective amount of an agent or agents with exonuclease activity, polymerase activity, and mismatch-directed strand cleavage activity, wherein said mismatch-directed strand cleavage activity is provided by the protein of SEQ ID NO: 34 (RES I);
    (d) allowing sufficient time for the nucleotide analogue to be incorporated into either said desired polynucleotide, said partially complementary polynucleotide, or both polynucleotides; and
    (e) replicating a polynucleotide of step d such that mutations are generated in a zone around a particular nucleotide within the desired polynucleotide.

2. The method according to claim 1 further comprising including a ligase activity in step c.

3. The method of claim 1 wherein said heteroduplex polynucleotide is circular.

4. The method of claim 1 wherein said heteroduplex polynucleotide is linear.

5. The method of claim 1 wherein said heteroduplex polynucleotide is a replicon.

6. The method of claim 1 wherein said agents having mismatch-directed strand cleavage activity, exonuclease activity and polymerase activity are added sequentially.

7. The method of claim 1 wherein said agents having mismatch-directed strand cleavage activity, exonuclease activity and polymerase activity are added concurrently.

8. The method of claim 2 wherein said ligase activity is provided by T4 DNA ligase, *E. coli* DNA ligase, or Taq DNA ligase.

9. The method of claim 1 wherein said agent with exonuclease activity and polymerase activity is T4 DNA polymerase, T7 DNA polymerase, *E. coli* Pol I, or Pfu DNA polymerase.

10. The method of claim 1 wherein said agent with exonuclease activity and polymerase activity is *E. coli* Pol I.

11. The method of claim 2 wherein said effective amount of mismatch-directed strand cleavage activity, exonuclease activity/polymerase activity, and ligase activity are provided by RES I, T4 DNA polymerase, and *E. coli* DNA ligase respectively.

12. The method of claim 2 wherein said effective amount of mismatch-directed strand cleavage activity, exonuclease activity/polymerase activity, and ligase activity are provided by RES I, *E. coli* Pol I, and *E. coli* DNA ligase respectively.

13. The method of claim 1 wherein said heteroduplex polynucleotide has greater than 95% identity between strands of the heteroduplex.

14. The method of claim 1 wherein said heteroduplex polynucleotide has about 95% identity between strands of the heteroduplex.

15. The method of claim 1 wherein said heteroduplex polynucleotide has about 90% identity between strands of the heteroduplex.

16. The method of claim 1 wherein said heteroduplex polynucleotide has about 85% identity between strands of the heteroduplex.

17. The method of claim 1 wherein said heteroduplex polynucleotide has about 80% identity between strands of the heteroduplex.

18. The method of claim 1 wherein said heteroduplex polynucleotide has about 75% identity between strands of the heteroduplex.

19. The method of claim 1 wherein the heteroduplex polynucleotide is about 1000 Kb in length.

* * * * *